(12) United States Patent
Jeschke et al.

(10) Patent No.: US 9,012,360 B2
(45) Date of Patent: Apr. 21, 2015

(54) SYNERGISTIC COMBINATIONS OF ACTIVE INGREDIENTS

(75) Inventors: Peter Jeschke, Bergisch Gladbach (DE); Robert Velten, Langenfeld (DE); Heike Hungenberg, Langenfeld (DE); Wolfgang Thielert, Odenthal (DE)

(73) Assignee: Bayer Intellectual Property GmbH, Monheim (DE)

( * ) Notice: Subject to any disclaimer, the term of this patent is extended or adjusted under 35 U.S.C. 154(b) by 194 days.

(21) Appl. No.: 13/256,346

(22) PCT Filed: Mar. 25, 2009

(86) PCT No.: PCT/EP2009/002170
§ 371 (c)(1),
(2), (4) Date: Oct. 27, 2011

(87) PCT Pub. No.: WO2010/108507
PCT Pub. Date: Sep. 30, 2010

(65) Prior Publication Data
US 2012/0035050 A1 Feb. 9, 2012

(51) Int. Cl.
*A01N 37/46* (2006.01)
*A01N 37/50* (2006.01)
*A01N 43/36* (2006.01)
*A01N 43/40* (2006.01)
*A01N 43/653* (2006.01)
*A01N 57/12* (2006.01)
*A01N 43/78* (2006.01)
*A61K 31/366* (2006.01)
*A61K 45/06* (2006.01)

(52) U.S. Cl.
CPC ........... *A01N 43/40* (2013.01); *A01N 43/78* (2013.01); *A61K 31/366* (2013.01); *A61K 45/06* (2013.01)

(58) Field of Classification Search
USPC .......... 504/100; 514/336, 357, 365, 141, 384, 514/422, 479, 538, 539
See application file for complete search history.

(56) References Cited

U.S. PATENT DOCUMENTS

| | | |
|---|---|---|
| 1,972,961 A | 9/1934 | Tisdale et al. |
| 2,504,404 A | 4/1950 | Flenner |
| 2,553,770 A | 5/1951 | Kittleson |
| 2,588,428 A | 3/1952 | Stewart et al. |
| 3,010,968 A | 11/1961 | Loux |
| 3,178,447 A | 4/1965 | Kohn |
| 3,206,468 A | 9/1965 | Grenda |
| 3,248,400 A | 4/1966 | Flieg et al. |
| 3,249,499 A | 5/1966 | Von Schmeling et al. |
| 3,290,353 A | 12/1966 | Battershell et al. |
| 3,379,610 A | 4/1968 | Lyon et al. |
| 3,499,030 A | 3/1970 | Kuhle et al. |
| 3,499,951 A | 3/1970 | Schrader et al. |
| 3,513,241 A | 5/1970 | Hoyer et al. |
| 3,546,813 A | 12/1970 | Frohberger et al. |
| 3,629,428 A | 12/1971 | Seki et al. |
| 3,631,176 A | 12/1971 | Klopping |
| 3,745,170 A | 7/1973 | Fujinami et al. |
| 3,745,187 A | 7/1973 | Noguchi et al. |
| 3,755,350 A | 8/1973 | Sauli |
| 3,856,814 A | 12/1974 | Taninaka et al. |
| 3,912,752 A | 10/1975 | Meiser et al. |
| 3,952,002 A | 4/1976 | Kramer et al. |
| 3,966,750 A | 6/1976 | Mangold et al. |
| 3,991,071 A | 11/1976 | Brookes et al. |
| 4,068,077 A | 1/1978 | Goetz et al. |
| 4,079,062 A | 3/1978 | Van Reet et al. |
| 4,093,743 A | 6/1978 | Yabutani et al. |
| 4,094,990 A | 6/1978 | Hubele |
| 4,127,673 A | 11/1978 | Yamada et al. |
| 4,139,616 A | 2/1979 | Ducret et al. |
| 4,151,299 A | 4/1979 | Hubele |
| 4,239,760 A | 12/1980 | Sasse et al. |
| 4,245,432 A | 1/1981 | Dannelly |

(Continued)

FOREIGN PATENT DOCUMENTS

| | | |
|---|---|---|
| DE | 1 081 446 B | 5/1960 |
| DE | 22 50 077 C2 | 4/1973 |

(Continued)

OTHER PUBLICATIONS

Hackh's Chemical Dictionary, 4th ed., McGraw-Hill Book Co., New York, p. 170 (1977).*
"Deliberate releases and placing on the EU Market of Genetically Modified Organisms," GMO Register, European Commission Joint Research Centre, Institute for Health and Consumer Protection, accessed on the World Wide Web at gmoinfo.jrc.ec.europa,eu/gmp_browse.aspx, accessed on Mar. 2, 2012, 38 pages.

(Continued)

*Primary Examiner* — John Pak
(74) *Attorney, Agent, or Firm* — Sterne, Kessler, Goldstein & Fox P.L.L.C.

(57) ABSTRACT

The present invention relates to novel active compound combinations comprising, firstly, at least one known compound of the formula (I)

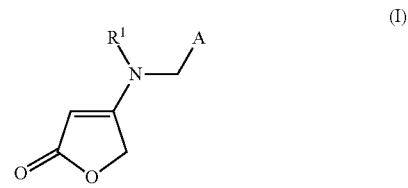

(I)

in which
$R^1$ and A have the meanings given in the description
and, secondly, at least one further known active compound from groups (2) to (27) listed in the description, which combinations are highly suitable for controlling animal pests such as insects and unwanted acarids and also phytopathogenic fungi.

12 Claims, No Drawings

(56) References Cited

U.S. PATENT DOCUMENTS

| | | | |
|---|---|---|---|
| 4,272,417 A | 6/1981 | Barke et al. |
| 4,291,049 A | 9/1981 | Bosone et al. |
| 4,432,989 A | 2/1984 | Spencer |
| 4,532,341 A | 7/1985 | Holmwood et al. |
| 4,598,085 A | 7/1986 | Heeres et al. |
| 4,652,580 A | 3/1987 | Janssen et al. |
| 4,664,696 A | 5/1987 | Schaub |
| 4,705,800 A | 11/1987 | Nyfeler et al. |
| 4,761,373 A | 8/1988 | Anderson et al. |
| 4,808,430 A | 2/1989 | Kouno |
| 4,829,085 A | 5/1989 | Wenderoth et al. |
| 4,851,405 A | 7/1989 | Krámer et al. |
| 4,910,200 A | 3/1990 | Curtze et al. |
| 4,931,560 A | 6/1990 | Hubele |
| 4,931,581 A | 6/1990 | Schurter et al. |
| 4,988,734 A | 1/1991 | Kraatz et al. |
| 5,013,659 A | 5/1991 | Bedbrook et al. |
| 5,084,082 A | 1/1992 | Sebastian |
| 5,087,635 A | 2/1992 | Shaber |
| 5,112,849 A | 5/1992 | Staub et al. |
| 5,141,870 A | 8/1992 | Bedbrook et al. |
| 5,198,599 A | 3/1993 | Thill |
| 5,256,683 A | 10/1993 | Hutt et al. |
| 5,266,585 A | 11/1993 | Hubele et al. |
| 5,273,894 A | 12/1993 | Strauch et al. |
| 5,276,268 A | 1/1994 | Strauch et al. |
| 5,304,732 A | 4/1994 | Anderson et al. |
| 5,331,107 A | 7/1994 | Anderson et al. |
| 5,334,607 A | 8/1994 | Sauter et al. |
| 5,378,824 A | 1/1995 | Bedbrook et al. |
| 5,434,283 A | 7/1995 | Wong et al. |
| 5,453,531 A | 9/1995 | Seitz et al. |
| 5,463,175 A | 10/1995 | Barry et al. |
| 5,561,236 A | 10/1996 | Leemans et al. |
| 5,593,996 A | 1/1997 | Pees et al. |
| 5,605,011 A | 2/1997 | Bedbrook et al. |
| 5,637,489 A | 6/1997 | Strauch et al. |
| 5,637,729 A | 6/1997 | Lacroix et al. |
| 5,646,024 A | 7/1997 | Leemans et al. |
| 5,648,477 A | 7/1997 | Leemans et al. |
| 5,679,676 A | 10/1997 | Krüger et al. |
| 5,712,107 A | 1/1998 | Nichols |
| 5,731,180 A | 3/1998 | Dietrich |
| 5,739,082 A | 4/1998 | Donn |
| 5,767,361 A | 6/1998 | Dietrich |
| 5,773,702 A | 6/1998 | Penner et al. |
| 5,776,760 A | 7/1998 | Barry et al. |
| 5,789,428 A | 8/1998 | Shibata et al. |
| 5,789,430 A | 8/1998 | Jautelat et al. |
| 5,824,790 A | 10/1998 | Keeling et al. |
| 5,840,946 A | 11/1998 | Wong et al. |
| 5,866,782 A | 2/1999 | Iwabuchi et al. |
| 5,869,517 A | 2/1999 | Müller et al. |
| 5,876,739 A | 3/1999 | Turnblad et al. |
| 5,908,810 A | 6/1999 | Donn |
| 5,908,975 A | 6/1999 | Caimi et al. |
| 5,928,937 A | 7/1999 | Kakefuda et al. |
| 5,948,932 A | 9/1999 | Grote et al. |
| 5,965,755 A | 10/1999 | Sernyk et al. |
| 5,969,169 A | 10/1999 | Fan |
| 5,986,135 A | 11/1999 | Pfrengle et al. |
| 5,998,450 A | 12/1999 | Eicken et al. |
| 6,013,861 A | 1/2000 | Bird et al. |
| 6,063,947 A | 5/2000 | DeBonte et al. |
| 6,103,717 A | 8/2000 | Heinemann et al. |
| 6,162,966 A | 12/2000 | Kossmann et al. |
| 6,169,190 B1 | 1/2001 | Lanuza et al. |
| 6,229,072 B1 | 5/2001 | Burns et al. |
| 6,245,968 B1 | 6/2001 | Boudec et al. |
| 6,268,549 B1 | 7/2001 | Sailland et al. |
| 6,270,828 B1 | 8/2001 | DeBonte et al. |
| 6,284,479 B1 | 9/2001 | Nichols |
| 6,323,392 B1 | 11/2001 | Charne |
| 6,355,634 B1 | 3/2002 | Isenring et al. |
| 6,566,587 B1 | 5/2003 | Lebrun et al. |
| 6,590,141 B1 | 7/2003 | Frohberg |
| 6,616,054 B1 | 9/2003 | Norton |
| 6,710,062 B1 | 3/2004 | Hayashi et al. |
| 6,734,341 B2 | 5/2004 | Singletary et al. |
| 6,791,010 B1 | 9/2004 | Frohberg |
| 6,812,010 B1 | 11/2004 | Derose et al. |
| 6,812,229 B1 | 11/2004 | Ozaki et al. |
| 6,890,732 B1 | 5/2005 | Loerz et al. |
| 6,891,088 B1 | 5/2005 | Neuhaus et al. |
| 7,112,665 B1 | 9/2006 | Leemans et al. |
| 7,186,898 B1 | 3/2007 | Kossmann et al. |
| 2001/0007155 A1 | 7/2001 | Kossmann et al. |
| 2001/0011378 A1 | 8/2001 | Kossmann et al. |
| 2001/0018442 A1 | 8/2001 | Gayer et al. |
| 2002/0031826 A1 | 3/2002 | Nichols |
| 2002/0088023 A1 | 7/2002 | Kossmann et al. |
| 2002/0091067 A1 | 7/2002 | Assmann et al. |
| 2002/0092040 A1 | 7/2002 | Kossmann et al. |
| 2002/0133849 A1 | 9/2002 | Kossmann et al. |
| 2002/0138876 A1 | 9/2002 | Block et al. |
| 2002/0162138 A1 | 10/2002 | Kossmann et al. |
| 2002/0198222 A1 | 12/2002 | Bruns et al. |
| 2003/0027842 A1 | 2/2003 | Assmann et al. |
| 2003/0093133 A1 | 5/2003 | Crowe et al. |
| 2003/0093834 A1 | 5/2003 | Loerz et al. |
| 2003/0106100 A1 | 6/2003 | Kossmann et al. |
| 2003/0138927 A1 | 7/2003 | Heyer et al. |
| 2003/0167527 A1 | 9/2003 | Emmermann et al. |
| 2003/0167529 A1 | 9/2003 | Landschutze |
| 2003/0175931 A1 | 9/2003 | Kossmann et al. |
| 2003/0176428 A1 | 9/2003 | Schneidersmann et al. |
| 2003/0229923 A1 | 12/2003 | Kossmann et al. |
| 2004/0014092 A1 | 1/2004 | Heyer et al. |
| 2004/0039043 A1 | 2/2004 | Elbe et al. |
| 2004/0073966 A1 | 4/2004 | Zink et al. |
| 2004/0110254 A1 | 6/2004 | Buttcher et al. |
| 2004/0110771 A1 | 6/2004 | Blasco et al. |
| 2005/0124815 A1 | 6/2005 | Elbe et al. |
| 2005/0143428 A1 | 6/2005 | Dunkel et al. |
| 2005/0234110 A1* | 10/2005 | Mansfield et al. ............ 514/357 |
| 2005/0257283 A1 | 11/2005 | Matringe et al. |
| 2006/0015966 A1 | 1/2006 | Landschutze |
| 2006/0116414 A1 | 6/2006 | Dunkel et al. |
| 2006/0168690 A1 | 7/2006 | Shibatani et al. |
| 2006/0211771 A1 | 9/2006 | Elbe et al. |
| 2008/0250533 A1 | 10/2008 | Frohberg |
| 2009/0247551 A1 | 10/2009 | Jeschke et al. |
| 2009/0253749 A1 | 10/2009 | Jeschke et al. |
| 2009/0280981 A1 | 11/2009 | Jeschke et al. |
| 2010/0048647 A1* | 2/2010 | Suwa ............................ 514/357 |
| 2010/0240705 A1 | 9/2010 | Jeschke et al. |
| 2012/0021901 A1 | 1/2012 | Hungenberg et al. |
| 2012/0077675 A1 | 3/2012 | Hungenberg et al. |
| 2012/0094829 A1 | 4/2012 | Jeschke et al. |
| 2012/0115720 A1 | 5/2012 | Hungenberg et al. |

FOREIGN PATENT DOCUMENTS

| | | |
|---|---|---|
| DE | 26 56 747 A1 | 6/1978 |
| DE | 140 041 A1 | 2/1980 |
| DE | 30 30 026 A1 | 3/1981 |
| DE | 151 404 A1 | 10/1981 |
| DE | 10 2006 023 263 A1 | 11/2007 |
| DE | 10 2007 045 920 A1 | 4/2009 |
| EP | 0 015 756 A1 | 9/1980 |
| EP | 0 019 450 A1 | 11/1980 |
| EP | 0 031 257 A2 | 7/1981 |
| EP | 0 068 813 A2 | 1/1983 |
| EP | 0 078 663 A2 | 5/1983 |
| EP | 0 145 294 A2 | 6/1985 |
| EP | 0 155 509 A1 | 9/1985 |
| EP | 0 183 458 A1 | 6/1986 |
| EP | 0 234 242 A2 | 9/1987 |
| EP | 0 248 086 A1 | 12/1987 |
| EP | 0 256 503 A2 | 2/1988 |
| EP | 0 258 161 A2 | 3/1988 |
| EP | 0 262 393 A1 | 4/1988 |
| EP | 0 270 111 A1 | 6/1988 |
| EP | 0 278 595 A2 | 8/1988 |

(56) References Cited

FOREIGN PATENT DOCUMENTS

| | | |
|---|---|---|
| EP | 0 298 196 A1 | 1/1989 |
| EP | 0 315 502 A1 | 5/1989 |
| EP | 0 329 397 A1 | 8/1989 |
| EP | 0 339 418 A2 | 11/1989 |
| EP | 0 382 375 A2 | 8/1990 |
| EP | 0 393 911 A1 | 10/1990 |
| EP | 0 398 692 A2 | 11/1990 |
| EP | 0 537 957 A1 | 4/1993 |
| EP | 0 539 588 A1 | 5/1993 |
| EP | 0 571 427 B1 | 12/1993 |
| EP | 0 596 254 A1 | 5/1994 |
| EP | 0 600 629 A1 | 6/1994 |
| EP | 0 604 019 A1 | 6/1994 |
| EP | 0 639 574 A1 | 2/1995 |
| EP | 0 663 956 B1 | 7/1995 |
| EP | 0 719 338 B1 | 7/1996 |
| EP | 0 728 213 B1 | 8/1996 |
| EP | 0 737 682 A1 | 10/1996 |
| EP | 0 860 438 A1 | 8/1998 |
| EP | 0 897 904 A1 | 2/1999 |
| EP | 1 028 125 A1 | 8/2000 |
| EP | 1 414 803 | 5/2004 |
| GB | 857383 A | 12/1960 |
| GB | 935981 A | 9/1963 |
| GB | 988630 A | 4/1965 |
| GB | 1094567 A | 12/1967 |
| GB | 1103989 A | 2/1968 |
| GB | 1114155 A | 5/1968 |
| GB | 1 425 621 | 2/1976 |
| GB | 1 492 110 | 11/1977 |
| JP | 7-206608 A | 8/1995 |
| JP | 2001-187786 A | 7/2001 |
| JP | 2006-304779 A | 11/2006 |
| WO | WO 89/10396 A1 | 11/1989 |
| WO | WO 91/02069 A1 | 2/1991 |
| WO | WO 92/05251 A1 | 4/1992 |
| WO | WO 92/13830 A1 | 8/1992 |
| WO | WO 94/04693 A2 | 3/1994 |
| WO | WO 94/09144 A1 | 4/1994 |
| WO | WO 94/11520 A2 | 5/1994 |
| WO | WO 94/21795 A1 | 9/1994 |
| WO | WO 94/26722 A1 | 11/1994 |
| WO | WO 95/04826 A1 | 2/1995 |
| WO | WO 95/26407 A1 | 10/1995 |
| WO | WO 95/35026 A1 | 12/1995 |
| WO | WO 96/01559 A1 | 1/1996 |
| WO | WO 96/01904 A1 | 1/1996 |
| WO | WO 96/18631 A1 | 6/1996 |
| WO | WO 96/21023 A1 | 7/1996 |
| WO | WO 96/23793 A1 | 8/1996 |
| WO | WO 96/33270 A1 | 10/1996 |
| WO | WO 96/34968 A2 | 11/1996 |
| WO | WO 97/20936 A1 | 6/1997 |
| WO | WO 97/41218 A1 | 11/1997 |
| WO | WO 97/47806 A1 | 12/1997 |
| WO | WO 97/47807 A1 | 12/1997 |
| WO | WO 97/47808 A1 | 12/1997 |
| WO | WO 98/00549 A1 | 1/1998 |
| WO | WO 98/20145 A2 | 5/1998 |
| WO | WO 98/22604 A1 | 5/1998 |
| WO | WO 98/23155 A1 | 6/1998 |
| WO | WO 98/27806 A1 | 7/1998 |
| WO | WO 98/32326 A2 | 7/1998 |
| WO | WO 99/12950 A2 | 3/1999 |
| WO | WO 99/14202 A2 | 3/1999 |
| WO | WO 99/24585 A1 | 5/1999 |
| WO | WO 99/42447 A1 | 8/1999 |
| WO | WO 99/53072 A2 | 10/1999 |
| WO | WO 99/57965 A1 | 11/1999 |
| WO | WO 99/66050 A1 | 12/1999 |
| WO | WO 00/04173 A1 | 1/2000 |
| WO | WO 00/11192 A2 | 3/2000 |
| WO | WO 00/14249 A1 | 3/2000 |
| WO | WO 00/14701 A1 | 3/2000 |
| WO | WO 00/28052 A2 | 5/2000 |
| WO | WO 00/66746 A1 | 11/2000 |
| WO | WO 00/66747 A1 | 11/2000 |
| WO | WO 00/73422 A1 | 12/2000 |
| WO | WO 00/77229 A2 | 12/2000 |
| WO | WO 01/14569 A2 | 3/2001 |
| WO | WO 01/17333 A1 | 3/2001 |
| WO | WO 01/19975 A2 | 3/2001 |
| WO | WO 01/24615 A1 | 4/2001 |
| WO | WO 01/65922 A2 | 9/2001 |
| WO | WO 01/66704 A2 | 9/2001 |
| WO | WO 01/87822 A1 | 11/2001 |
| WO | WO 01/98509 A2 | 12/2001 |
| WO | WO 02/26995 A1 | 4/2002 |
| WO | WO 02/28186 A2 | 4/2002 |
| WO | WO 02/34923 A2 | 5/2002 |
| WO | WO 02/36782 A2 | 5/2002 |
| WO | WO 02/38542 A1 | 5/2002 |
| WO | WO 02/45485 A1 | 6/2002 |
| WO | WO 02/079410 A2 | 10/2002 |
| WO | WO 02/080675 A2 | 10/2002 |
| WO | WO 02/101059 A2 | 12/2002 |
| WO | WO 03/013226 A2 | 2/2003 |
| WO | WO 03/014103 A1 | 2/2003 |
| WO | WO 03/033540 A2 | 4/2003 |
| WO | WO 03/071860 A2 | 9/2003 |
| WO | WO 03/074491 A1 | 9/2003 |
| WO | WO 03/092360 A2 | 11/2003 |
| WO | WO 2004/016088 A2 | 2/2004 |
| WO | WO 2004/035589 A1 | 4/2004 |
| WO | WO 2004/040012 A2 | 5/2004 |
| WO | WO 2004/053219 A2 | 6/2004 |
| WO | WO 2004/056999 A1 | 7/2004 |
| WO | WO 2004/078983 A2 | 9/2004 |
| WO | WO 2004/090140 A2 | 10/2004 |
| WO | WO 2004/106529 A2 | 12/2004 |
| WO | WO 2005/002324 A2 | 1/2005 |
| WO | WO 2005/002359 A2 | 1/2005 |
| WO | WO 2005/012515 A2 | 2/2005 |
| WO | WO 2005/017157 A1 | 2/2005 |
| WO | WO 2005/020673 A1 | 3/2005 |
| WO | WO 2005/030941 A1 | 4/2005 |
| WO | WO 2005/030942 A1 | 4/2005 |
| WO | WO 2005/093093 A2 | 10/2005 |
| WO | WO 2005/095617 A2 | 10/2005 |
| WO | WO 2005/095618 A2 | 10/2005 |
| WO | WO 2005/095619 A1 | 10/2005 |
| WO | WO 2005/095632 A2 | 10/2005 |
| WO | WO 2005/123927 A1 | 12/2005 |
| WO | WO 2006/007373 A2 | 1/2006 |
| WO | WO 2006/015376 A2 | 2/2006 |
| WO | WO 2006/018319 A1 | 2/2006 |
| WO | WO 2006/021972 A1 | 3/2006 |
| WO | WO 2006/024351 A1 | 3/2006 |
| WO | WO 2006/032469 A2 | 3/2006 |
| WO | WO 2006/032538 A1 | 3/2006 |
| WO | WO 2006/045633 A1 | 5/2006 |
| WO | WO 2006/060634 A2 | 6/2006 |
| WO | WO 2006/063862 A1 | 6/2006 |
| WO | WO 2006/072603 A2 | 7/2006 |
| WO | WO 2006/103107 A1 | 10/2006 |
| WO | WO 2006/108702 A1 | 10/2006 |
| WO | WO 2006/133827 A2 | 12/2006 |
| WO | WO 2006/136351 A2 | 12/2006 |
| WO | WO 2007/009823 A1 | 1/2007 |
| WO | WO 2007/024782 A2 | 3/2007 |
| WO | WO 2007/027777 A2 | 3/2007 |
| WO | WO 2007/039314 A2 | 4/2007 |
| WO | WO 2007/039316 A1 | 4/2007 |
| WO | WO 2007/107326 A1 | 9/2007 |
| WO | WO 2007/115643 A1 | 10/2007 |
| WO | WO 2007/115644 A1 | 10/2007 |
| WO | WO 2007/131699 A2 | 11/2007 |
| WO | WO 2008/017518 A1 | 2/2008 |
| WO | WO 2008/080630 A1 | 7/2008 |
| WO | WO 2008/080631 A1 | 7/2008 |

(56) References Cited

FOREIGN PATENT DOCUMENTS

| WO | WO 2008/090008 A1 | 7/2008 |
|---|---|---|
| WO | WO 2008/126922 | * 10/2008 |

OTHER PUBLICATIONS

"The Vip nomenclature," accessed on the World Wide Web at lifesci.sussex.ac.uk/Home/Neil_Crickmore/Bt/vip.html, accessed on Mar. 2, 2012, 3 pages.

Barry, G., et al., "Inhibitors of Amino Acid Biosynthesis: Strategies for Imparting Glyphosate Tolerance to Crop Plants," *Biosynthesis and Molecular Regulation of Amino Acids in Plants* 7:139-145, Singh, B.K., et al., eds., American Society of Plant Physiologists, United States (1992).

Bauer, T.A., et al., "Response of Selected Weed Species to Postemergence Imazethapyr and Bentazon," *Weed Tech.* 9:236-242, The Weed Science Society of America, United States (1995).

Blackshaw, R.E., "HOE-39866 Use in Chemical Fallow Systems," *Weed Tech.* 3:420-428, The Weed Science Society of America, United States (1989).

Blackshaw, R.E., "Synergistic Mixes of DPX-A7881 and Clopyralid in Canola (*Brassica napus*)," *Weed Tech.* 3:690-695, The Weed Science Society of America, United States (1989).

Blackshaw, R.E., et al., "Herbicide Combinations for Postemergent Weed Control in Safflower (*Carthamus tinctorius*)," *Weed Tech.* 4:97-104, The Weed Science Society of America, United States (1990).

Blouin, D.C., et al., "Analysis of Synergistic and Antagonistic Effects of Herbicides Using Nonlinear Mixed-Model Methodology," *Weed Tech.* 18:464-472, The Weed Science Society of America, United States (2004).

Bradley, P.R., et al., "Response of Sorghum (*Sorghum bicolor*) to Atrazine, Ammonium Sulfate, and Glyphosate," *Weed Tech.* 14:15-18, The Weed Science Society of America, United States (2000).

Buker, III, R.S., et al., "Confirmation and Control of a Paraquat-Tolerant Goosegrass (*Eleusine indica*) Biotype," *Weed Tech.* 16:309-313, The Weed Science Society of America, United States (2002).

Burke, I.C., et al., "CGA-362622 Antagonizes Annual Grass Control with Clethodim," *Weed Tech.* 16:749-754, The Weed Science Society of America, United States (2002).

Colby, S.R., "Calculating Synergistic and Antagonistic Responses of Herbicide Combinations," *Weeds* 15:20-22, Weed Society of America, United States (1967).

Comai, L., et al., "An Altered aroA Gene Product Confers Resistance to the Herbicide Glyphosate," *Science* 221(4608):370-371, The American Association for the Advancement of Science, United States (1983).

Crickmore, N., et al., "Revision of the Nomenclature for the *Bacillus thuringiensis* Pesticidal Crystal Proteins," *Microbiology and Molecular Biology Reviews* 62(3):807-813, American Society for Microbiology, United States (1998).

Draber, W., and Wegler, R., "Gibberelline," *Chemie der Pflanzenschutz- und Schädlingsbekämpfungsmittel* 2:401-412, Springer-Verlag, Germany (1970).

English language translation of Draber, W., and Wegler, R., "Gibberelline," *Chemie der Pflanzenschutz- und Schädlingsbekämpfungsmittel* 2:401-412, Springer-Verlag, Germany (1970).

Flint, J.L., et al., "Analyzing Herbicide Interactions: A Statistical Treatment of Colby's Method," *Weed Tech.* 2:304-309, The Weed Science Society of America, United States (1988).

Gasser, C.S., et al., "Structure, Expression, and Evolution of the 5-Enolpyruvylshikimate-3-phosphate Synthase Genes of Petunia and Tomato," *The Journal of Biological Chemistry* 263(9):4280-4289, The American Society for Biochemistry and Molecular Biology, Inc., United States. (1988).

Green, J.M., et al., "Metribuzin and Chlorimuron Mixtures for Preemergence Broadleaf Weed Control in Soybeans, *Glycine max*," *Weed Tech.* 2:355-363, The Weed Science Society of America, United States (1988).

Gillespie, G.R. and Nalewaja, J.D., "Wheat (*Triticum aestivum*) Response to Triallate Plus Chlorsulfuron," *Weed Tech.* 3:20-23, The Weed Science Society of America, United States (1989).

Harker, K.N. and O'Sullivan, A., "Synergistic Mixtures of Sethoxydim and Fluazifop on Annual Grass Weeds," *Weed Tech.* 5:310-316, The Weed Science Society of America, United States (1991).

Hufnagl, A.E., et al., "Meptyldinocap: a new active substance for control of powdery mildew," XVI International Plant Protection Congress 1:32-39, British Crop Production Council, United Kingdom (2007).

Kent, L.M., et al., "Effect of Ammonium Sulfate, Imazapyr, and Environment on the Phytotoxicity of Imazethapyr," *Weed Tech.* 5:202-205, The Weed Science Society of America, United States (1991).

Kotoula-Syka, E., et al., "Interactions between SAN 582H and Selected Safeners on Grain Sorghum (*Sorghum bicolor*) and Corn (*Zea mays*)," *Weed Tech.* 10:299-304, The Weed Science Society of America, United States (1996).

Lanclos, D.Y., et al., "Glufosinate Tank-Mix Combinations in Glufosinate-Resistant Rice (*Oryza sativa*)," *Weed Tech.* 16:659-663, The Weed Science Society of America, United States (2002).

Moellenbeck, D.J., et al., "Insecticidal proteins from *Bacillus thuringiensis* Protect corn from corn rootworms," *nature biotechnology* 19:668-672, Nature Publishing Group, United States (2001).

Norris, J.L., et al., "Weed Control from Herbicide Combinations with Three Formulations of Glyphosate," *Weed Tech.* 15:552-558, The Weed Science Society of America, United States (2001).

Novosel, K.M., et al., "Metolachlor Efficacy as Influenced by Three Acetolactate Synthase-Inhibiting Herbicides," *Weed Tech.* 12:248-253, The Weed Science Society of America, United States (1998).

Palmer, E.W., et al., "Broadleaf Weed Control in Soybean (*Glycine max*) with CGA-277476 and Four Postemergence Herbicides," *Weed Tech.* 14:617-623, The Weed Science Society of America, United States (2000).

Rummens, F.H.A., "An Improved Definition of Synergistic and Antagonistic Effects," *Weed Science* 23:4-6, The Weed Science Society of America, United States (1975).

Salzman, F.P. and Renner, K.A., "Response of Soybean to Combinations of Clomazone, Metribuzin, Linuron, Alachlor, and Atrazine," *Weed Tech.* 6:922-929, The Weed Science Society of America, United States (1992).

Schnepf, H.E., et al., "Characterization of Cry34/Cry35 Binary Insecticidal Proteins from Diverse *Bacillus thuringiensis* Strain Collections," *Applied and Environmental Microbiology* 71(4):1765-1774, American Society for Microbiology, United States (2005).

Scott, R.C., et al., "Spray Adjuvant, Formulation, and Environmental Effects on Synergism from Post-Applied Tank Mixtures of SAN 582H with Fluazifop-P, Imazethapyr, and Sethoxydim," *Weed Tech.* 12:463-469, The Weed Science Society of America, United States (1998).

Shah, D.M., et al., "Engineering Herbicide Tolerance in Transgenic Plants," *Science* 233(4762):478-481, The American Association for the Advancement of Science, United States (1986).

Shaw, D.R. and Arnold, J.C., "Weed Control from Herbicide Combinations with Glyphosate," *Weed Tech.* 16:1-6, The Weed Science Society of America, United States (2002).

Snipes, C.E and Allen, R.L., "Interaction of Graminicides Applied in Combination with Pyrithiobac," *Weed Tech.* 10:889-892, The Weed Science Society of America, United States (1996).

Sun, Y.-P., et al., "Analysis of Joint Action of Insecticides Against House Flies," *J. Econ. Entomol.* 53:887-892, Entomological Society of America, United States (1960).

Tammes, P.M.L., "Isoboles, A Graphic Representation of Synergism in Pesticides," *Neth. J. Plant Path.* 70:73-80, Springer, Germany (1964).

Tranel, P.J. and Wright, T.R., "Resistance of weeds to ALS-inhibiting herbicides: what have we learned?," *Weed Science* 50(6):700-712, Weed Science Society of America, United States (2002).

(56) References Cited

OTHER PUBLICATIONS

Wehtje, G., and Walker, R.H., "Interaction of Glyphosate and 2,4-DB for the Control of Selected Morningglory (*Ipomoea* spp.) Species," *Weed Tech. 11*:152-156, The Weed Science Society of America, United States (1997).

Worthing, C.S and Hance, R.J., "Dichlofluanid," *The Pesticide Manual 9*:247 & 827, British Crop Protection Council, United Kingdom (1991).

Zhang, W., et al., "Fenoxaprop Interactions for Barnyardgrass (*Echinochloa crusgalli*) Control in Rice," *Weed Tech. 19*:293-297, The Weed Science Society of America, United States (2005).

English language Abstract of WIPO Patent Publication No. DE 10 2007 045 920 A1 European Patent Office, espacenet database—Worldwide (2009).

English language Abstract of WIPO Patent Publication No. WO 99/57965 A1 European Patent Office, espacenet database—Worldwide (1999).

International Search Report for International Application No. PCT/EP2009/002170 European Patent Office, The Hague, Netherlands, mailed on Mar. 17, 2011.

* cited by examiner

SYNERGISTIC COMBINATIONS OF ACTIVE INGREDIENTS

The present invention relates to novel active compound combinations comprising, firstly, a known compound of the formula (I) and, secondly, at least one known fungicidally active compound, which combinations are highly suitable for controlling unwanted animal pests such as insects and also unwanted phytopathogenic fungi.

It is already known that compounds of the formula (I)

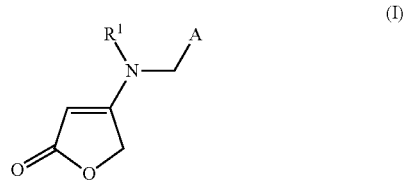

in which

A represents pyrid-2-yl or pyrid-4-yl or represents pyrid-3-yl which is optionally substituted in the 6-position by fluorine, chlorine, bromine, methyl, trifluoromethyl or trifluoromethoxy or represents pyridazin-3-yl which is optionally substituted in the 6-position by chlorine or methyl or represents pyrazin-3-yl or represents 2-chloropyrazin-5-yl or represents 1,3-thiazol-5-yl which is optionally substituted in the 2-position by chlorine or methyl, or A represents a pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl radical which is optionally substituted by fluorine, chlorine, bromine, cyano, nitro, $C_1$-$C_4$-alkyl (which is optionally substituted by fluorine and/or chlorine), $C_1$-$C_3$-alkylthio (which is optionally substituted by fluorine and/or chlorine) or $C_1$-$C_3$-alkylsulphonyl (which is optionally substituted by fluorine and/or chlorine), or A represents a radical

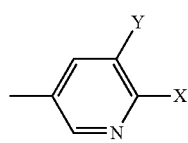

in which

X represents halogen, alkyl or haloalkyl,

Y represents halogen, alkyl, haloalkyl, haloalkoxy, azido or cyano and $R^1$ represents alkyl, haloalkyl, alkenyl, haloalkenyl, alkynyl, cycloalkyl, cycloalkylalkyl, halocycloalkyl, alkoxy, alkoxyalkyl or halocycloalkylalkyl, have insecticidal action (cf. EP 0 539 588, WO 2007/115643 A1, WO 2007/115644 A1 and WO 2007/115646 A1).

Furthermore, it is already known that numerous triazole derivatives, aniline derivatives, dicarboximides and other heterocycles can be used for controlling fungi (cf. EP-A 0 040 345, DE-A 22 01 063, DE-A 23 24 010, Pesticide Manual, 9th edition (1991), pages 249 and 827, EP-A 0 382 375, EP-A 0 515 901, DE-B2 2732257). However, the activity of these compounds is not always sufficient at low application rates.

Furthermore, it is already known that 1-(3,5-dimethylisoxazole-4-sulphonyl)-2-chloro-6,6-difluoro-[1,3]-dioxolo-[4,5f]-benzimidazole has fungicidal properties (cf. WO 97/06171).

Finally, it is also known that substituted halopyrimidines have fungicidal properties (cf. DE-A1-196 46 407, EP-B-712 396).

It has now been found that active compound combinations of at least one compound of the formula (I), with the proviso that 4-{[(6-chloropyrid-3-yl)methyl](methyl)amino}furan-2(5H)-one and 4-{[(6-chloropyrid-3-yl)methyl](cyclopropyl)amino}furan-2(5H)-one are excluded, and at least one active compound selected from groups (2) to (27) listed below are synergistically active and have very good insecticidal and fungicidal properties.

Group (2) Strobilurins of the General Formula (II)

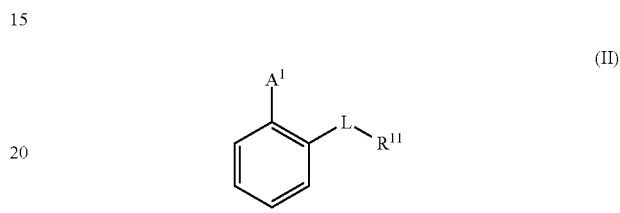

in which $A^1$ represents one of the groups

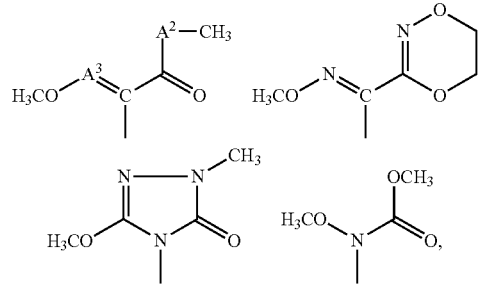

$A^2$ represents NH or O, $A^3$ represents N or CH,

L represents one of the groups

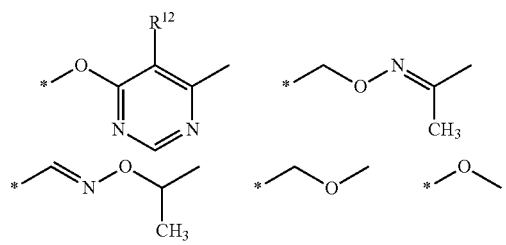

where the bond marked with an asterisk (*) is attached to the phenyl ring, $R^{11}$ represents phenyl, phenoxy or pyridinyl, each of which is optionally mono- or disubstituted by identical or different substituents from the group consisting of chlorine, cyano, methyl and trifluoromethyl, or represents 1-(4-chlorophenyl)pyrazol-3-yl or represents 1,2-propanedione bis(O-methyloxim)-1-yl, $R^{12}$ represents hydrogen or fluorine;

Group (3) Triazoles of the General Formula (III)

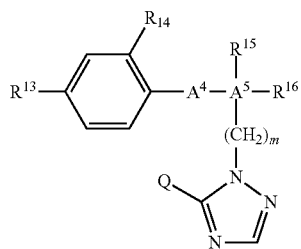

in which
Q represents hydrogen or SH,
m represents 0 or 1,
$R^{13}$ represents hydrogen, fluorine, chlorine, phenyl or 4-chlorophenoxy,
$R^{14}$ represents hydrogen or chlorine,
$A^4$ represents a direct bond, —$CH_2$—, —$(CH_2)_2$—, —O—, represents *—$CH_2$—$CHR^{17}$— or *—CH=$CR^{17}$—, where the bond marked * is attached to the phenyl ring, and $R^{15}$ and $R^{17}$ then together represent —$CH_2$—$CH_2$—CH[CH$(CH_3)_2$]— or —$CH_2$—$CH_2$—C$(CH_3)_2$—,
$A^5$ represents C or Si (silicon),
$A^4$ furthermore represents —$N(R^{17})$— and $A^5$ furthermore together with $R^{15}$ and $R^{16}$ represents the group C=N—$R^{18}$, where $R^{17}$ and $R^{18}$ then together represent the group

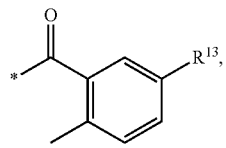

where the bond marked * is attached to $R^{17}$,
$R^{15}$ represents hydrogen, hydroxyl or cyano,
$R^{16}$ represents 1-cyclopropylethyl, 1-chlorocyclopropyl, $C_1$-$C_4$-alkyl, $C_1$-$C_6$-hydroxyalkyl, $C_1$-$C_4$-alkylcarbonyl, $C_1$-$C_2$-haloalkoxy-$C_1$-$C_2$-alkyl, trimethylsilyl-$C_1$-$C_2$-alkyl, monofluorophenyl, or phenyl,
$R^{15}$ and $R^{16}$ furthermore together represent —O—$CH_2$—CH$(R^{18})$—O—, —O—$CH_2$—CH$(R^{18})$—$CH_2$—, or —O—CH-(2-chlorophenyl)-,
$R^{18}$ represents hydrogen, $C_1$-$C_4$-alkyl or bromine;

Group (4) Sulfenamides of the General Formula (IV)

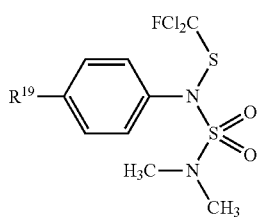

in which $R^{19}$ represents hydrogen or methyl;
Group (5) Valinamides Selected from the Group Consisting of
(5-1) iprovalicarb
(5-2) $N^1$-[2-(4-{[3-(4-chlorophenyl)-2-propynyl]oxy}-3-methoxyphenyl)ethyl]-$N^2$-(methylsulphonyl)-D-valinamide
(5-3) benthiavalicarb
(5-4) valiphenal Group (6) Carboxamides of the General Formula (V)

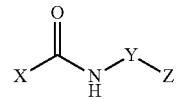

in which
X represents 2-chloro-3-pyridinyl, represents 1-methylpyrazol-4-yl which is substituted in the 3-position by methyl, trifluoromethyl or difluoroethyl and in the 5-position by hydrogen or chlorine, represents 4-ethyl-2-ethylamino-1,3-thiazol-5-yl, represents 1-methylcyclohexyl, represents 2,2-dichloro-1-ethyl-3-methylcyclopropyl, represents 2-fluoro-2-propyl, 3,4-dichloroisothiazol-5-yl, 5,6-dihydro-2-methyl-1,4-oxathiin-3-yl, 4-methyl-1,2,3-thiadiazol-5-yl, 4,5-dimethyl-2-trimethylsilylthiophen-3-yl, 1-methylpyrrol-3-yl which is substituted in the 4-position by methyl or trifluoromethyl and in the 5-position by hydrogen or chlorine, or represents phenyl which is mono- to trisubstituted by identical or different substituents from the group consisting of chlorine, methyl or trifluoromethyl,
Y represents a direct bond, optionally chlorine-, cyano- or oxo-substituted $C_1$-$C_6$-alkanediyl (alkylene), represents $C_2$-$C_6$-alkenediyl (alkenylene) or thiophendiyl,
Z represents hydrogen, $C_1$-$C_6$-alkyl or the group

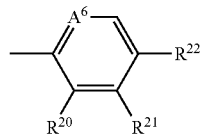

in which
$A^6$ represents CH or N,
$R^{20}$ represents hydrogen, chlorine, cyano, $C_1$-$C_6$-alkyl, represents phenyl which is optionally mono- or disubstituted by identical or different substituents from the group consisting of chlorine and di($C_1$-$C_3$-alkyl)aminocarbonyl or represents a radical from the group consisting of

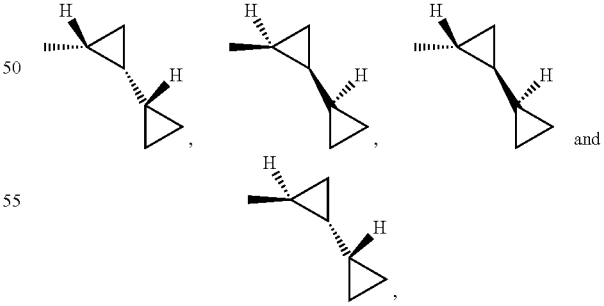

$R^{21}$ represents hydrogen, chlorine or isopropoxy,
$R^{22}$ represents hydrogen, chlorine, hydroxyl, methyl, trifluoromethyl or di($C_1$-$C_3$-alkyl)aminocarbonyl,
$R^{20}$ and $R^{21}$ furthermore together represent *—CH$(CH_3)$—$CH_2$—C$(CH_3)_2$— or *—CH$(CH_3)$—O—C$(CH_3)_2$—, where the bond marked * is attached to $R^{20}$ or represents a radical from the group consisting of

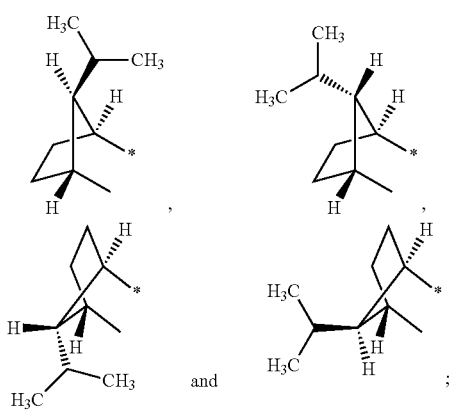

Group (7) Dithiocarbamates Selected from the Group Consisting of
(7-1) mancozeb
(7-2) maneb
(7-3) metiram
(7-4) propineb
(7-5) thiram
(7-6) zineb
(7-7) ziram Group (8) Acylalanines of the General Formula (VI)

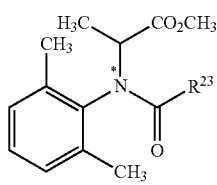

in which
* denotes a carbon atom in the (R) or the (S) configuration, preferably in the (S) configuration,
$R^{23}$ represents benzyl, furyl or methoxymethyl;

Group (9): Anilinopyrimidines of the General Formula (VII)

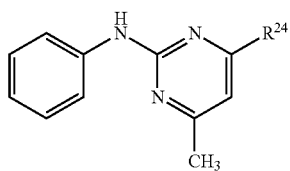

in which
$R^{24}$ represents methyl, cyclopropyl or 1-propynyl;

Group (10): Benzimidazoles of the General Formula (VIII)

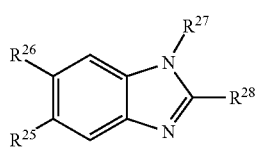

in which
$R^{25}$ and $R^{26}$ each represent hydrogen or together represent —O—$CF_2$—O—,
$R^{27}$ represents hydrogen, $C_1$-$C_4$-alkylaminocarbonyl or represents 3,5-dimethylisoxazol-4-ylsulphonyl,
$R^{28}$ represents chlorine, methoxycarbonylamino, chlorophenyl, furyl or thiazolyl;

Group (11): Carbamates of the General Formula (IX)

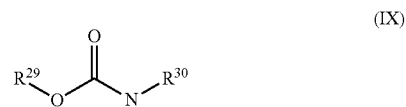

in which
$R^{29}$ represents n- or isopropyl,
$R^{30}$ represents di($C_1$-$C_2$-alkyl)amino-$C_2$-$C_4$-alkyl or diethoxyphenyl,
salts of these compounds also being included;
and also the carbamate pyribencarb.

Group (12): Dicarboximides Selected from the Group Consisting of
(12-1) captafol
(12-2) captan
(12-3) folpet
(12-4) iprodione
(12-5) procymidone
(12-6) vinclozolin Group (13): Guanidines Selected from the Group Consisting of
(13-1) dodine
(13-2) guazatine
(13-3) iminoctadine triacetate
(13-4) iminoctadine tris(albesilate)

Group (14): Imidazoles Selected from the Group Consisting of
(14-1) cyazofamid
(14-2) prochloraz
(14-3) triazoxide
(14-4) pefurazoate
(14-5) fenamidone Group (15): Morpholines of the General Formula (X)

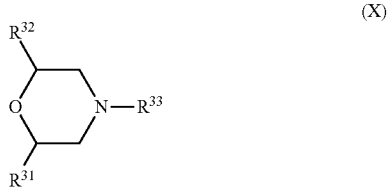

in which
$R^{31}$ and $R^{32}$ independently of one another represent hydrogen or methyl,
$R^{33}$ represents $C_1$-$C_{14}$-alkyl (preferably $C_{12}$-$C_{14}$-alkyl), $C_5$-$C_{12}$-cycloalkyl (preferably $C_{10}$-$C_{12}$-cycloalkyl), phenyl-$C_1$-$C_4$-alkyl which may be substituted in the phenyl moiety by halogen or $C_1$-$C_4$-alkyl or represents acrylyl which is substituted by chlorophenyl and dimethoxyphenyl;

Group (16): Pyrroles of the General Formula (XI)

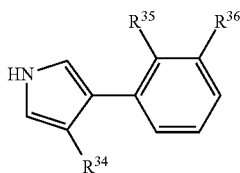

in which
R³⁴ represents chlorine or cyano,
R³⁵ represents chlorine or nitro,
R³⁶ represents chlorine,
R³⁵ and R³⁶ furthermore together represent —O—CF$_2$—O—;

Group (17): (Thio)Phosphonates Selected from the Group Consisting of
(17-1) fosetyl-Al,
(17-2) phosphonic acid,
(17-3) tolclophos-methyl;

Group (18): Phenylethanamides of the General Formula (XII)

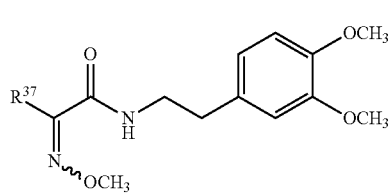

in which
R³⁷ represents unsubstituted or fluorine-, chlorine-, bromine-, methyl- or ethyl-substituted phenyl, 2-naphthyl, 1,2,3,4-tetrahydronaphthyl or indanyl;

Group (19): Fungicides Selected from the Group Consisting of
(19-1) acibenzolar-S-methyl
(19-2) chlorothalonil
(19-3) cymoxanil
(19-4) edifenphos
(19-5) famoxadone
(19-6) fluazinam
(19-7) copper oxychloride
(19-8) copper hydroxide
(19-9) oxadixyl
(19-10) spiroxamine
(19-11) dithianon
(19-12) metrafenone
(19-14) 2,3-dibutyl-6-chlorothieno[2,3-d]pyrimidin-4(3H)one
(19-15) probenazole
(19-16) isoprothiolane
(19-17) kasugamycin
(19-18) phthalide
(19-19) ferimzone
(19-20) tricyclazole
(19-21) cyprosulfamide
(19-22) mandipropamid
(19-23) quinoxyfen (known from EP-A 326 330) of the formula

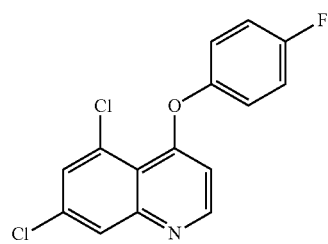 [SMILES: Fc1ccc(Oc2ccnc3cc(Cl)cc(Cl)c23)cc1]

(19-24) proquinazid (known from WO 94/26722) of the formula

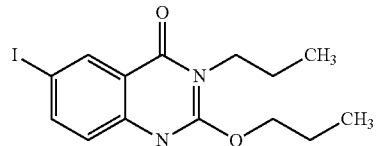

Group (20): (Thio)Urea Derivatives Selected from the Group Consisting of
(20-1) pencycuron
(20-2) thiophanate-methyl
(20-3) thiophanate-ethyl Group (21): Amides of the General Formula (XIII)

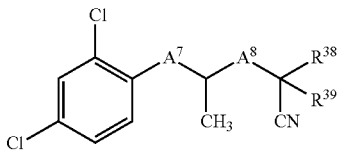

in which
A⁷ represents a direct bond or —O—,
A⁸ represents —C(═O)NH— or —NHC(═O)—,
R³⁸ represents hydrogen or $C_1$-$C_4$-alkyl,
R³⁹ represents $C_1$-$C_6$-alkyl;

Group (22): Triazolopyrimidines of the General Formula (XIV)

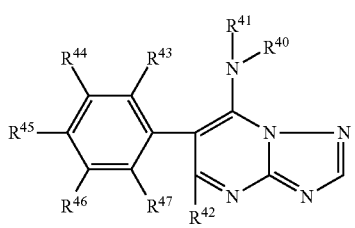

in which
R⁴⁰ represents $C_1$-$C_6$-alkyl or $C_2$-$C_6$-alkenyl,
R⁴¹ represents $C_1$-$C_6$-alkyl;
R⁴⁰ and R⁴¹ furthermore together represent $C_4$-$C_5$-alkanediyl (alkylene) which is mono- or disubstituted by $C_1$-$C_6$-alkyl,
R⁴² represents bromine or chlorine,
R⁴³ and R⁴⁷ independently of one another represent hydrogen, fluorine, chlorine or methyl, $R^{44}$ and $R^{46}$ independently of one another represent hydrogen or fluorine, $R^{45}$ represents hydrogen, fluorine or methyl, Group (23): Iodochromones of the General Formula (XV)

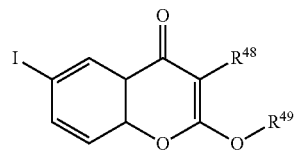

(XV)

in which $R^{48}$ represents $C_1$-$C_6$-alkyl;

$R^{49}$ represents $C_1$-$C_6$-alkyl, $C_2$-$C_6$-alkenyl or $C_2$-$C_6$-alkynyl;

Group (24): Biphenylcarboxamides of the General Formula (XVI)

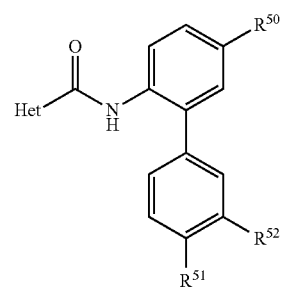

(XVI)

in which $R^{50}$ represents hydrogen or fluorine;

$R^{51}$ represents fluorine, chlorine, bromine, methyl, trifluoromethyl, trifluoromethoxy, —CH=N—OMe or C(Me)=N—OMe, $R^{52}$ represents hydrogen, fluorine, chlorine, bromine, methyl or trifluoromethyl, Het represents one of the radicals Het1 to Het7 below:

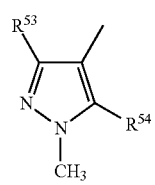

Het1

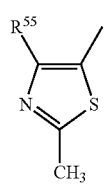

Het2

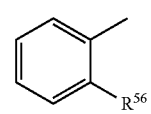

Het3

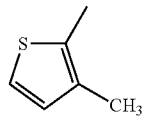

Het4

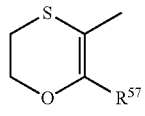

Het5

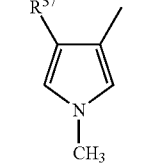

Het6

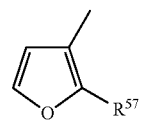

Het7

$R^{53}$ represents iodine, methyl, difluoromethyl or trifluoromethyl, $R^{54}$ represents hydrogen, fluorine, chlorine or methyl, $R^{55}$ represents methyl, difluoromethyl or trifluoromethyl, $R^{56}$ represents chlorine, bromine, iodine, methyl, difluoromethyl or trifluoromethyl, $R^{57}$ represents methyl or trifluoromethyl.

Group (25): Sulphonamides
 (25-1) amisulbrom
Group (26): Thiazolidines
 (26-1) flutianil
Group (27): Dinitrophenols
 (27-1) meptyldinocap Surprisingly, the fungicidal action of the active compound combinations according to the invention considerably exceeds the total of the actions of the individual active compounds. A true synergistic effect which could not have been predicted therefore exists, not just a complementation of action.

Surprisingly, the insecticidal action of the active compound combinations according to the invention likewise considerably exceeds the total of the actions of the individual active compounds. A true synergistic effect which could not have been predicted therefore exists, not just a complementation of action.

The active compound combinations according to the invention comprise, in addition to at least one compound of the formula (I), at least one active compound of groups (2) to (27) above. The active compound combinations according to the invention preferably comprise exactly one compound of the formula (I) and exactly one active compound of groups (2) to (27) above. Preference is furthermore given to active compound combinations comprising one compound of the formula (I) and two active compounds of groups (2) to (27) above. Preference is furthermore given to active compound combinations comprising two compounds of the formula (I) and one active compound of groups (2) to (27) above.

Preferred sub-groups of the compounds of the formula (I) mentioned above in the active compound combinations according to the invention with at least one active compound of the above-listed groups (2) to (27) are listed below, with the proviso that 4-{[(6-chloropyrid-3-yl)methyl](methyl) amino}furan-2(5H)-one and 4-{[(6-chloropyrid-3-yl)methyl](cyclopropyl)amino}furan-2(5H)-one are excluded.

A preferably represents 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl, 2-chloropyrimidin-5-yl, 2-trifluoromethylpyrimidin-5-yl, 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromo-pyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl or 5-difluoromethyl-6-iodopyrid-3-yl.

$R^1$ preferably represents optionally fluorine-substituted $C_1$-$C_5$-alkyl, $C_2$-$C_5$-alkenyl, $C_3$-$C_5$-cycloalkyl, $C_3$-$C_5$-cycloalkylalkyl or $C_1$-$C_5$-alkoxy.

A particularly preferably represents the 6-fluoropyrid-3-yl, 6-chloropyrid-3-yl, 6-bromopyrid-3-yl, 6-chloro-1,4-pyridazin-3-yl, 2-chloro-1,3-thiazol-5-yl, 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl or 5-difluoromethyl-6-chloropyrid-3-yl radical.

$R^1$ particularly preferably represents methyl, methoxy, ethyl, propyl, vinyl, allyl, propargyl, cyclopropyl, 2-fluoroethyl, 2,2-difluoroethyl or 2-fluorocyclopropyl.

A very particularly preferably represents the 6-fluoropyrid-3-yl, 6-chloropyrid-3-yl, 6-bromopyrid-3-yl, 5-fluoro-6-chloropyrid-3-yl, 2-chloro-1,3-thiazol-5-yl or 5,6-dichloropyrid-3-yl radical.

$R^1$ very particularly preferably represents methyl, cyclopropyl, methoxy, 2-fluoroethyl or 2,2-difluoroethyl.

A most preferably represents the 6-chloropyrid-3-yl or 5-fluoro-6-chloropyrid-3-yl radical.

$R^1$ most preferably represents methyl, 2-fluoroethyl or 2,2-difluoroethyl.

In a special group of compounds of the formula (I), A represents 6-chloropyrid-3-yl.

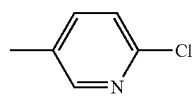

In a further special group of compounds of the formula (I), A represents 6-bromopyrid-3-yl.

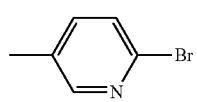

In a further special group of compounds of the formula (I), A represents 6-chloro-1,4-pyridazin-3-yl.

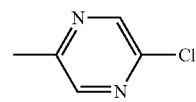

In a further special group of compounds of the formula (I), A represents 2-chloro-1,3-thiazol-5-yl.

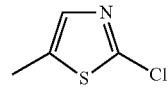

In a further special group of compounds of the formula (I), A represents 5-fluoro-6-chloropyrid-3-yl.

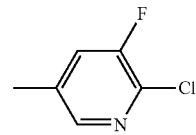

In a further special group of compounds of the formula (I), A represents 5-fluoro-6-bromopyrid-3-yl.

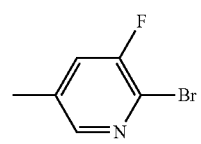

In a further special group of compounds of the formula (I), A represents 5,6-dichloropyrid-3-yl.

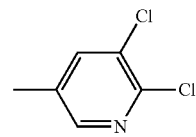

In a further special group of compounds of the formula (I), $R^1$ represents methyl.

In a further special group of compounds of the formula (I), $R^1$ represents ethyl.

In a further special group of compounds of the formula (I), $R^1$ represents cyclopropyl.

In a further special group of compounds of the formula (I), $R^1$ represents 2-fluoroethyl.

In a further special group of compounds of the formula (I), $R^1$ represents 2,2-difluoroethyl.

The abovementioned general or preferred radical definitions or illustrations can be combined with one another as desired, i.e. including combinations between the respective preferred ranges.

Preference according to the invention is given to compounds of the formula (I) which contain a combination of the meanings listed above as being preferred.

Particular preference according to the invention is given to compounds of the formula (I) which contain a combination of the meanings listed above as being particularly preferred.

Very particular preference according to the invention is given to compounds of the formula (I) which contain a combination of the meanings listed above as being very particularly preferred.

A preferred sub-group of the compounds of the formula (I) are those of the formula (I-a)

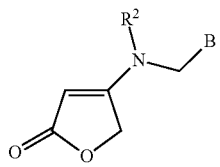

(I-a)

in which

B represents pyrid-2-yl or pyrid-4-yl or represents pyrid-3-yl which is optionally substituted in the 6-position by fluorine, chlorine, bromine, methyl, trifluoromethyl or trifluoromethoxy or represents pyridazin-3-yl which is optionally substituted in the 6-position by chlorine, or methyl or represents pyrazin-3-yl or represents 2-chloropyrazin-5-yl or represents 1,3-thiazol-5-yl which is optionally substituted in the 2-position by chlorine or methyl, $R^2$ represents haloalkyl, haloalkenyl, halocycloalkyl or halocycloalkylalkyl.

Preferred substituents or ranges of the radicals mentioned in the formula (I-a) shown above and below are illustrated below:

B preferably represents 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl.

$R^2$ preferably represents fluorine-substituted $C_1$-$C_5$-alkyl, $C_2$-$C_5$-alkenyl, $C_3$-$C_5$-cycloalkyl or $C_3$-$C_5$-cycloalkylalkyl.

B particularly preferably represents the 6-fluoropyrid-3-yl, 6-chloropyrid-3-yl, 6-bromopyrid-3-yl, 6-chloro-1,4-pyridazin-3-yl, 2-chloro-1,3-thiazol-5-yl radical.

$R^2$ particularly preferably represents 2-fluoroethyl, 2,2-difluoroethyl, 2-fluorocyclopropyl.

B very particularly preferably represents the 6-chloropyrid-3-yl radical.

$R^2$ very particularly preferably represents 2-fluoroethyl or 2,2-difluoroethyl.

In a special group of compounds of the formula (I-a), B represents 6-chloropyrid-3-yl.

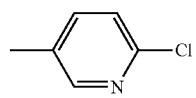

In a further special group of compounds of the formula (I-a), B represents 6-bromopyrid-3-yl.

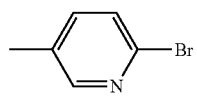

In a further special group of compounds of the formula (I-a), B represents 6-chloro-1,4-pyridazin-3-yl.

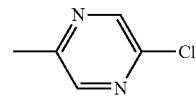

In a further special group of compounds of the formula (I-a), $R^2$ represents 2-fluoroethyl.

In a further special group of compounds of the formula (I-a), $R^2$ represents 2,2-difluoroethyl.

A further preferred sub-group of the compounds of the formula (I) are those of the formula (I-b)

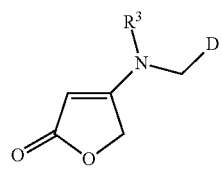

(I-b)

in which

D represents a radical

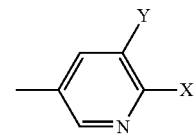

in which

X and Y have the meanings given above, $R^3$ represents hydrogen, alkyl, alkenyl, alkynyl, cycloalkyl or alkoxy.

Preferred substituents or ranges of the radicals mentioned in the formula (I-b) shown above and below are illustrated below:

D preferably represents one of the radicals 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl, 5-difluoromethyl-6-iodopyrid-3-yl.

$R^3$ preferably represents $C_1$-$C_4$-alkyl, $C_2$-$C_4$-alkenyl, $C_2$-$C_4$-alkynyl or $C_3$-$C_4$-cycloalkyl.

D particularly preferably represents 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl or 5-difluoromethyl-6-chloropyrid-3-yl.

$R^3$ particularly preferably represents $C_1$-$C_4$-alkyl.

D very particularly preferably represents 5-fluoro-6-chloropyrid-3-yl or 5-fluoro-6-bromopyrid-3-yl.

$R^3$ very particularly preferably represents methyl, ethyl, propyl, vinyl, allyl, propargyl or cyclopropyl.

D most preferably represents 5-fluoro-6-chloropyrid-3-yl.

$R^3$ most preferably represents methyl or cyclopropyl.

In a further special group of compounds of the formula (I-b), D represents 5-fluoro-6-chloropyrid-3-yl.

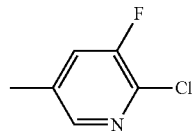

In a further special group of compounds of the formula (I-b), D represents 5,6-dichloropyrid-3-yl.

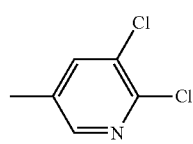

In a further special group of compounds of the formula (I-b), D represents 5-bromo-6-chloropyrid-3-yl.

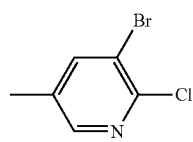

In a further special group of compounds of the formula (Lb), D represents 5-methyl-6-chloropyrid-3-yl.

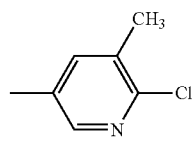

In a further special group of compounds of the formula (Lb), D represents 5-fluoro-6-bromopyrid-3-yl.

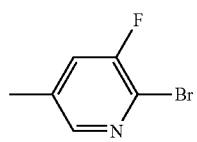

In a further special group of compounds of the formula (I-b), D represents 5-chloro-6-bromopyrid-3-yl.

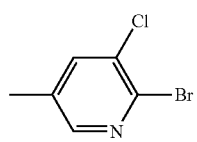

In a further special group of compounds of the formula (Lb), D represents 5-chloro-6-iodopyrid-3-yl.

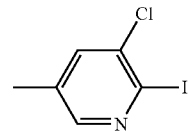

In a further special group of compounds of the formula (Lb), $R^3$ represents methyl.

In a further special group of compounds of the formula (Lb), $R^3$ represents ethyl.

In a further special group of compounds of the formula (Lb), $R^3$ represents cyclopropyl.

A further preferred sub-group of the compounds of the formula (I) are those of the formula (I-c)

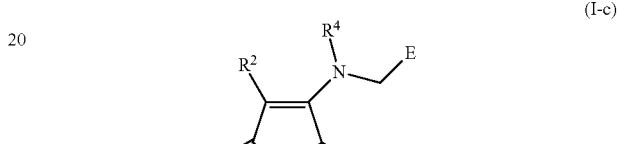

(I-c)

in which
E represents a radical

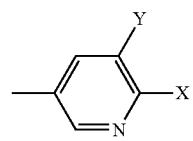

in which
X and Y have the meanings given above and
$R^4$ represents haloalkyl, haloalkenyl, halocycloalkyl or halocycloalkylalkyl.

Preferred substituents or ranges of the radicals mentioned in the formula (I-c) shown above and below are illustrated below:

E preferably represents one of the radicals 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl, 5-difluoromethyl-6-iodopyrid-3-yl.

$R^4$ preferably represents fluorine-substituted $C_1$-$C_5$-alkyl, $C_2$-$C_5$-alkenyl, $C_3$-$C_5$-cycloalkyl or $C_3$-$C_5$-cycloalkylalkyl.

E particularly preferably represents 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl or 5-difluoromethyl-6-chloropyrid-3-yl.

$R^4$ particularly preferably represents 2-fluoroethyl, 2,2-difluoroethyl, 2-fluorocyclopropyl.

E very particularly preferably represents 5-fluoro-6-chloropyrid-3-yl.

R⁴ very particularly preferably represents 2-fluoroethyl or 2,2-difluoroethyl.

In a further special group of compounds of the formula (I-c), E represents 5-fluoro-6-chloropyrid-3-yl.

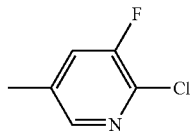

In a further special group of compounds of the formula (I-c), E represents 5,6-dichloropyrid-3-yl.

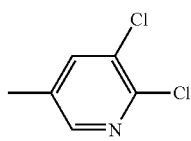

In a further special group of compounds of the formula (I-c), E represents 5-bromo-6-chloropyrid-3-yl.

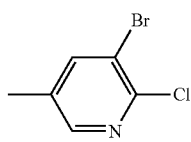

In a further special group of compounds of the formula (I-c), E represents 5-methyl-6-chloropyrid-3-yl.

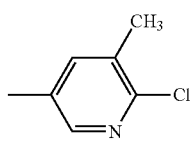

In a further special group of compounds of the formula (I-c), E represents 5-fluoro-6-bromopyrid-3-yl.

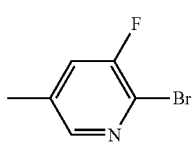

In a further special group of compounds of the formula (I-c), E represents 5-chloro-6-bromopyrid-3-yl.

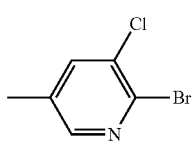

In a further special group of compounds of the formula (I-c), E represents 5-chloro-6-iodopyrid-3-yl.

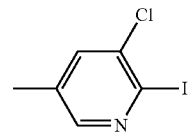

In a further special group of compounds of the formula (I-c), R⁴ represents 2-fluoroethyl.

In a further special group of compounds of the formula (I-c), R⁴ represents 2,2-difluoroethyl.

A preferred sub-group of the compounds of the formula (I) are those of the formula (I-d)

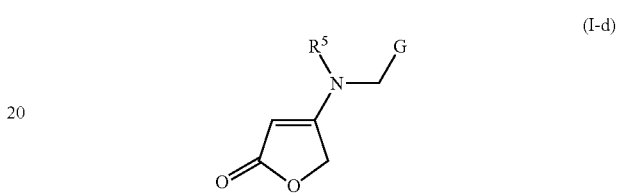

(I-d)

in which

G represents pyrid-2-yl or pyrid-4-yl or represents pyrid-3-yl which is optionally substituted in the 6-position by fluorine, chlorine, bromine, methyl, trifluoromethyl or trifluoromethoxy or represents pyridazin-3-yl which is optionally substituted in the 6-position by chlorine or methyl or represents pyrazin-3-yl or represents 2-chloropyrazin-5-yl or represents 1,3-thiazol-5-yl which is optionally substituted in the 2-position by chlorine or methyl, and R⁵ represents $C_1$-$C_4$-alkyl, $C_2$-$C_4$ alkenyl, $C_2$-$C_4$ alkynyl, $C_3$-$C_4$ cycloalkyl or $C_1$-$C_4$-alkoxy, with the proviso that 4-{[(6-chloropyrid-3-yl)methyl](methyl)amino}furan-2(5H)-one and 4-{[(6-chloropyrid-3-yl)methyl](cyclopropyl)amino}furan-2(5H)-one are excluded.

Preferred substituents or ranges of the radicals mentioned in the formula (I-d) shown above and below are illustrated below:

G preferably represents 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl.

R⁵ preferably represents $C_1$-$C_4$-alkyl, $C_1$-alkoxy, $C_2$-$C_4$-alkenyl, $C_2$-$C_4$-alkynyl or $C_3$-$C_4$-cycloalkyl.

G particularly preferably represents the 6-fluoropyrid-3-yl, 6-chloropyrid-3-yl, 6-bromopyrid-3-yl, 6-chloro-1,4-pyridazin-3-yl, 2-chloro-1,3-thiazol-5-yl radical.

R⁵ particularly preferably represents methyl, methoxy, ethyl, propyl, vinyl, allyl, propargyl or cyclopropyl.

G very particularly preferably represents the 6-chloropyrid-3-yl radical.

R⁵ very particularly preferably represents methyl or cyclopropyl.

In a special group of compounds of the formula (I-d), G represents 6-chloropyrid-3-yl.

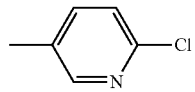

In a further special group of compounds of the formula (I-d), G represents 6-bromopyrid-3-yl.

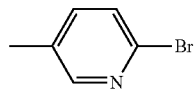

In a further special group of compounds of the formula (I-d), G represents 6-chloro-1,4-pyridazin-3-yl.

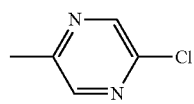

In a further special group of compounds of the formula (I-d), G represents 2-chloro-1,3-thiazol-5-yl.

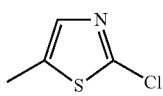

In a further special group of compounds of the formula (I-d), G represents 6-fluoropyrid-3-yl.

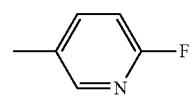

In a further special group of compounds of the formula (I-d), G represents 6-trifluoromethylpyrid-3-yl.

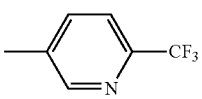

In a further special group of compounds of the formula (I-d), G represents 6-fluoropyrid-3-yl.

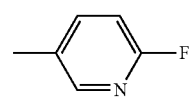

In a further special group of compounds of the formula (I-d), $R^5$ represents methyl.

In a further special group of compounds of the formula (I-d), $R^5$ represents cyclopropyl.

Specific mention may be made of the following compounds of the general formula (I):

compound (I-1), 4-{[(6-bromopyrid-3-yl)methyl](2-fluoroethyl)amino}furan-2(5H)-one, has the formula

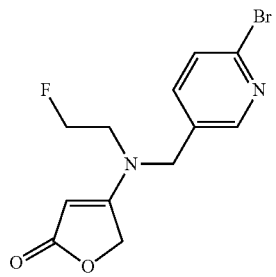 [SMILES: O=C1C=C(N(CCF)Cc2ccc(Br)nc2)CO1]

and is known from WO 2007/115644 A1.

Compound (I-2), 4-{[(6-fluoropyrid-3-yl)methyl](2,2-difluoroethyl)amino}furan-2(5H)-one, has the formula

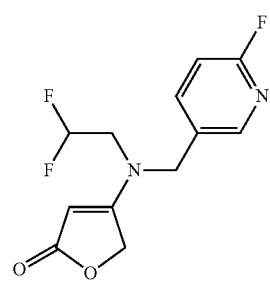 [SMILES: O=C1C=C(N(Cc2ccc(F)nc2)CC(F)F)CO1]

and is known from WO 2007/115644 A1.

Compound (I-3), 4-{[(2-chloro-1,3-thiazol-5-yl)methyl](2-fluoroethyl)amino}furan-2(5H)-one, has the formula

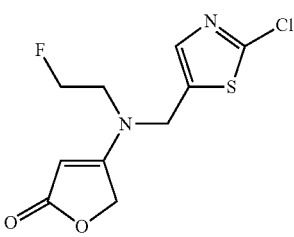 [SMILES: O=C1C=C(N(CCF)Cc2cnc(Cl)s2)CO1]

and is known from WO 2007/115644 A1.

Compound (I-4), 4-{[(6-chloropyrid-3-yl)methyl](2-fluoroethyl)amino}furan-2(5H)-one, has the formula

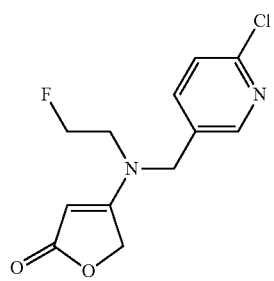 [SMILES: O=C1C=C(N(CCF)Cc2ccc(Cl)nc2)CO1]

and is known from WO 2007/115644 A1.

Compound (I-5), 4-{[(6-chloropyrid-3-yl)methyl](2,2-difluoroethyl)amino}furan-2(5H)-one, has the formula

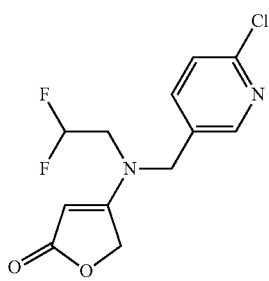 [SMILES: O=C1C=C(N(Cc2ccc(Cl)nc2)CC(F)F)CO1]

and is known from WO 2007/115644 A1.

Compound (I-6), 4-{[(6-chloro-5-fluorpyrid-3-yl)methyl](methyl)amino}furan-2(5H)-one, has the formula

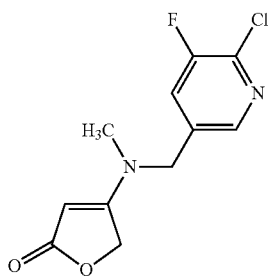 [SMILES: CN(Cc1cnc(Cl)c(F)c1)C1=CC(=O)OC1]

and is known from WO 2007/115643 A1.

Compound (I-7), 4-{[(5,6-dichloropyrid-3-yl)methyl](2-fluoroethyl)amino}furan-2(5H)-one, has the formula

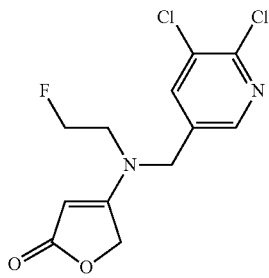 [SMILES: O=C1C=C(N(CCF)Cc2cnc(Cl)c(Cl)c2)CO1]

and is known from WO 2007/115646 A1.

Compound (I-8), 4-{[(6-chloro-5-fluoropyrid-3-yl)methyl](cyclopropyl)amino}furan-2(5H)-one, has the formula

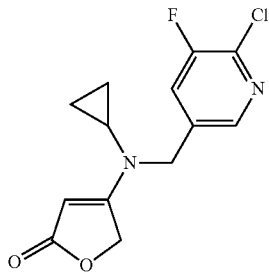 [SMILES: O=C1C=C(N(Cc2cnc(Cl)c(F)c2)C2CC2)CO1]

and is known from WO 2007/115643 A1.

The formula (II) comprises the following preferred combination partners of group (2):

(2-1) azoxystrobin (known from EP-A 0 382 375) of the formula

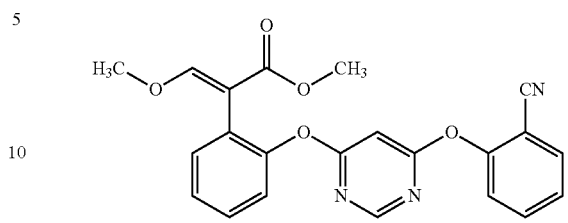

(2-2) fluoxastrobin (known from DE-A 196 02 095) of the formula

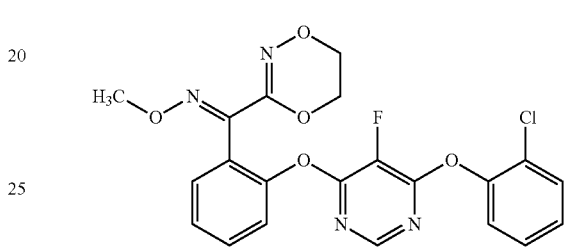

(2-3) (2E)-2-(2-{[6-(3-chloro-2-methylphenoxy)-5-fluoro-4-pyrimidinyl]oxy}phenyl)-2-(methoxyimino)-N-methylethanamide (known from DE-A 196 46 407, EP-B 0 712 396) of the formula

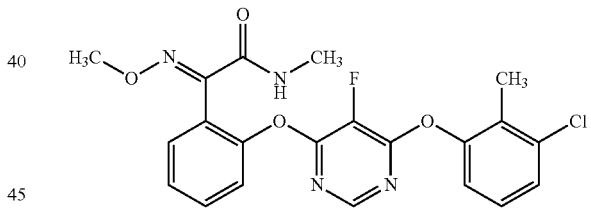

(2-4) trifloxystrobin (known from EP-A 0 460 575) of the formula

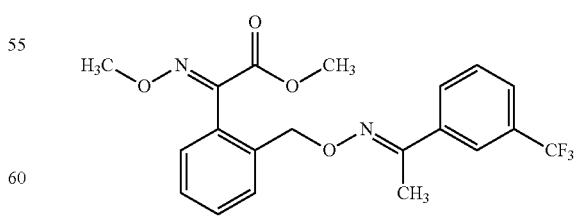

(2-5) (2E)-2-(methoxyimino)-N-methyl-2-(2-{[({(1E)-1-[3-(trifluoromethyl)phenyl]ethylidene}amino)oxy]methyl}phenyl)ethanamide (known from EP-A 0 569 384) of the formula

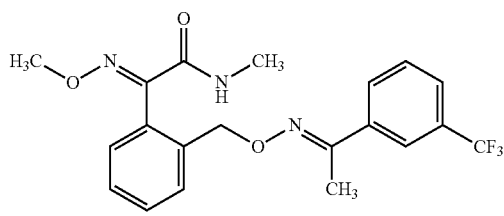 [SMILES: CNC(=O)/C(=N/OC)c1ccccc1CO/N=C(\C)c1cccc(C(F)(F)F)c1]

(2-6) (2E)-2-(methoxyimino)-N-methyl-2-{2-[(E)-({1-[3-(trifluoromethyl)phenyl]ethoxy}imino)methyl]phenyl}ethanamide (known from EP-A 0 596 254) of the formula

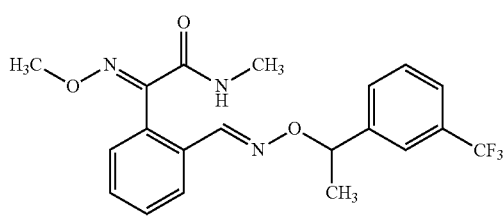 [SMILES: CNC(=O)/C(=N/OC)c1ccccc1/C=N/OC(C)c1cccc(C(F)(F)F)c1]

(2-7) orysastrobin (known from DE-A 195 39 324) of the formula

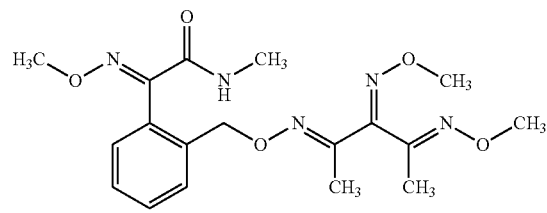

(2-8) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one (known from WO 98/23155) of the formula

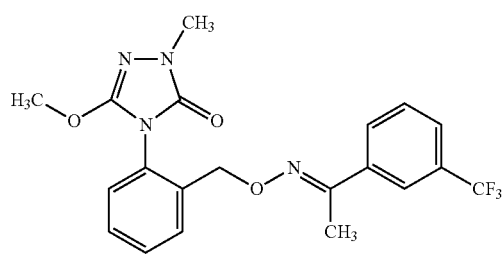 [SMILES: COc1nn(C)c(=O)n1-c1ccccc1CO/N=C(\C)c1cccc(C(F)(F)F)c1]

(2-9) kresoxim-methyl (known from EP-A 0 253 213) of the formula

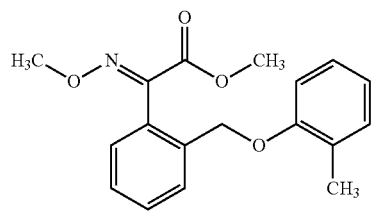 [SMILES: CO/N=C(/C(=O)OC)c1ccccc1COc1ccccc1C]

(2-10) dimoxystrobin (known from EP-A 0 398 692) of the formula

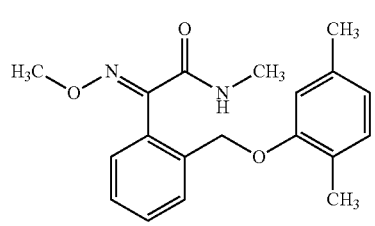 [SMILES: CNC(=O)/C(=N/OC)c1ccccc1COc1cc(C)ccc1C]

(2-11) picoxystrobin (known from EP-A 0 278 595) of the formula

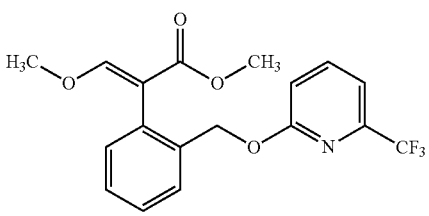 [SMILES: CO/C=C(/C(=O)OC)c1ccccc1COc1cccc(C(F)(F)F)n1]

(2-12) pyraclostrobin (known from DE-A 44 23 612) of the formula

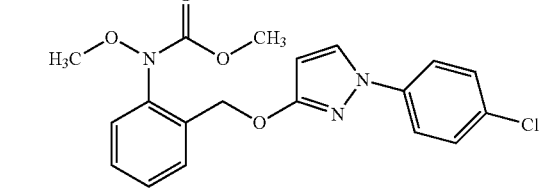

(2-13) metominostrobin (known from EP-A 0 398 692) of the formula

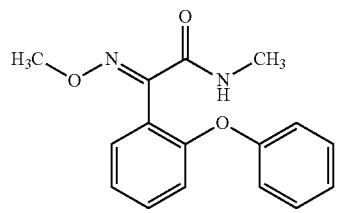 [SMILES: CNC(=O)/C(=N/OC)c1ccccc1Oc1ccccc1]

The formula (III) comprises the following preferred combination partners of group (3):

(3-1) azaconazole (known from DE-A 25 51 560) of the formula

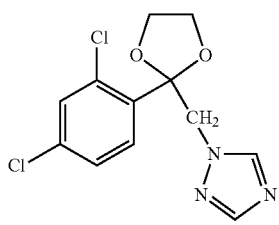 [SMILES: Clc1ccc(C2(Cn3cncn3)OCCO2)c(Cl)c1]
(3-2) etaconazole (known from DE-A 25 51 560) of the formula
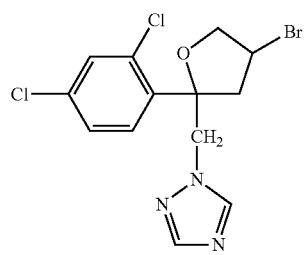
(3-6) cyproconazole (known from DE-A 34 06 993) of the formula
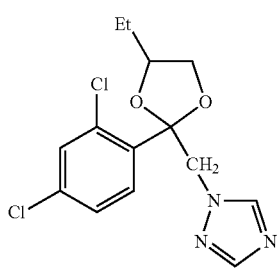 [SMILES: CCC1COC(Cn2cncn2)(c2ccc(Cl)cc2Cl)O1]
(3-3) propiconazole (known from DE-A 25 51 560) of the formula
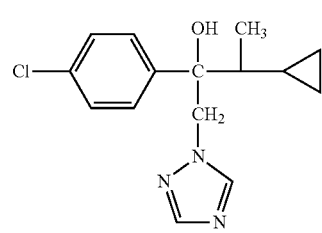
(3-7) hexaconazole (known from DE-A 30 42 303) of the formula
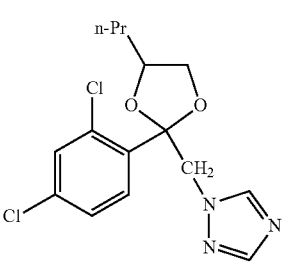
(3-4) difenoconazole (known from EP-A 0 112 284) of the formula
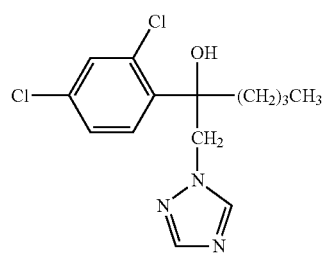
(3-8) penconazole (known from DE-A 27 35 872) of the formula
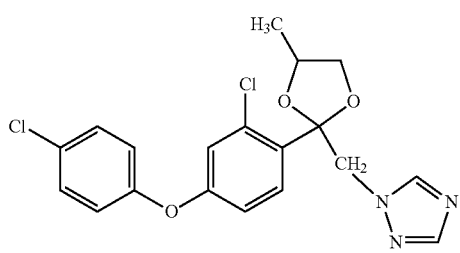 [SMILES: CC1COC(Cn2cncn2)(c2ccc(Oc3ccc(Cl)cc3)cc2Cl)O1]
(3-5) bromuconazole (known from EP-A 0 258 161) of the formula
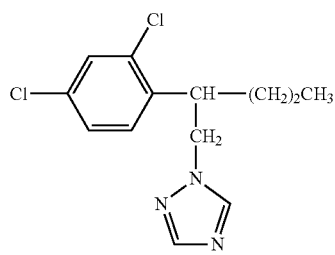
(3-9) myclobutanil (known from EP-A 0 145 294) of the formula

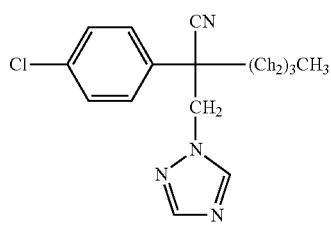

(3-10) tetraconazole (known from EP-A 0 234 242) of the formula

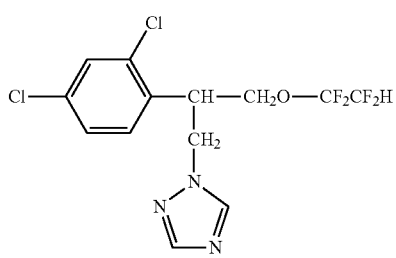

(3-11) flutriafol (known from EP-A 0 015 756) of the formula

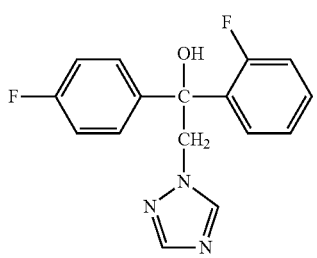 [SMILES: OC(Cn1cncn1)(c1ccc(F)cc1)c1ccccc1F]

(3-12) epoxiconazole (known from EP-A 0 196 038) of the formula

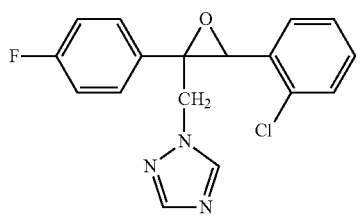 [SMILES: Fc1ccc(C2(Cn3cncn3)OC2c2ccccc2Cl)cc1]

(3-13) flusilazole (known from EP-A 0 068 813) of the formula

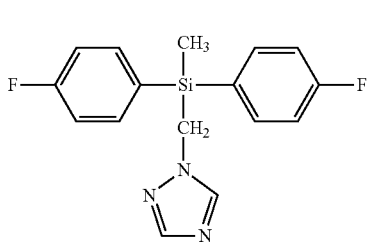 [SMILES: C[Si](Cn1cncn1)(c1ccc(F)cc1)c1ccc(F)cc1]

(3-14) simeconazole (known from EP-A 0 537 957) of the formula

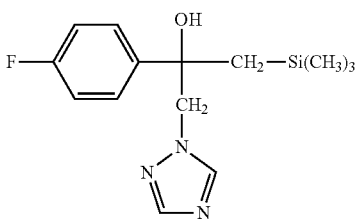

(3-15) prothioconazole (known from WO 96/16048) of the formula

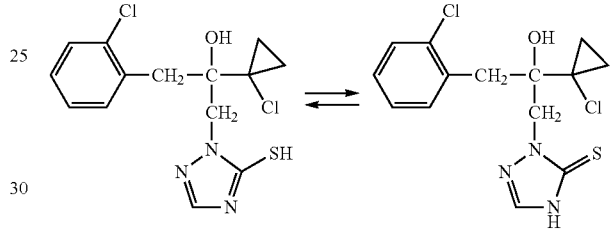

(3-16) fenbuconazole (known from DE-A 37 21 786) of the formula

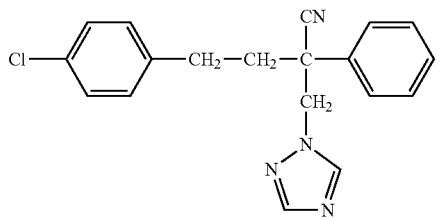 [SMILES: N#CC(CCc1ccc(Cl)cc1)(Cn1cncn1)c1ccccc1]

(3-17) tebuconazole (known from EP-A 0 040 345) of the formula

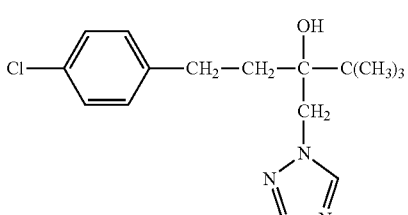

(3-18) ipconazole (known from EP-A 0 329 397) of the formula (3-19) metconazole (known from EP-A 0 329 397) of the formula (3-20) triticonazole (known from EP-A 0 378 953) of the formula (3-21) bitertanol (known from DE-A 23 24 010) of the formula (3-22) triadimenol (known from DE-A 23 24 010) of the formula (3-23) triadimefon (known from DE-A 22 01 063) of the formula (3-24) fluquinconazole (known from EP-A 0 183 458) of the formula (3-25) quinconazole (known from EP-A 0 183 458) of the formula The formula (IV) comprises the following preferred combination partners of group (4):

(4-1) dichlofluanid (known from DE-A 11 93 498) of the formula (4-2) tolylfluanid (known from DE-A 11 93 498) of the formula

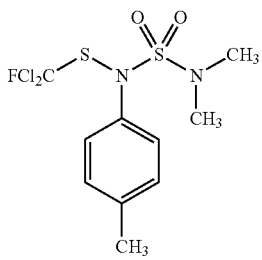

Preferred combination partners of group (5) are
(5-1) iprovalicarb (known from DE-A 40 26 966) of the formula

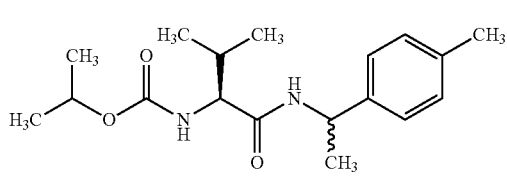 [SMILES: Cc1ccc(C(C)NC(=O)[C@@H](NC(=O)OC(C)C)C(C)C)cc1]

(5-3) benthiavalicarb (known from WO 96/04252) of the formula

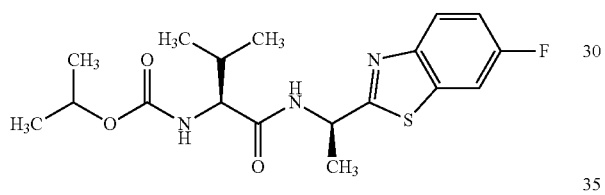

(5-4) valiphenal (known from EP1028125) of the formula

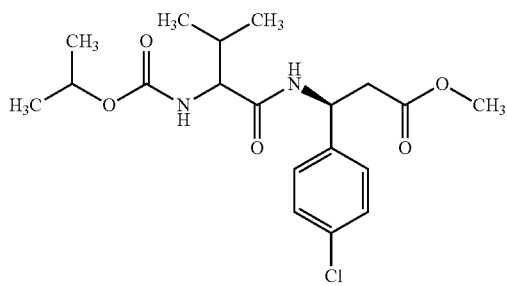 [SMILES: COC(=O)C[C@H](NC(=O)C(NC(=O)OC(C)C)C(C)C)c1ccc(Cl)cc1]

The formula (V) comprises the following preferred combination partners of group (6):
(6-1) 2-chloro-N-(1,1,3-trimethyl-indan-4-yl)-nicotinamide (known from EP-A 0 256 503) of the formula

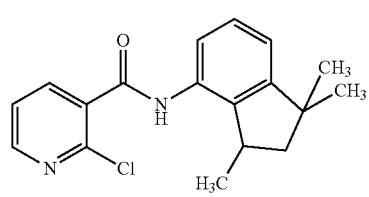 [SMILES: CC1CC(C)(C)c2cccc(NC(=O)c3cccnc3Cl)c21]

(6-2) boscalid (known from DE-A 195 31 813) of the formula (6-3) furametpyr (known from EP-A 0 315 502) of the formula

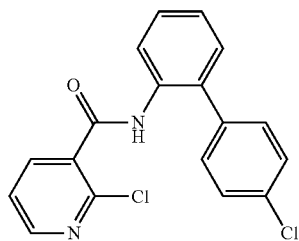 [SMILES: O=C(Nc1ccccc1-c1ccc(Cl)cc1)c1cccnc1Cl]

(6-4) N-(3-p-tolyl-thiophen-2-yl)-1-methyl-3-trifluoromethyl-1H-pyrazole-4-carboxamide (known from EP-A 0 737 682) of the formula

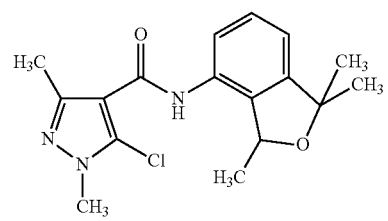

(6-5) ethaboxam (known from EP-A 0 639 574) of the formula

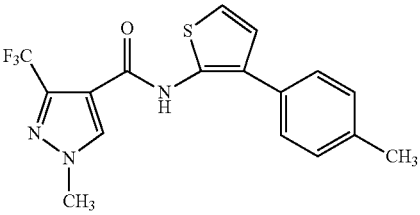 [SMILES: Cc1ccc(-c2ccsc2NC(=O)c2cn(C)nc2C(F)(F)F)cc1]

(6-6) fenhexamid (known from EP-A 0 339 418) of the formula

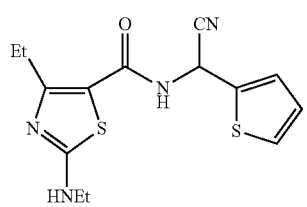

(6-7) carpropamid (known from EP-A 0 341 475) of the formula

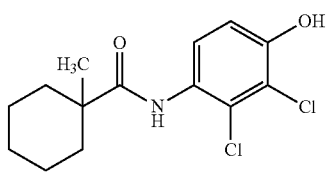 [SMILES: CC1(C(=O)Nc2ccc(O)c(Cl)c2Cl)CCCCC1]

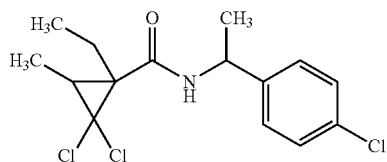 [SMILES: CCC1(C(=O)NC(C)c2ccc(Cl)cc2)C(C)C1(Cl)Cl]

(6-8) 2-chloro-4-(2-fluoro-2-methylpropionylamino)-N,N-dimethylbenzamide (known from EP-A 0 600 629) of the formula

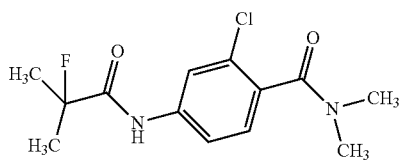 [SMILES: CN(C)C(=O)c1ccc(NC(=O)C(C)(C)F)cc1Cl]

(6-9) fluopicolid (known from WO 99/42447) of the formula

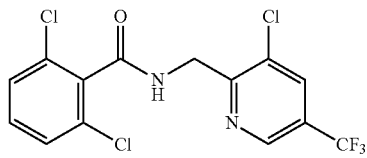 [SMILES: O=C(NCc1ncc(C(F)(F)F)cc1Cl)c1c(Cl)cccc1Cl]

(6-10) zoxamide (known from EP-A 0 604 019) of the formula

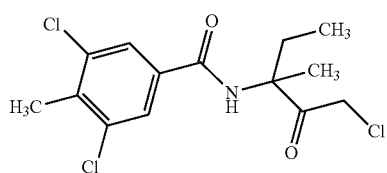 [SMILES: CCC(C)(NC(=O)c1cc(Cl)c(C)c(Cl)c1)C(=O)CCl]

(6-11) isotianil (ISO-proposed) (known from DE-A 19750012) of the formula

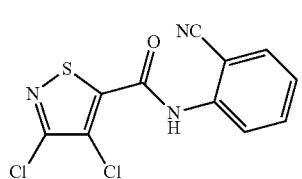 [SMILES: N#Cc1ccccc1NC(=O)c1snc(Cl)c1Cl]

(6-12) carboxin (known from U.S. Pat. No. 3,249,499) of the formula

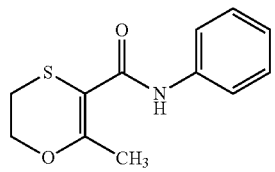 [SMILES: CC1=C(C(=O)Nc2ccccc2)SCCO1]

(6-13) tiadinil (known from U.S. Pat. No. 6,616,054) of the formula

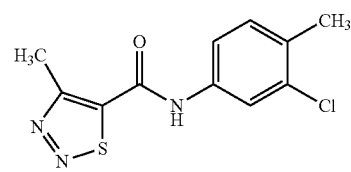 [SMILES: Cc1ccc(NC(=O)c2snnc2C)cc1Cl]

(6-14) penthiopyrad (known from EP-A 0 737 682) of the formula

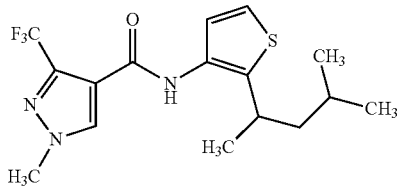 [SMILES: CC(C)CC(C)c1sccc1NC(=O)c1cn(C)nc1C(F)(F)F]

(6-15) silthiofam (known from WO 96/18631) of the formula

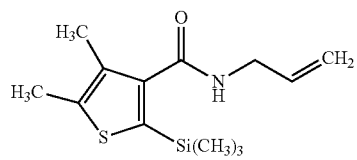

(6-16) N-[2-(1,3-dimethylbutyl)phenyl]-1-methyl-4-(trifluoromethyl)-1H-pyrrole-3-carboxamide (known from WO 02/38542) of the formula

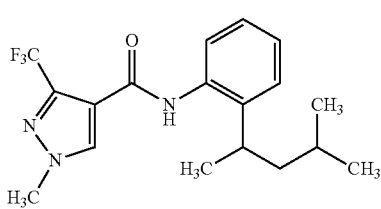 [SMILES: CC(C)CC(C)c1ccccc1NC(=O)c1cn(C)nc1C(F)(F)F]

(6-17) flutolanil (known from DE-A 27 31 522) of the formula

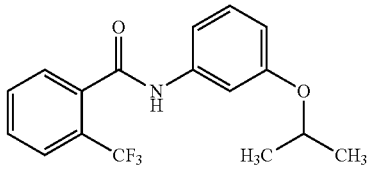 [SMILES: CC(C)Oc1cccc(NC(=O)c2ccccc2C(F)(F)F)c1]

(6-18) N-[2-(1,3-dimethylbutyl)phenyl]-5-fluoro-1,3-dimethyl-1H-pyrazole-4-carboxamide (known from EP-A 1 414 803) of the formula

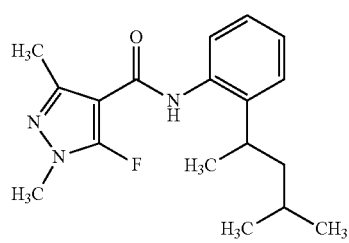 [SMILES: Cc1nn(C)c(F)c1C(=O)Nc1ccccc1C(C)CC(C)C]

(6-20) N-[2-(1,3-dimethylbutyl)phenyl]-2-(trifluoromethyl)benzamide (known from EP-A 1 519 913) of the formula

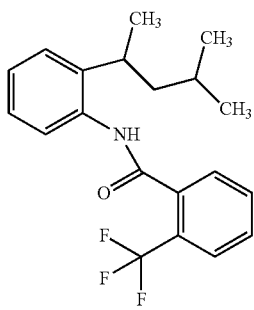 [SMILES: CC(C)CC(C)c1ccccc1NC(=O)c1ccccc1C(F)(F)F]

(6-21) N-[2-(1,3-dimethylbutyl)phenyl]-2-iodobenzamide (known from EP-A 1 519 913) of the formula

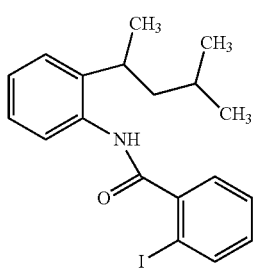 [SMILES: CC(C)CC(C)c1ccccc1NC(=O)c1ccccc1I]

(6-22) N-(4'-chloro-3'-fluorobiphenyl-2-yl)-4-(difluoromethyl)-2-methyl-1,3-thiazole-5-carboxamide (known from EP-A 1 404 407) of the formula

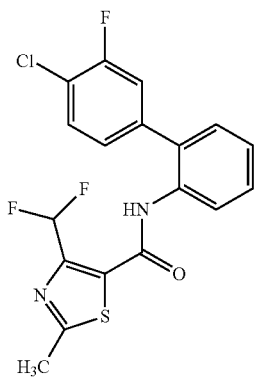 [SMILES: Cc1nc(C(F)F)c(C(=O)Nc2ccccc2-c2ccc(Cl)c(F)c2)s1]

(6-23) N-[5-(4-chlorophenyl)pyrimidin-4-yl]-2-iodo-N-(2-iodobenzoyl)benzamide of the formula

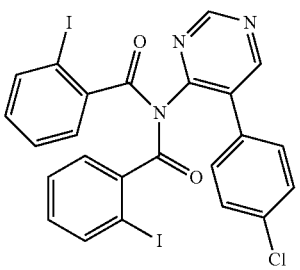 [SMILES: O=C(c1ccccc1I)N(C(=O)c1ccccc1I)c1ncncc1-c1ccc(Cl)cc1]

(6-24) N-(3',4'-dichlorobiphenyl-2-yl)-2-methyl-4-(trifluoromethyl)-1,3-thiazole-5-carboxamide (known from EP-A 1 474 406) of the formula

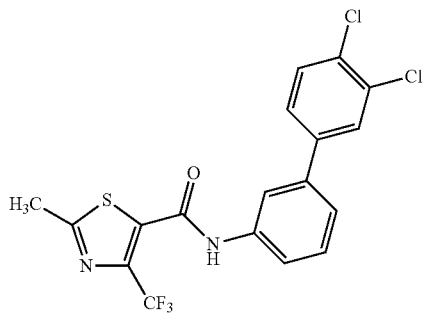 [SMILES: Cc1nc(C(F)(F)F)c(C(=O)Nc2cccc(-c3ccc(Cl)c(Cl)c3)c2)s1]

(6-25) fluopyram (ISO-proposed) N-[2-[3-chloro-5-(trifluoromethyl)-2-pyridinyl]ethyl]-2-(trifluoromethyl)benzamide (known from WO 2004016088)

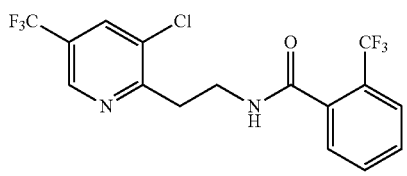 [SMILES: O=C(NCCc1ncc(C(F)(F)F)cc1Cl)c1ccccc1C(F)(F)F]

(6-26) sedaxane (ISO-proposed) a mixture of 2 cis isomers of 2'-[(1RS,2RS)-1,1'-bicycloprop-2-yl]-3-(difluoromethyl)-1-methylpyrazole-4-carboxanilide and 2 trans isomers of 2'-

[(1RS,2SR)-1,1'-bicycloprop-2-yl]-3-(difluoromethyl)-1-methylpyrazole-4-carboxanilide (known from WO 2003/074491 A1)

cis-isomers

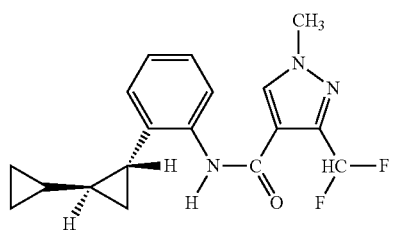

trans-isomers

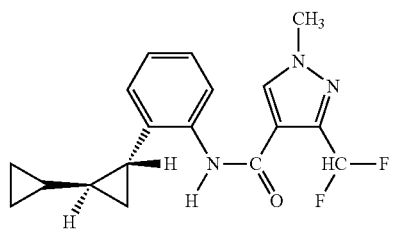

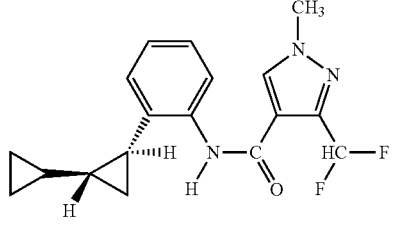

(6-27) isopyrazam (ISO-proposed) a mixture of 2 syn isomers of 3-(difluoromethyl)-1-methyl-N-[(1RS,4SR,9RS)-1,2,3,4-tetrahydro-9-isopropyl-1,4-methanonaphthalen-5-yl]pyrazole-4-carboxamide and 2 anti isomers of 3-(difluoromethyl)-1-methyl-N-[(1RS,4SR,9SR)-1,2,3,4-tetrahydro-9-isopropyl-1,4-methanonaphthalen-5-yl]pyrazole-4-carboxamide (known from WO 2004/035589 A1)

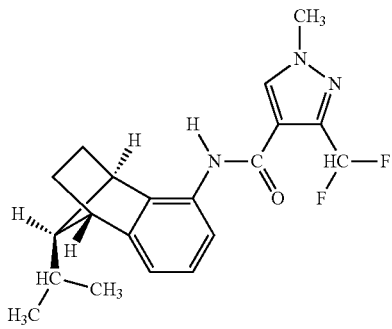

-continued

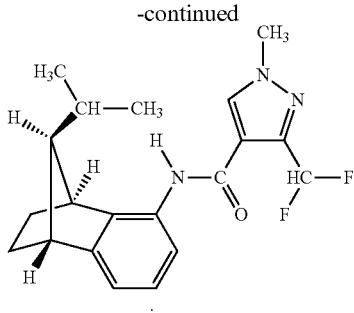

syn-isomers

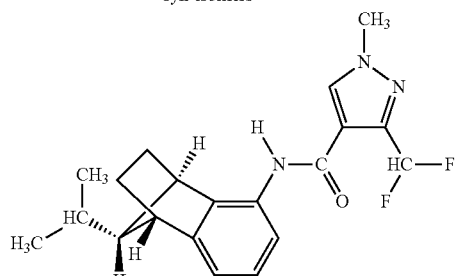

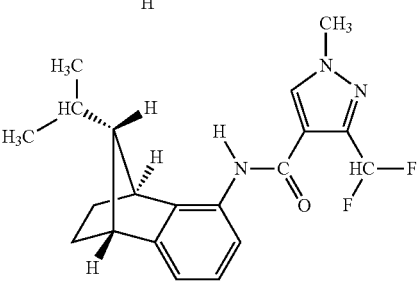

anti-isomers

Preferred combination partners of group (7) are (7-1) mancozeb (known from DE-A 12 34 704) having the IUPAC name manganese ethylenebis(dithiocarbamate) (polymeric) complex with zinc salt (7-2) maneb (known from U.S. Pat. No. 2,504,404) of the formula

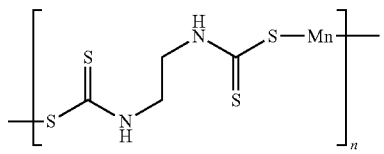

(7-3) metiram (known from DE-A 10 76 434) having the IUPAC name zinc ammoniate ethylenebis(dithiocarbamate)-poly(ethylenethiuram disulphide)

(7-4) propineb (known from GB 935 981) of the formula

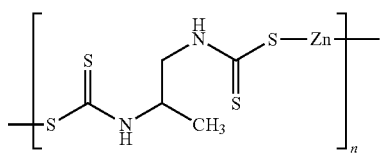

(7-5) thiram (known from U.S. Pat. No. 1,972,961) of the formula (7-6) zineb (known from DE-A 10 81 446) of the formula

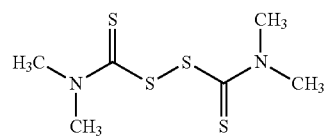

(7-7) ziram (known from U.S. Pat. No. 2,588,428) of the formula

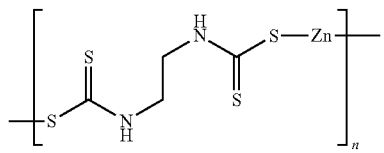

The formula (VI) comprises the following preferred combination partners of group (8):
(8-1) benalaxyl (known from DE-A 29 03 612) of the formula

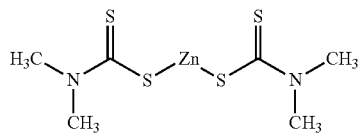

(8-2) furalaxyl (known from DE-A 25 13 732) of the formula

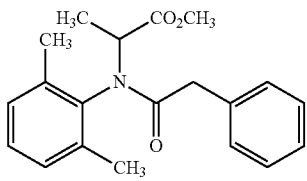 [SMILES: COC(=O)C(C)N(C(=O)Cc1ccccc1)c1c(C)cccc1C]

(8-3) metalaxyl (known from DE-A 25 15 091) of the formula

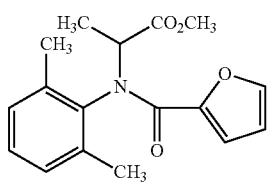 [SMILES: COC(=O)C(C)N(C(=O)c1ccco1)c1c(C)cccc1C]

(8-4) metalaxyl-M (known from WO 96/01559) of the formula

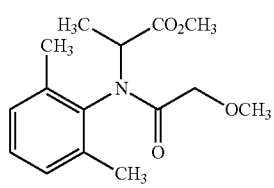 [SMILES: COCC(=O)N(c1c(C)cccc1C)C(C)C(=O)OC]

(8-5) benalaxyl-M of the formula

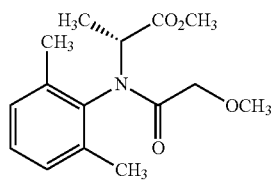

The formula (VII) comprises the following preferred combination partners of group (9):
(9-1) cyprodinil (known from EP-A 0 310 550) of the formula

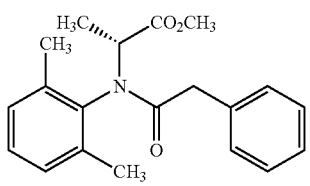 [SMILES: COC(=O)[C@@H](C)N(C(=O)Cc1ccccc1)c1c(C)cccc1C]

(9-2) mepanipyrim (known from EP-A 0 270 111) of the formula

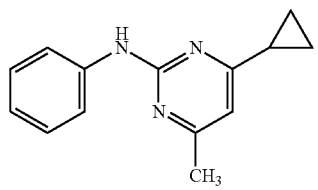 [SMILES: Cc1cc(C2CC2)nc(Nc2ccccc2)n1]

(9-3) pyrimethanil (known from DD 151 404) of the formula

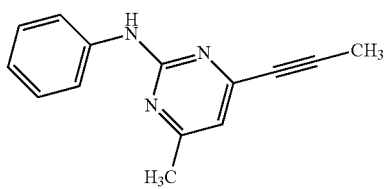 [SMILES: CC#Cc1cc(C)nc(Nc2ccccc2)n1]

The formula (VIII) comprises the following preferred combination partners of group (10):
(10-1) 6-chloro-5-[(3,5-dimethylisoxazol-4-yl)sulphonyl]-2,2-difluoro-5H-[1,3]dioxolo[4,5-f]benzimidazole (known from WO 97/06171) of the formula

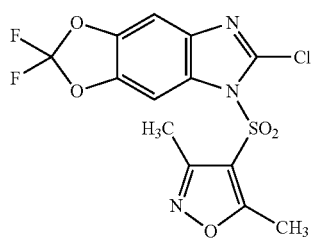 [SMILES: Cc1noc(C)c1S(=O)(=O)n1c(Cl)nc2cc3c(cc21)OC(F)(F)O3]

(10-2) benomyl (known from U.S. Pat. No. 3,631,176) of the formula

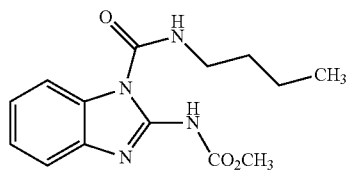 [SMILES: CCCCNC(=O)n1c(NC(=O)OC)nc2ccccc21]

(10-3) carbendazim (known from U.S. Pat. No. 3,010,968) of the formula

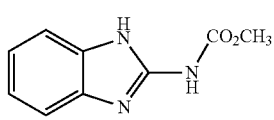 [SMILES: COC(=O)Nc1nc2ccccc2[nH]1]

(10-4) chlorfenazole of the formula

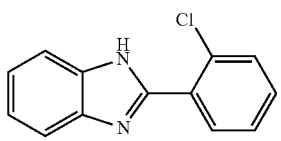 [SMILES: Clc1ccccc1-c1nc2ccccc2[nH]1]

(10-5) fuberidazole (known from DE-A 12 09 799) of the formula

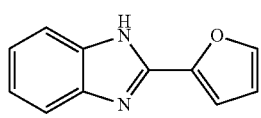

(10-6) thiabendazole (known from U.S. Pat. No. 3,206,468) of the formula

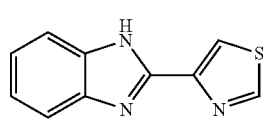 [SMILES: c1ccc2[nH]c(-c3cscn3)nc2c1]

The formula (IX) comprises the following preferred combination partners of group (11):

(11-1) diethofencarb (known from EP-A 0 078 663) of the formula

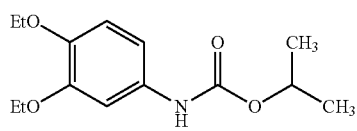 [SMILES: CCOc1ccc(NC(=O)OC(C)C)cc1OCC]

(11-2) propamocarb (known from U.S. Pat. No. 3,513,241) of the formula

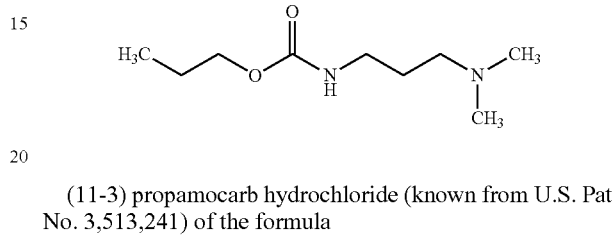

(11-3) propamocarb hydrochloride (known from U.S. Pat. No. 3,513,241) of the formula

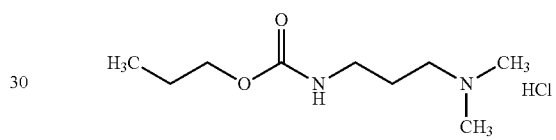

(11-4) propamocarb-fosetyl of the formula

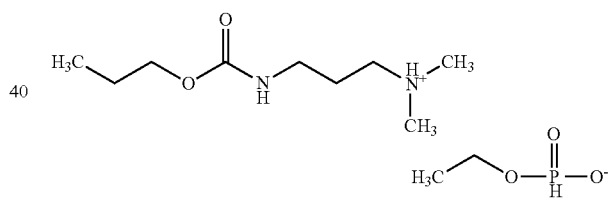

(11-5) pyribencarb (ISO-proposed, KUF-1204) [[2-chloro-5-[(1E)-1-[[(6-methyl-2-pyridinyl)methoxy]imino]ethyl]phenyl]methyl]carbamic acid methyl ester (known from WO 2001010825)

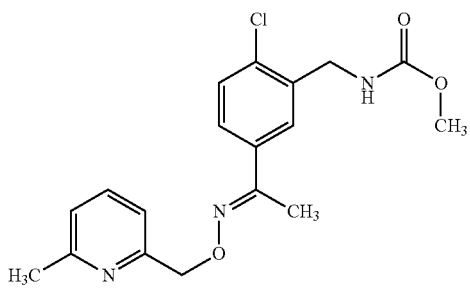

Preferred combination partners of group (12) are (12-1) captafol (known from U.S. Pat. No. 3,178,447) of the formula

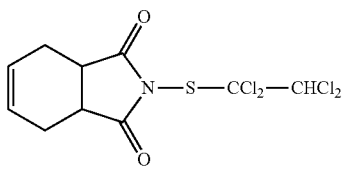

(12-2) captan (known from U.S. Pat. No. 2,553,770) of the formula

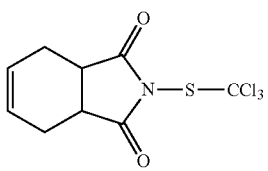

(12-3) folpet (known from U.S. Pat. No. 2,553,770) of the formula

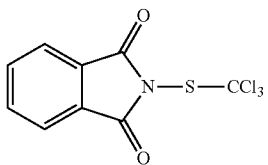

(12-4) iprodione (known from DE-A 21 49 923) of the formula

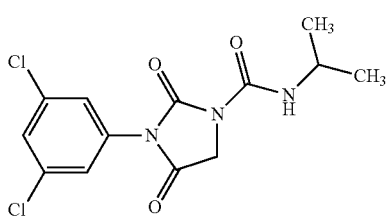 [SMILES: CC(C)NC(=O)N1CC(=O)N(c2cc(Cl)cc(Cl)c2)C1=O]

(12-5) procymidone (known from DE-A 20 12 656) of the formula

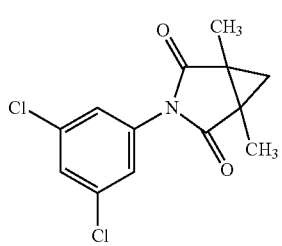 [SMILES: CC12CC1(C)C(=O)N(c1cc(Cl)cc(Cl)c1)C2=O]

(12-6) vinclozolin (known from DE-A 22 07 576) of the formula

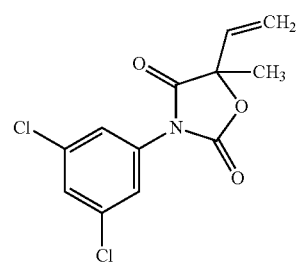 [SMILES: C=CC1(C)OC(=O)N(c2cc(Cl)cc(Cl)c2)C1=O]

Preferred combination partners of group (13) are (13-1) dodine (known from GB 11 03 989) of the formula

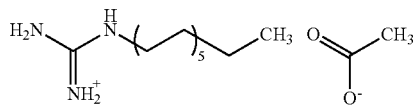

(13-2) guazatine (known from GB 11 14 155)

(13-3) iminoctadine triacetate (known from EP-A 0 155 509) of the formula

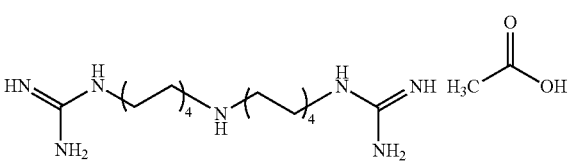

Preferred combination partners of group (14) are (14-1) cyazofamid (known from EP-A 0 298 196) of the formula

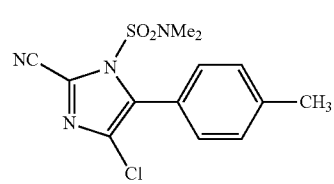

(14-2) prochloraz (known from DE-A 24 29 523) of the formula

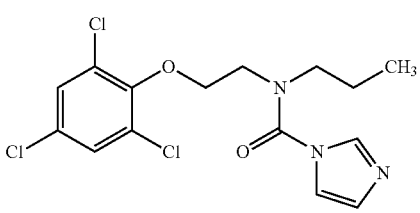 [SMILES: CCCN(CCOc1c(Cl)cc(Cl)cc1Cl)C(=O)n1ccnc1]

(14-3) triazoxide (known from DE-A 28 02 488) of the formula (14-4) pefurazoate (known from EP-A 0 248 086) of the formula

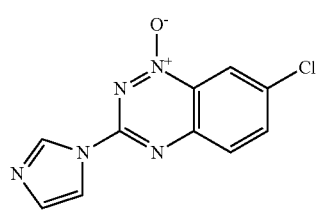 [SMILES: [O-][n+]1nc(-n2ccnc2)nc2ccc(Cl)cc21]

(14-5) fenamidone (known from EP-A 00629616) of the formula

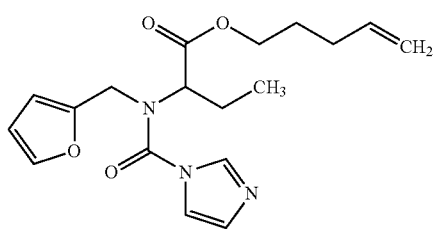 [SMILES: C=CCCCOC(=O)C(CC)N(Cc1ccco1)C(=O)n1ccnc1]

The formula (X) comprises the following preferred combination partners of group (15):

(15-1) aldimorph (known from DD 140 041) of the formula

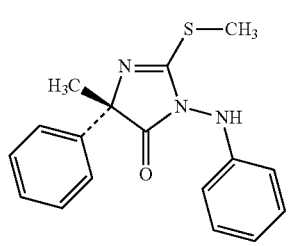 [SMILES: CSC1=N[C@@](C)(c2ccccc2)C(=O)N1Nc1ccccc1]

(15-2) tridemorph (known from GB 988 630) of the formula

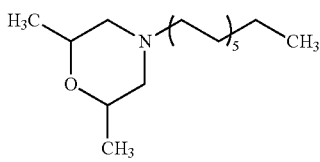

(15-3) dodemorph (known from DE-A 25 432 79) of the formula (15-4) fenpropimorph (known from DE-A 26 56 747) of the formula

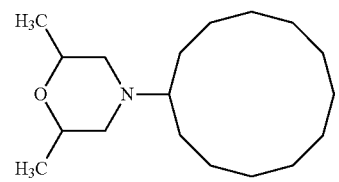 [SMILES: CC1CN(C2CCCCCCCCCCC2)CC(C)O1]

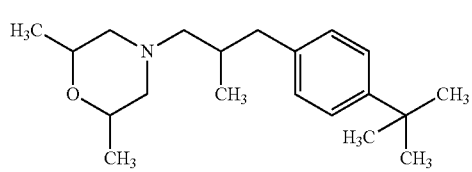 [SMILES: CC(Cc1ccc(C(C)(C)C)cc1)CN1CC(C)OC(C)C1]

(15-5) dimethomorph (known from EP-A 0 219 756) of the formula

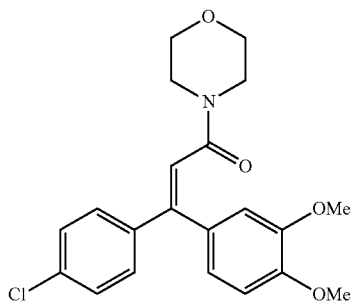 [SMILES: COc1ccc(/C(=C\C(=O)N2CCOCC2)c2ccc(Cl)cc2)cc1OC]

(15-6) flumorph (known from EP-A 0 860 438) of the formula

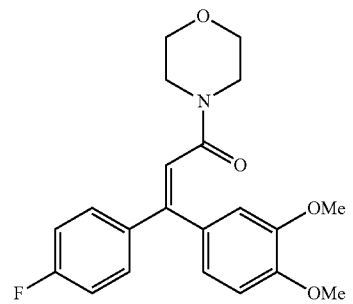 [SMILES: COc1ccc(/C(=C\C(=O)N2CCOCC2)c2ccc(F)cc2)cc1OC]

The formula (XI) comprises the following preferred combination partners of group (16):

(16-1) fenpiclonil (known from EP-A 0 236 272) of the formula

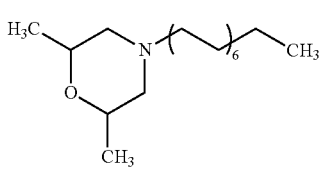

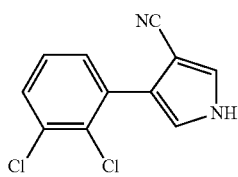 [SMILES: N#Cc1c[nH]cc1-c1cccc(Cl)c1Cl]

(16-2) fludioxonil (known from EP-A 0 206 999) of the formula

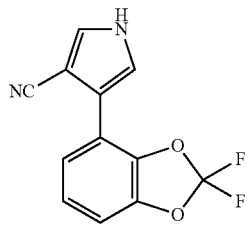 [SMILES: N#Cc1c[nH]cc1-c1cccc2c1OC(F)(F)O2]

(16-3) pyrrolnitrine (known from JP 65-25876) of the formula

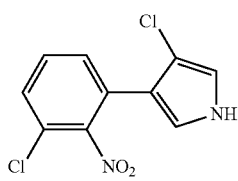 [SMILES: O=[N+]([O-])c1c(Cl)cccc1-c1c[nH]cc1Cl]

Preferred combination partners of group (17) are
(17-1) fosetyl-Al (known from DE-A 24 56 627) of the formula

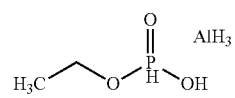

(17-2) phosphonic acid (known chemical) of the formula

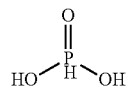

(17-3) tolclofos-methyl (known from DE-A 25 01 040) of the formula

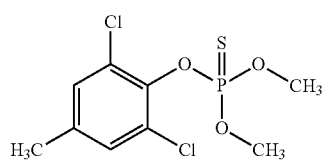

The formula (XII) comprises the following preferred combination partners of group (18) which are known from WO 96/23793 and may each be present as (E) or (Z) isomers. Accordingly, compounds of the formula (XII) can be present as a mixture of various isomers or else in the form of a single isomer. Preference is given to compounds of the formula (XII) in the form of their (E) isomer:

(18-1) the compound 2-(2,3-dihydro-1H-inden-5-yl)-N-[2-(3,4-dimethoxyphenyl)ethyl]-2-(methoxyimino)acetamide of the formula

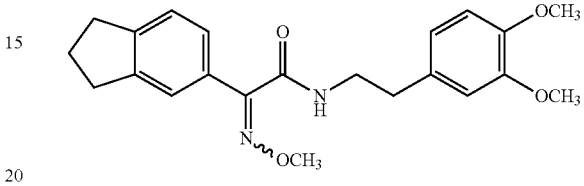

(18-2) the compound N-[2-(3,4-dimethoxyphenyl)ethyl]-2-(methoxyimino)-2-(5,6,7,8-tetrahydronaphthalen-2-yl)acetamide of the formula

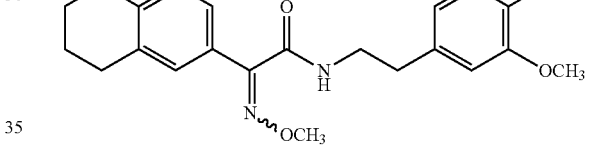

(18-3) the compound 2-(4-chlorophenyl)-N-[2-(3,4-dimethoxyphenyl)ethyl]-2-(methoxyimino)acetamide of the formula

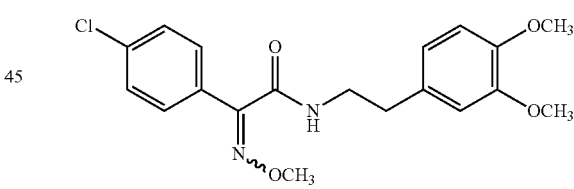

(18-4) the compound 2-(4-bromophenyl)-N-[2-(3,4-dimethoxyphenyl)ethyl]-2-(methoxyimino)acetamide of the formula

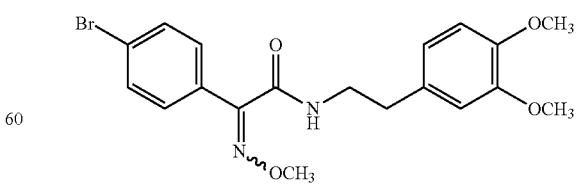

(18-5) the compound 2-(4-methylphenyl)-N-[2-(3,4-dimethoxyphenyl)ethyl]-2-(methoxyimino)acetamide of the formula

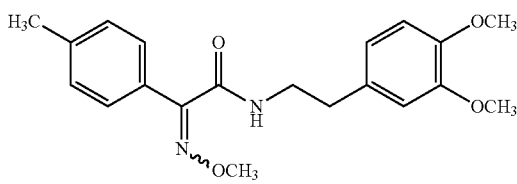 [SMILES: CON=C(C(=O)NCCc1ccc(OC)c(OC)c1)c1ccc(C)cc1]

(18-6) the compound 2-(4-ethylphenyl)-N-[2-(3,4-dimethoxyphenyl)ethyl]-2-(methoxyimino)acetamide of the formula

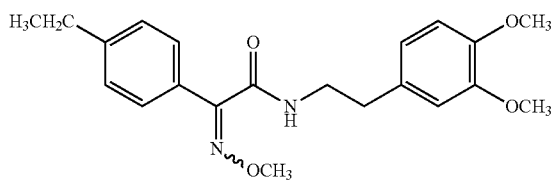

Preferred combination partners of group (19) are (19-1) acibenzolar-5-methyl (known from EP-A 0 313 512) of the formula

(19-2) chlorothalonil (known from U.S. Pat. No. 3,290,353) of the formula

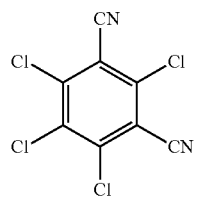 [SMILES: N#Cc1c(Cl)c(Cl)c(Cl)c(C#N)c1Cl]

(19-3) cymoxanil (known from DE-A 23 12 956) of the formula

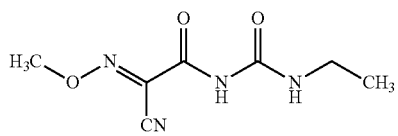

(19-4) edifenphos (known from DE-A 14 93 736) of the formula

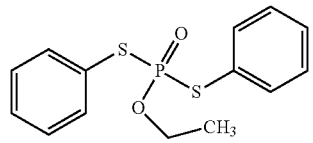 [SMILES: CCOP(=O)(Sc1ccccc1)Sc1ccccc1]

(19-5) famoxadone (known from EP-A 0 393 911) of the formula

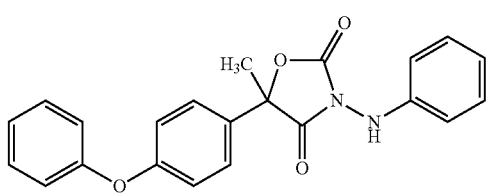 [SMILES: CC1(c2ccc(Oc3ccccc3)cc2)OC(=O)N(Nc2ccccc2)C1=O]

(19-6) fluazinam (known from EP-A 0 031 257) of the formula

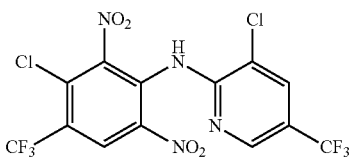 [SMILES: O=[N+]([O-])c1cc(C(F)(F)F)c(Cl)c([N+](=O)[O-])c1Nc1ncc(C(F)(F)F)cc1Cl]

(19-7) copper oxychloride (19-9) oxadixyl (known from DE-A 30 30 026) of the formula

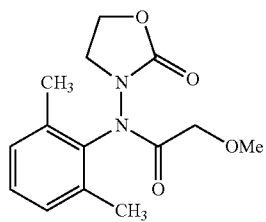 [SMILES: COCC(=O)N(c1c(C)cccc1C)N1CCOC1=O]

(19-10) spiroxamine (known from DE-A 37 35 555) of the formula

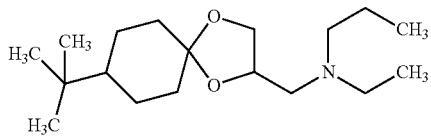 [SMILES: CCCN(CC)CC1COC2(CCC(C(C)(C)C)CC2)O1]

(19-11) dithianon (known from JP-A 44-29464) of the formula

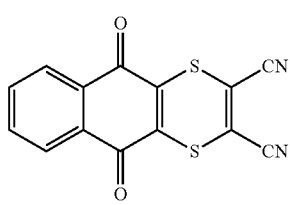 [SMILES: N#Cc1sc2c(=O)c3ccccc3c(=O)c=2sc1C#N]

(19-12) metrafenone (known from EP-A 0 897 904) of the formula

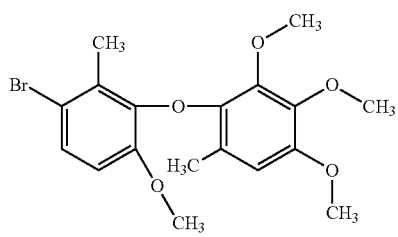 [SMILES: COc1ccc(Br)c(C)c1Oc1c(C)cc(OC)c(OC)c1OC]

(19-13) 2,3-dibutyl-6-chlorothieno[2,3-d]pyrimidin-4(3H)one (known from WO 99/14202) of the formula

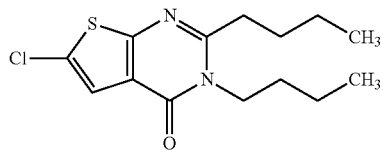 [SMILES: CCCCc1nc2sc(Cl)cc2c(=O)n1CCCC]

(19-14) probenazole (known from U.S. Pat. No. 3,629,428) of the formula

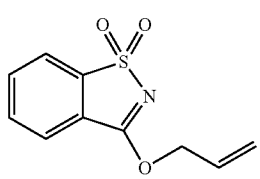

(19-15) isoprothiolane (known from U.S. Pat. No. 3,856,814) of the formula

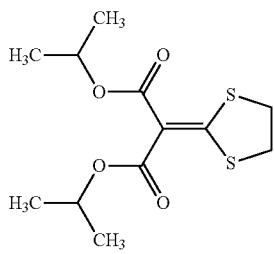 [SMILES: CC(C)OC(=O)C(C(=O)OC(C)C)=C1SCCS1]

(19-16) kasugamycin (known from GB 1 094 567) of the formula

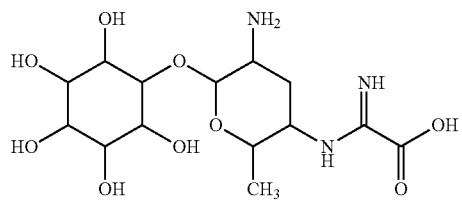 [SMILES: CC1OC(OC2C(O)C(O)C(O)C(O)C2O)C(N)CC1NC(=N)C(=O)O]

(19-17) phthalide (known from JP-A 57-55844) of the formula

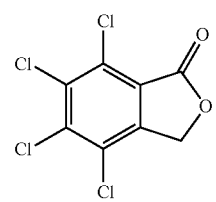 [SMILES: O=C1OCc2c(Cl)c(Cl)c(Cl)c(Cl)c21]

(19-18) ferimzone (known from EP-A 0 019 450) of the formula

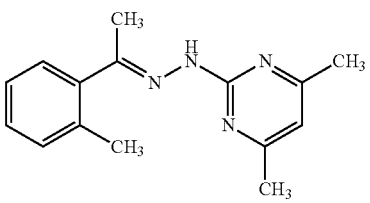 [SMILES: C/C(=N\Nc1nc(C)cc(C)n1)c1ccccc1C]

(19-19) tricyclazole (known from DE-A 22 50 077) of the formula

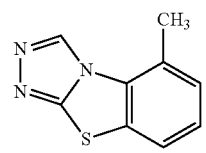

(19-20) cyprosulfamide of the formula

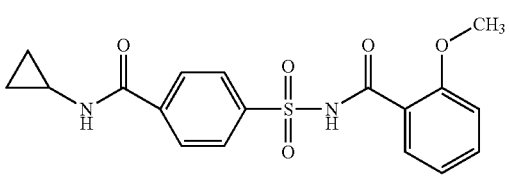 [SMILES: COc1ccccc1C(=O)NS(=O)(=O)c1ccc(C(=O)NC2CC2)cc1]

(19-21) mandipropamid (known from WO 01/87822) of the formula

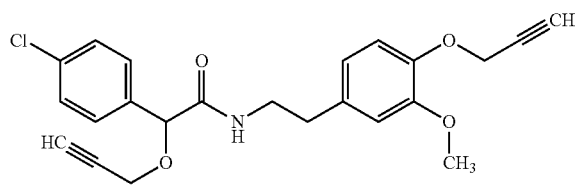 [SMILES: C#CCOc1ccc(CCNC(=O)C(OCC#C)c2ccc(Cl)cc2)cc1OC]

Preferred combination partners of group (20) are (20-1) pencycuron (known from DE-A 27 32 257) of the formula

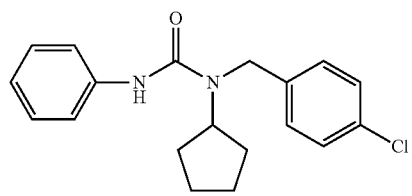 [SMILES: O=C(Nc1ccccc1)N(Cc1ccc(Cl)cc1)C1CCCC1]

(20-2) thiophanate-methyl (known from DE-A 18 06 123) of the formula

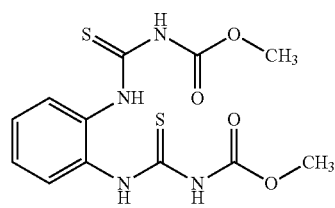 [SMILES: COC(=O)NC(=S)Nc1ccccc1NC(=S)NC(=O)OC]

(20-3) thiophanate-ethyl (known from DE-A 18 06 123) of the formula

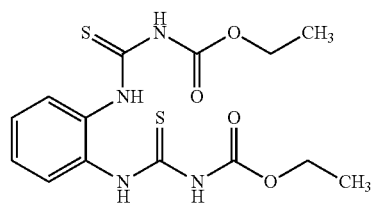 [SMILES: CCOC(=O)NC(=S)Nc1ccccc1NC(=S)NC(=O)OCC]

Preferred combination partners of group (21) are (21-1) fenoxanil (known from EP-A 0 262 393) of the formula

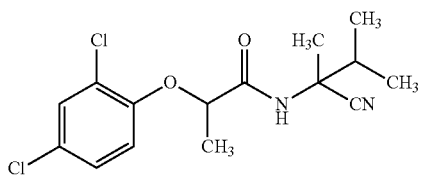 [SMILES: CC(Oc1ccc(Cl)cc1Cl)C(=O)NC(C)(C#N)C(C)C]

(21-2) diclocymet (known from JP-A 7-206608) of the formula

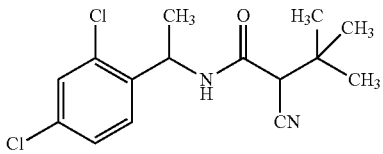 [SMILES: CC(NC(=O)C(C#N)C(C)(C)C)c1ccc(Cl)cc1Cl]

Preferred combination partners of group (22) are (22-1) 5-chloro-N-[(1S)-2,2,2-trifluoro-1-methylethyl]-6-(2,4,6-trifluorophenyl)[1,2,4]triazolo[1,5-a]pyrimidine-7-amine (known from U.S. Pat. No. 5,986,135) of the

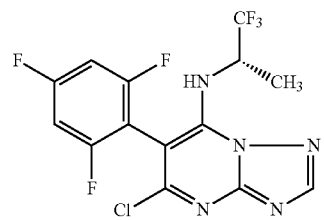 [SMILES: C[C@H](Nc1c(-c2c(F)cc(F)cc2F)c(Cl)nc2ncnn12)C(F)(F)F]

(22-2) 5-chloro-N-[(1R)-1,2-dimethylpropyl]-6-(2,4,6-trifluorophenyl)[1,2,4]triazolo[1,5-a]pyrimidine-7-amine (known from WO 02/38565) of the formula

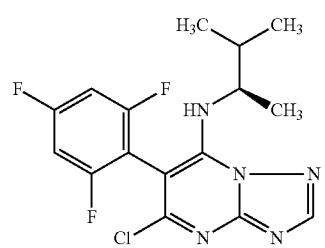 [SMILES: CC(C)[C@@H](C)Nc1c(-c2c(F)cc(F)cc2F)c(Cl)nc2ncnn12]

(22-3) 5-chloro-6-(2-chloro-6-fluorophenyl)-7-(4-methylpiperidin-1-yl)[1,2,4]triazolo[1,5-a]pyrimidine (known from U.S. Pat. No. 5,593,996) of the formula

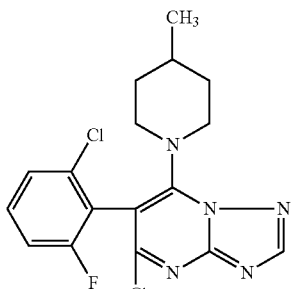

(22-4) 5-chloro-6-(2,4,6-trifluorophenyl)-7-(4-methylpiperidin-1-yl)[1,2,4]triazolo[1,5-a]pyrimidine (known from DE-A 101 24 208) of the formula

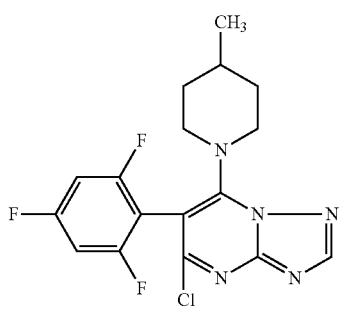 [SMILES: CC1CCN(c2c(-c3c(F)cc(F)cc3F)c(Cl)nc3ncnn23)CC1]

Preferred combination partners of group (23) are (23-1) 2-butoxy-6-iodo-3-propylbenzopyran-4-one (known from WO 03/014103) of the formula

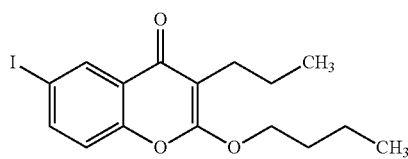

(23-2) 2-ethoxy-6-iodo-3-propylbenzopyran-4-one (known from WO 03/014103) of the formula

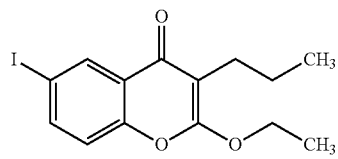 [SMILES: CCCc1c(OCC)oc2ccc(I)cc2c1=O]

(23-3) 6-iodo-2-propoxy-3-propylbenzopyran-4-one (known from WO 03/014103) of the formula

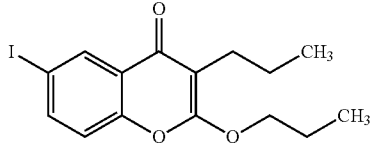 [SMILES: CCCOc1oc2ccc(I)cc2c(=O)c1CCC]

(23-4) 2-but-2-ynyloxy-6-iodo-3-propylbenzopyran-4-one (known from WO 03/014103) of the formula

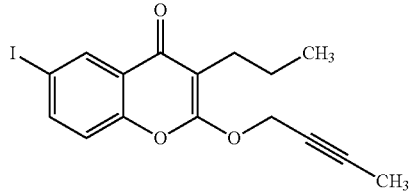

(23-5) 6-iodo-2-(1-methylbutoxy)-3-propylbenzopyran-4-one (known from WO 03/014103) of the formula

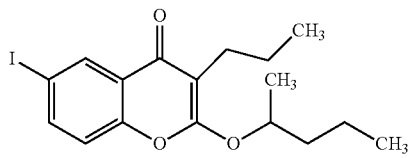 [SMILES: CCCc1c(OC(C)CCC)oc2ccc(I)cc2c1=O]

(23-6) 2-but-3-enyloxy-6-iodobenzopyran-4-one (known from WO 03/014103) of the formula

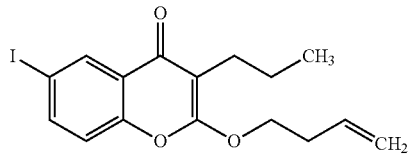

(23-7) 3-butyl-6-iodo-2-isopropoxybenzopyran-4-one (known from WO 03/014103) of the formula

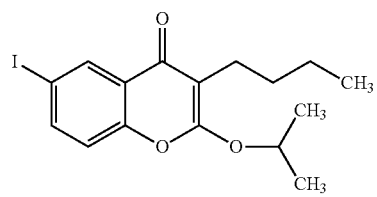

Preferred combination partners of group (24) are (24-1) N-(3',4'-dichloro-5-fluoro-1,1'-biphenyl-2-yl)-3-(difluoromethyl)-1-methyl-1H-pyrazole-4-carboxamide (known from WO 03/070705) of the formula

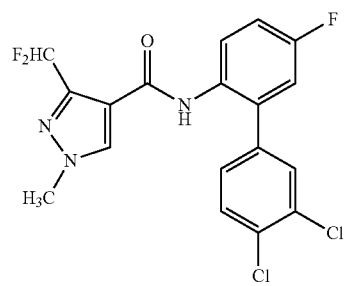 [SMILES: Cn1cc(C(=O)Nc2ccc(F)cc2-c2ccc(Cl)c(Cl)c2)c(C(F)F)n1]

(24-2) 3-(difluoromethyl)-N-{3'-fluoro-4'-[(E)-(methoxyimino)methyl]-1,1'-biphenyl-2-yl}-1-methyl-1H-pyrazole-4-carboxamide (known from WO 02/08197) of the formula

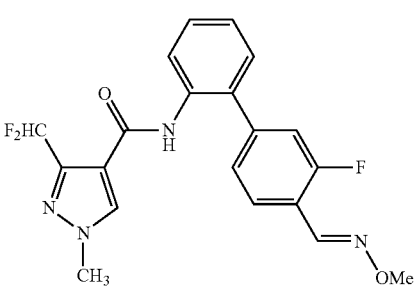 [SMILES: CO/N=C/c1ccc(-c2ccccc2NC(=O)c2cn(C)nc2C(F)F)cc1F]

(24-3) 3-(trifluoromethyl)-N-{3'-fluoro-4'-[(E)-(methoxyimino)methyl]-1,1'-biphenyl-2-yl}-1-methyl-1H-pyrazole-4-carboxamide (known from WO 02/08197) of the formula

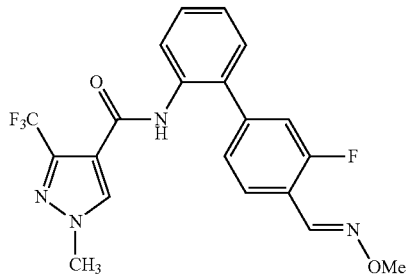 [SMILES: CO/N=C/c1ccc(-c2ccccc2NC(=O)c2cn(C)nc2C(F)(F)F)cc1F]

(24-4) N-(3',4'-dichloro-1,1'-biphenyl-2-yl)-5-fluoro-1,3-dimethyl-1H-pyrazole-4-carboxamide (known from WO 00/14701) of the formula

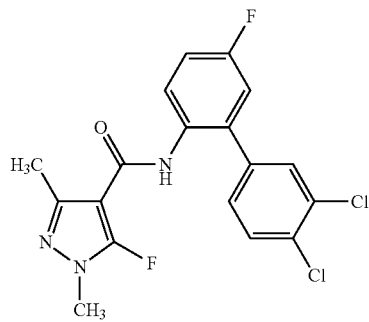 [SMILES: Cc1nn(C)c(F)c1C(=O)Nc1ccc(F)cc1-c1ccc(Cl)c(Cl)c1]

(24-5) N-(4'-chloro-3'-fluoro-1,1'-biphenyl-2-yl)-2-methyl-4-(trifluoromethyl)-1,3-thiazole-5-carboxamide (known from WO 03/066609) of the formula

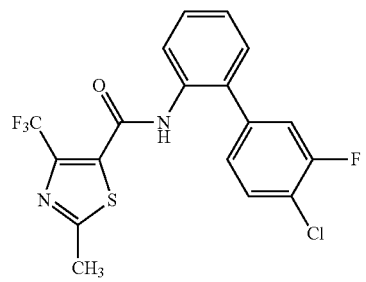 [SMILES: Cc1nc(C(F)(F)F)c(C(=O)Nc2ccccc2-c2ccc(Cl)c(F)c2)s1]

(24-6) N-(4'-chloro-1,1'-biphenyl-2-yl)-4-(difluoromethyl)-2-methyl-1,3-thiazole-5-carboxamide (known from WO 03/066610) of the formula

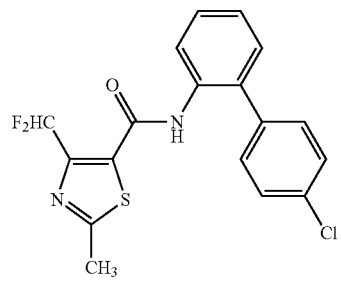

(24-7) N-(4'-bromo-1,1'-biphenyl-2-yl)-4-(difluoromethyl)-2-methyl-1,3-thiazole-5-carboxamide (known from WO 03/066610) of the formula

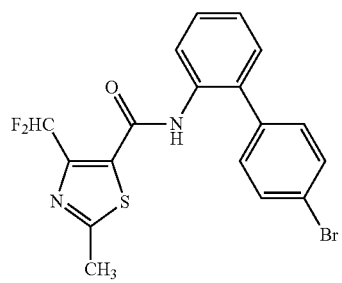 [SMILES: Cc1nc(C(F)F)c(C(=O)Nc2ccccc2-c2ccc(Br)cc2)s1]

(24-8) 4-(difluoromethyl)-2-methyl-N-[4'-(trifluoromethyl)-1,1'-biphenyl-2-yl]-1,3-thiazole-5-carboxamide (known from WO 03/066610) of the formula

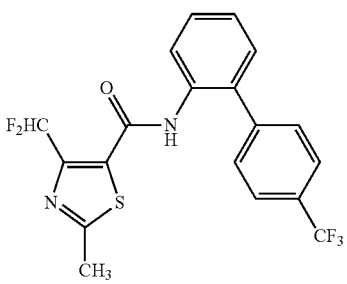 [SMILES: Cc1nc(C(F)F)c(C(=O)Nc2ccccc2-c2ccc(C(F)(F)F)cc2)s1]

(24-9) bixafen (ISO-proposed) N-(3',4'-dichloro-5-fluoro [1,1'-biphenyl]-2-yl)-3-(difluoromethyl)-1-methyl-1H-pyrazole-4-carboxamide (known from WO 2003070705)

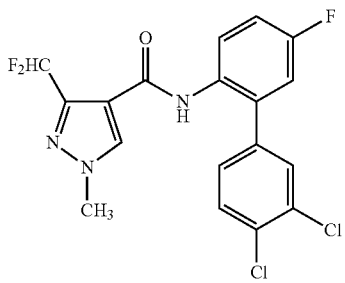 [SMILES: Cn1cc(C(=O)Nc2ccc(F)cc2-c2ccc(Cl)c(Cl)c2)c(C(F)F)n1]

Preferred combination partner of group (25) is
(25-1) amisulbrom (ISO-proposed, NC-224) 3-[(3-bromo-6-fluoro-2-methyl-1H-indol-1-yl)sulphonyl]-N,N-dimethyl-1H-1,2,4-triazole-1-sulphonamide (known from JP 2001187786)

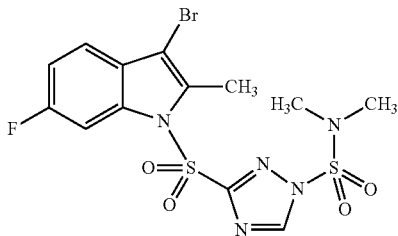 [SMILES: Cc1c(Br)c2ccc(F)cc2n1S(=O)(=O)c1ncn(S(=O)(=O)N(C)C)n1]

Preferred combination partner of group (26) is
(26-1) flutianil (Z)-[3-(2-methoxyphenyl)-1,3-thiazolidin-2-ylidene](α,α,α,4-tetrafluoro-m-tolylthio)acetonitrile (known from JP 2000319270 A)

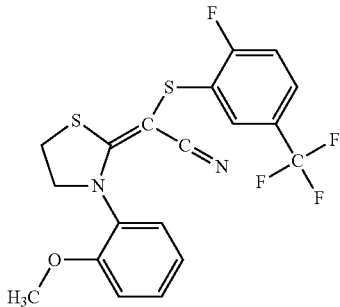 [SMILES: COc1ccccc1N1CCS/C1=C(/C=N)Sc1cc(C(F)(F)F)ccc1F]

Preferred combination partner of group (27) is
(27-1) meptyldinocap (RS)-2-(1-methylheptyl)-4,6-dinitrophenyl crotonate (known from: Meptyldinocap: a new active substance for control of powdery mildew. Hufnagl, A. E.; Distler, B.; Bacci, L.; Valverde, P. Dow AgroSciences, Mougins, Fr. International Plant Protection Congress, Proceedings, 16th, Glasgow, United Kingdom, Oct. 15-18, 2007 (2007), 1 32-39. Publisher: British Crop Production Council, Alton, UK)

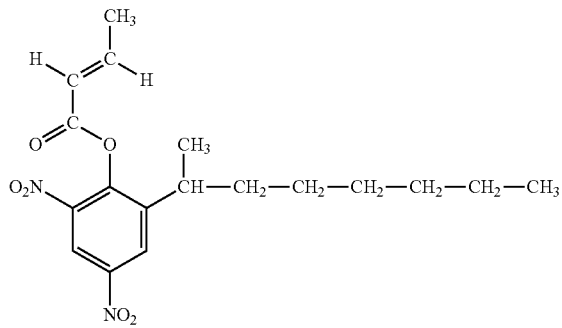 [SMILES: C/C=C/C(=O)Oc1c(C(C)CCCCCC)cc([N+](=O)[O-])cc1[N+](=O)[O-]]

The compound (6-7) carpropamid has three asymmetrical substituted carbon atoms. Accordingly, the compound (6-7) can be present as a mixture of various isomers or else in the form of a single component. Particular preference is given to the compounds
(1S,3R)-2,2-dichloro-N-[(1R)-1-(4-chlorophenyl)ethyl]-1-ethyl-3-methylcyclopropanecarboxamide of the formula

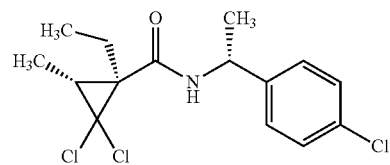 [SMILES: CC[C@@]1(C(=O)N[C@H](C)c2ccc(Cl)cc2)[C@@H](C)C1(Cl)Cl]

and
(1R,3S)-2,2-dichloro-N-[(1R)-1-(4-chlorophenyl)ethyl]-1-ethyl-3-methylcyclopropanecarboxamide of the formula

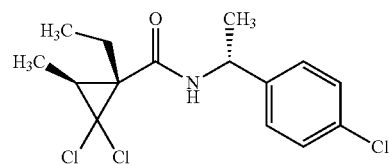 [SMILES: CC[C@]1(C(=O)N[C@H](C)c2ccc(Cl)cc2)[C@H](C)C1(Cl)Cl]

The active compound combinations according to the invention preferably comprise at least one of the compounds of the formula (I) selected from the group consisting of the compounds of the formulae (I-a), (I-b), (I-c) and (1-d) shown above, with the proviso that 4-{[(6-chloropyrid-3-yl)methyl](methyl)amino}furan-2(5H)-one and 4-{[(6-chloropyrid-3-yl)methyl](cyclopropyl)amino}furan-2(5H)-one are excluded, and an active compound selected from groups (2) to (27) mentioned above.

The active compound combinations according to the invention furthermore preferably comprise at least one of the compounds of the formula (I) selected from the group consisting of the compounds of the formulae (I-a), (I-b) and (I-c) shown above and an active compound selected from groups (2) to (27) mentioned above.

Particularly preferably, the active compound combinations according to the invention comprise at least one of the compounds of the formula (I) in which A is selected from among the radicals 6-fluoropyrid-3-yl, 6-chloropyrid-3-yl, 6-bromopyrid-3-yl, 5-fluoro-6-chloropyrid-3-yl, 2-chloro-1,3-thiazol-5-yl and 5,6-dichloropyrid-3-yl and $R^1$ is selected from among the radicals methyl, cyclopropyl, methoxy, 2-fluoroethyl and 2,2-difluoroethyl, with the proviso that 4-{[(6-chloropyrid-3-yl)methyl](methyl)amino}furan-2(5H)-one and 4-{[(6-chloropyrid-3-yl)methyl](cyclopropyl)amino}furan-2(5H)-one are excluded, and an active compound selected from groups (2) to (27) mentioned above.

Very particularly preferably, the active compound combinations according to the invention comprise at least one compound of the formula (I) selected from the group consisting of the compounds of the formulae (I-1), (I-2), (I-3), (I-4), (I-5), (I-6), (I-7) and (I-8) shown above, and an active compound selected from groups (2) to (27) mentioned above.

Particularly preferred combination partners of groups (2) to (27) are the following active compounds:
(2-1) azoxystrobin
(2-2) fluoxastrobin
(2-3) (2E)-2-(2-{[6-(3-chloro-2-methylphenoxy)-5-fluoro-4-pyrimidinyl]oxy}phenyl)-2-(methoxyimino)-N-methylethanamide
(2-4) trifloxystrobin
(2-5) (2E)-2-(methoxyimino)-N-methyl-2-(2-{[({(1E)-1-[3-(trifluoromethyl)phenyl]ethylidene}amino)oxy]methyl}phenyl)ethanamide (2-6) (2E)-2-(methoxyimino)-N-methyl-2-{2-[(E)-({1-[3-(trifluoromethyl)phenyl]ethoxy}imino)methyl]phenyl}ethanamide (2-8) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one (2-9) kresoxim-methyl
(2-10) dimoxystrobin
(2-11) picoxystrobin
(2-12) pyraclostrobin
(2-13) metominostrobin
(3-3) propiconazole
(3-4) difenoconazole
(3-6) cyproconazole
(3-7) hexaconazole
(3-8) penconazole
(3-9) myclobutanil
(3-10) tetraconazole
(3-12) epoxiconazole
(3-13) flusilazole
(3-15) prothioconazole
(3-16) fenbuconazole
(3-17) tebuconazole
(3-18) ipconazole
(3-19) metconazole
(3-20) triticonazole
(3-21) bitertanol
(3-22) triadimenol
(3-23) triadimefon
(3-24) fluquinconazole
(4-1) dichlofluanid
(4-2) tolylfluanid
(5-1) iprovalicarb
(5-3) benthiavalicarb
(5-4) valiphenal
(6-2) boscalid
(6-5) ethaboxam
(6-6) fenhexamid
(6-7) carpropamid
(6-8) 2-chloro-4-[(2-fluoro-2-methylpropanoyl)amino]-N,N-dimethylbenzamide
(6-9) fluopicolid
(6-10) zoxamide
(6-11) isotianil
(6-14) penthiopyrad
(6-16) N-[2-(1,3-dimethylbutyl)phenyl]-1-methyl-4-(trifluoromethyl)-1H-pyrrole-3-carboxamide
(6-17) flutolanil
(6-18) N-[2-(1,3-dimethylbutyl)phenyl]-5-fluoro-1,3-dimethyl-1H-pyrazole-4-carboxamide
(6-25) fluopyram
(6-26) sedaxane (ISO-proposed)
(6-27) isopyrazam (ISO-proposed)
(7-1) mancozeb
(7-2) maneb
(7-4) propineb
(7-5) thiram
(7-6) zineb
(8-1) benalaxyl
(8-2) furalaxyl
(8-3) metalaxyl
(8-4) metalaxyl-M
(8-5) benalaxyl-M
(9-1) cyprodinil
(9-2) mepanipyrim
(9-3) pyrimethanil (10-1) 6-chloro-5-[(3,5-dimethylisoxazol-4-yl)sulphonyl]-2,2-difluoro-5H-[1,3]dioxolo[4,5-f]benzimidazole
(10-3) carbendazim
(11-1) diethofencarb
(11-2) propamocarb
(11-3) propamocarb-hydrochloride
(11-4) propamocarb-fosetyl
(11-5) pyribencarb
(12-2) captan
(12-3) folpet
(12-4) iprodione
(12-5) procymidone
(13-1) dodine
(13-2) guazatine
(13-3) iminoctadine triacetate
(14-1) cyazofamid
(14-2) prochloraz
(14-3) triazoxide
(14-5) fenamidone
(15-4) fenpropimorph
(15-5) dimethomorph
(15-6) flumorph
(16-2) fludioxonil
(17-1) fosetyl-Al
(17-2) phosphonic acid
(17-3) tolclofos-methyl
(19-1) acibenzolar-5-methyl
(19-2) chlorothalonil
(19-3) cymoxanil
(19-5) famoxadone
(19-6) fluazinam
(19-7) copper oxychloride
(19-9) oxadixyl
(19-10) spiroxamine
(19-21) cyprosulfamide
(19-22) mandipropamid
(20-1) pencycuron
(20-2) thiophanate-methyl
(22-1) 5-chloro-N-[(1S)-2,2,2-trifluoro-1-methylethyl]-6-(2,4,6-trifluorophenyl)[1,2,4]triazolo[1,5-a]pyrimidine-7-amine
(22-2) 5-chloro-N-[(1R)-1,2-dimethylpropyl]-6-(2,4,6-trifluorophenyl)[1,2,4]triazolo[1,5-a]pyrimidine-7-amine
(22-4) 5-chloro-6-(2,4,6-trifluorophenyl)-7-(4-methylpiperidin-1-yl)[1,2,4]triazolo[1,5-a]pyrimidine
(23-1) 2-butoxy-6-iodo-3-propylbenzopyran-4-one
(23-2) 2-ethoxy-6-iodo-3-propylbenzopyran-4-one
(23-3) 6-iodo-2-propoxy-3-propylbenzopyran-4-one
(24-1) N-(3',4'-dichloro-5-fluoro-1,1'-biphenyl-2-yl)-3-(difluoromethyl)-1-methyl-1H-pyrazole-4-carboxamide
(24-3) 3-(trifluoromethyl)-N-{3'-fluoro-4'-[(E)-(methoxyimino)methyl]-1,1'-biphenyl-2-yl}-1-methyl-1H-pyrazole-4-carboxamide
(24-7) N-(4'-bromo-1,1'-biphenyl-2-yl)-4-(difluoromethyl)-2-methyl-1,3-thiazole-5-carboxamide
(24-9) bixafen
(25-1) amisulbrom
(26-1) flutianil
(27-1) meptyldinocap Very particularly preferred combination partners of groups (2) to (27) are the following active compounds:
(2-1) azoxystrobin
(2-2) fluoxastrobin
(2-3) (2E)-2-(2-{[6-(3-chloro-2-methylphenoxy)-5-fluoro-4-pyrimidinyl]oxy}phenyl)-2-(methoxyimino)-N-methylethanamide
(2-4) trifloxystrobin (3-15) prothioconazole
(3-17) tebuconazole
(3-18) ipconazole
(3-20) triticonazole
(3-21) bitertanol
(3-22) triadimenol
(3-24) fluquinconazole
(4-1) dichlofluanid
(4-2) tolylfluanid
(5-1) iprovalicarb
(6-6) fenhexamid
(6-7) carpropamid
(6-9) fluopicolid
(6-11) isotianil
(6-14) penthiopyrad
(6-17) flutolanil
(6-18) N-[2-(1,3-dimethylbutyl)phenyl]-5-fluoro-1,3-dimethyl-1H-pyrazole-4-carboxamide
(6-25) fluopyram
(7-4) propineb
(7-5) thiram
(8-3) metalaxyl
(8-4) metalaxyl-M
(8-5) benalaxyl-M
(9-3) pyrimethanil
(10-3) carbendazim
(11-2) propamocarb
(11-4) propamocarb-fosetyl
(11-5) pyribencarb
(12-4) iprodione
(14-2) prochloraz
(14-3) triazoxide
(14-5) fenamidone
(16-2) fludioxonil
(17-1) fosetyl-Al
(17-3) tolclofos-methyl
(19-10) spiroxamine
(19-21) cyprosulfamide
(19-22) mandipropamid
(20-1) pencycuron
(22-4) 5-chloro-6-(2,4,6-trifluorophenyl)-7-(4-methylpiperidin-1-yl) [1,2,4]triazolo[1,5-a]pyrimidine
(24-1) N-(3',4'-dichloro-5-fluoro-1,1'-biphenyl-2-yl)-3-(difluoromethyl)-1-methyl-1H-pyrazole-4-carboxamide
(24-9) bixafen
(25-1) amisulbrom Especially preferred combination partners of groups (2) to (27) are the following active compounds:
(2-1) azoxystrobin
(2-2) fluoxastrobin
(2-4) trifloxystrobin
(3-15) prothioconazole
(3-17) tebuconazole
(3-18) ipconazole
(3-20) triticonazole
(3-22) triadimenol
(4-2) tolylfluanid
(5-1) iprovalicarb
(6-7) carpropamid
(6-9) fluopicolid
(6-11) isotianil
(6-18) N-[2-(1,3-dimethylbutyl)phenyl]-5-fluoro-1,3-dimethyl-1H-pyrazole-4-carboxamide
(6-25) fluopyram
(7-5) thiram
(8-3) metalaxyl
(8-4) metalaxyl-M
(11-2) propamocarb
(11-5) pyribencarb
(12-4) iprodione
(14-5) fenamidone
(16-2) fludioxonil
(17-1) fosetyl-Al
(19-10) spiroxamine
(19-21) cyprosulfamide
(20-1) pencycuron
(24-1) N-(3',4'-dichloro-5-fluoro-1,1'-biphenyl-2-yl)-3-(difluoromethyl)-1-methyl-1H-pyrazole-4-carboxamide
(24-9) bixafen
(25-1) amisulbrom This gives the combinations listed in Table 1, where each combination per se is a very particularly preferred embodiment of the invention.

| No. of the active compound combination | Active compound combination comprising | | |
|---|---|---|---|
| | Compound of the formula I | | Active compound of groups 2 to 27 |
| I-1 | I-1 | and | (2-1) azoxystrobin |
| I-2 | I-1 | and | (2-2) fluoxastrobin |
| I-3 | I-1 | and | (2-3) (2E)-2-(2-{[6-(3-chloro-2-methylphenoxy)-5-fluoro-4-pyrimidinyl]oxy}phenyl)-2-(methoxyimino)-N-methylethanamide |
| I-4 | I-1 | and | (2-4) trifloxystrobin |
| I-5 | I-1 | and | (3-15) prothioconazole |
| I-6 | I-1 | and | (3-17) tebuconazole |
| I-7 | I-1 | and | (3-18) ipconazole |
| I-8 | I-1 | and | (3-20) triticonazole |
| I-9 | I-1 | and | (3-21) bitertanol |
| I-10 | I-1 | and | (3-22) triadimenol |
| I-11 | I-1 | and | (3-24) fluquinconazole |
| I-12 | I-1 | and | (4-1) dichlofluanid |
| I-13 | I-1 | and | (4-2) tolylfluanid |
| I-14 | I-1 | and | (5-1) iprovalicarb |
| I-15 | I-1 | and | (6-6) fenhexamid |
| I-16 | I-1 | and | (6-7) carpropamid |
| I-17 | I-1 | and | (6-9) fluopicolid |
| I-18 | I-1 | and | (6-11) isotianil |
| I-19 | I-1 | and | (6-14) penthiopyrad |
| I-20 | I-1 | and | (6-17) flutolanil |
| I-21 | I-1 | and | (6-18) N-[2-(1,3-dimethylbutyl)phenyl]-5-fluoro-1,3-dimethyl-1H-pyrazole-4-carboxamide |
| I-22 | I-1 | and | (6-25) fluopyram |
| I-23 | I-1 | and | (7-4) propineb |
| I-24 | I-1 | and | (7-5) thiram |
| I-25 | I-1 | and | (8-3) metalaxyl |
| I-26 | I-1 | and | (8-4) metalaxyl-M |
| I-27 | I-1 | and | (8-5) benalaxyl-M |
| I-28 | I-1 | and | (9-3) pyrimethanil |
| I-29 | I-1 | and | (10-3) carbendazim |
| I-30 | I-1 | and | (11-2) propamocarb |
| I-31 | I-1 | and | (11-4) propamocarb fosetyl |
| I-32 | I-1 | and | (11-5) pyribencarb |
| I-33 | I-1 | and | (12-4) iprodione |
| I-34 | I-1 | and | (14-2) prochloraz |
| I-35 | I-1 | and | (14-3) triazoxide |
| I-36 | | and | (14-5) fenamidone |
| I-37 | I-1 | and | (16-2) fludioxonil |
| I-38 | | and | (17-1) fosetyl-Al |
| I-39 | I-1 | and | (17-3) tolclofos-methyl |
| I-40 | I-1 | and | (19-10) spiroxamine |
| I-41 | I-1 | and | (19-21) cyprosulfamide |
| I-42 | I-1 | and | (19-22) mandipropamid |
| I-43 | I-1 | and | (20-1) pencycuron |
| I-44 | I-1 | and | (22-4) 5-chloro-6-(2,4,6-trifluorophenyl)-7-(4- |

-continued

| No. of the active compound combination | Compound of the formula I | | Active compound of groups 2 to 27 |
|---|---|---|---|
| I-45 | I-1 | and | methylpiperidin-1-yl)[1,2,4]triazolo[1,5-a]pyrimidine (24-1) N-(3',4'-dichloro-5-fluoro-1,1'-biphenyl-2-yl)-3-(difluoromethyl)-1-methyl-1H-pyrazole-4-carboxamide |
| I-46 | I-1 | and | (24-9) bixafen |
| I-47 | I-1 | and | (25-1) amisulbrom |

Furthermore, the combinations listed in Table 2 are obtained, where each combination per se is a preferred embodiment of the invention.

| No. of the active compound combination | Compound of the formula I | | Active compound of groups 2 to 27 |
|---|---|---|---|
| 2-1 | I-2 | and | (2-1) azoxystrobin |
| 2-2 | I-2 | and | (2-2) fluoxastrobin |
| 2-3 | I-2 | and | (2-3) (2E)-2-(2-{[6-(3-chloro-2-methylphenoxy)-5-fluoro-4-pyrimidinyl]oxy}phenyl)-2-(methoxyimino)-N-methylethanamide |
| 2-4 | I-2 | and | (2-4) trifloxystrobin |
| 2-5 | I-2 | and | (3-15) prothioconazole |
| 2-6 | I-2 | and | (3-17) tebuconazole |
| 2-7 | I-2 | and | (3-18) ipconazole |
| 2-8 | I-2 | and | (3-20) triticonazole |
| 2-9 | I-2 | and | (3-21) bitertanol |
| 2-10 | I-2 | and | (3-22) triadimenol |
| 2-11 | I-2 | and | (3-24) fluquinconazole |
| 2-12 | I-2 | and | (4-1) dichlofluanid |
| 2-13 | I-2 | and | (4-2) tolylfluanid |
| 2-14 | I-2 | and | (5-1) iprovalicarb |
| 2-15 | I-2 | and | (6-6) fenhexamid |
| 2-16 | I-2 | and | (6-7) carpropamid |
| 2-17 | I-2 | and | (6-9) fluopicolid |
| 2-18 | I-2 | and | (6-11) isotianil |
| 2-19 | I-2 | and | (6-14) penthiopyrad |
| 2-20 | I-2 | and | (6-17) flutolanil |
| 2-21 | I-2 | and | (6-18) N-[2-(1,3-dimethylbutyl)phenyl]-5-fluoro-1,3-dimethyl-1H-pyrazole-4-carboxamide |
| 2-22 | I-2 | and | (6-25) fluopyram |
| 2-23 | I-2 | and | (7-4) propineb |
| 2-24 | I-2 | and | (7-5) thiram |
| 2-25 | I-2 | and | (8-3) metalaxyl |
| 2-26 | I-2 | and | (8-4) metalaxyl-M |
| 2-27 | I-2 | and | (8-5) benalaxyl-M |
| 2-28 | I-2 | and | (9-3) pyrimethanil |
| 2-29 | I-2 | and | (10-3) carbendazim |
| 2-30 | I-2 | and | (11-2) propamocarb |
| 2-31 | I-2 | and | (11-4) propamocarb-fosetyl |
| 2-32 | I-2 | and | (11-5) pyribencarb |
| 2-33 | I-2 | and | (12-4) iprodione |
| 2-34 | I-2 | and | (14-2) prochloraz |
| 2-35 | I-2 | and | (14-3) triazoxide |
| 2-36 | I-2 | and | (14-5) fenamidone |
| 2-37 | I-2 | and | (16-2) fludioxonil |
| 2-38 | I-2 | and | (17-1) fosetyl-Al |
| 2-39 | I-2 | and | (17-3) tolclofos-methyl |
| 2-40 | I-2 | and | (19-10) spiroxamine |
| 2-41 | I-2 | and | (19-21) cyprosulfamide |
| 2-42 | I-2 | and | (19-22) mandipropamid |
| 2-43 | I-2 | and | (20-1) pencycuron |
| 2-44 | I-2 | and | (22-4) 5-chloro-6-(2,4,6-trifluorophenyl)-7-(4-methylpiperidin-1-yl)[1,2,4]triazolo[1,5-a]pyrimidine |
| 2-45 | I-2 | and | (24-1) N-(3',4'-dichloro-5-fluoro-1,1'-biphenyl-2-yl)-3-(difluoromethyl)-1-methyl-1H-pyrazole-4-carboxamide |
| 2-46 | I-2 | and | (24-9) bixafen |
| 2-47 | I-2 | and | (25-1) amisulbrom |

Furthermore, the combinations listed in Table 3 are obtained, where each combination per se is a preferred embodiment of the invention.

| No. of the active compound combination | Compound of the formula I | | Active compound of groups 2 to 27 |
|---|---|---|---|
| 3-1 | I-3 | and | (2-1) azoxystrobin |
| 3-2 | I-3 | and | (2-2) fluoxastrobin |
| 3-3 | I-3 | and | (2-3) (2E)-2-(2-{[6-(3-chloro-2-methylphenoxy)-5-fluoro-4-pyrimidinyl]oxy}phenyl)-2-(methoxyimino)-N-methylethanamide |
| 3-4 | I-3 | and | (2-4) trifloxystrobin |
| 3-5 | I-3 | and | (3-15) prothioconazole |
| 3-6 | I-3 | and | (3-17) tebuconazole |
| 3-7 | I-3 | and | (3-18) ipconazole |
| 3-8 | I-3 | and | (3-20) triticonazole |
| 3-9 | I-3 | and | (3-21) bitertanol |
| 3-10 | I-3 | and | (3-22) triadimenol |
| 3-11 | I-3 | and | (3-24) fluquinconazole |
| 3-12 | I-3 | and | (4-1) dichlofluanid |
| 3-13 | I-3 | and | (4-2) tolylfluanid |
| 3-14 | I-3 | and | (5-1) iprovalicarb |
| 3-15 | I-3 | and | (6-6) fenhexamid |
| 3-16 | I-3 | and | (6-7) carpropamid |
| 3-17 | I-3 | and | (6-9) fluopicolid |
| 3-18 | I-3 | and | (6-11) isotianil |
| 3-19 | I-3 | and | (6-14) penthiopyrad |
| 3-20 | I-3 | and | (6-17) flutolanil |
| 3-21 | I-3 | and | (6-18) N-[2-(1,3-dimethylbutyl)phenyl]-5-fluoro-1,3-dimethyl-1H-pyrazole-4-carboxamide |
| 3-22 | I-3 | and | (6-25) fluopyram |
| 3-23 | I-3 | and | (7-4) propineb |
| 3-24 | I-3 | and | (7-5) thiram |
| 3-25 | I-3 | and | (8-3) metalaxyl |
| 3-26 | I-3 | and | (8-4) metalaxyl-M |
| 3-27 | I-3 | and | (8-5) benalaxyl-M |
| 3-28 | I-3 | and | (9-3) pyrimethanil |
| 3-29 | I-3 | and | (10-3) carbendazim |
| 3-30 | I-3 | and | (11-2) propamocarb |
| 3-31 | I-3 | and | (11-4) propamocarb-fosetyl |
| 3-32 | I-3 | and | (11-5) pyribencarb |
| 3-33 | I-3 | and | (12-4) iprodione |
| 3-34 | I-3 | and | (14-2) prochloraz |
| 3-35 | I-3 | and | (14-3) triazoxide |
| 3-36 | I-3 | and | (14-5) fenamidone |
| 3-37 | I-3 | and | (16-2) fludioxonil |
| 3-38 | I-3 | and | (17-1) fosetyl-Al |
| 3-39 | I-3 | and | (17-3) tolclofos-methyl |
| 3-40 | I-3 | and | (19-10) spiroxamine |
| 3-41 | I-3 | and | (19-21) cyprosulfamide |

Active compound combination comprising

| No. of the active compound combination | Compound of the formula I | | Active compound of groups 2 to 27 |
|---|---|---|---|
| 3-42 | I-3 | and | (19-22) mandipropamid |
| 3-43 | I-3 | and | (20-1) pencycuron |
| 3-44 | I-3 | and | (22-4) 5-chloro-6-(2,4,6-trifluorophenyl)-7-(4-methylpiperidin-1-yl)[1,2,4]triazolo[1,5-a]pyrimidine |
| 3-45 | I-3 | and | (24-1) N-(3',4'-dichloro-5-fluoro-1,1'-biphenyl-2-yl)-3-(difluoromethyl)-1-methyl-1H-pyrazole-4-carboxamide |
| 3-46 | I-3 | and | (24-9) bixafen |
| 3-47 | I-3 | and | (25-1) amisulbrom |

Furthermore, the combinations listed in Table 4 are obtained, where each combination per se is a preferred embodiment of the invention.

Active compound combination comprising

| No. of the active compound combination | Compound of the formula I | | Active compound of groups 2 to 27 |
|---|---|---|---|
| 4-1 | I-4 | and | (2-1) azoxystrobin |
| 4-2 | I-4 | and | (2-2) fluoxastrobin |
| 4-3 | I-4 | and | (2-3) (2E)-2-(2-{[6-(3-chloro-2-methylphenoxy)-5-fluoro-4-pyrimidinyl]oxy}phenyl)-2-(methoxyimino)-N-methylethanamide |
| 4-4 | I-4 | and | (2-4) trifloxystrobin |
| 4-5 | I-4 | and | (3-15) prothioconazole |
| 4-6 | I-4 | and | (3-17) tebuconazole |
| 4-7 | I-4 | and | (3-18) ipconazole |
| 4-8 | I-4 | and | (3-20) triticonazole |
| 4-9 | I-4 | and | (3-21) bitertanol |
| 4-10 | I-4 | and | (3-22) triadimenol |
| 4-11 | I-4 | and | (3-24) fluquinconazole |
| 4-12 | I-4 | and | (4-1) dichlofluanid |
| 4-13 | I-4 | and | (4-2) tolylfluanid |
| 4-14 | I-4 | and | (5-1) iprovalicarb |
| 4-15 | I-4 | and | (6-6) fenhexamid |
| 4-16 | I-4 | and | (6-7) carpropamid |
| 4-17 | I-4 | and | (6-9) fluopicolid |
| 4-18 | I-4 | and | (6-11) isotianil |
| 4-19 | I-4 | and | (6-14) penthiopyrad |
| 4-20 | I-4 | and | (6-17) flutolanil |
| 4-21 | I-4 | and | (6-18) N-[2-(1,3-dimethylbutyl)phenyl]-5-fluoro-1,3-dimethyl-1H-pyrazole-4-carboxamide |
| 4-22 | I-4 | and | (6-25) fluopyram |
| 4-23 | I-4 | and | (7-4) propineb |
| 4-24 | I-4 | and | (7-5) thiram |
| 4-25 | I-4 | and | (8-3) metalaxyl |
| 4-26 | I-4 | and | (8-4) metalaxyl-M |
| 4-27 | I-4 | and | (8-5) benalaxyl-M |
| 4-28 | I-4 | and | (9-3) pyrimethanil |
| 4-29 | I-4 | and | (10-3) carbendazim |
| 4-30 | I-4 | and | (11-2) propamocarb |
| 4-31 | I-4 | and | (11-4) propamocarb fosetyl |
| 4-32 | I-4 | and | (11-5) pyribencarb |
| 4-33 | I-4 | and | (12-4) iprodione |
| 4-34 | I-4 | and | (14-2) prochloraz |
| 4-35 | I-4 | and | (14-3) triazoxide |
| 4-36 | I-4 | and | (14-5) fenamidone |
| 4-37 | I-4 | and | (16-2) fludioxonil |
| 4-38 | I-4 | and | (17-1) fosetyl-Al |
| 4-39 | I-4 | and | (17-3) tolclofos-methyl |
| 4-40 | I-4 | and | (19-10) spiroxamine |
| 4-41 | I-4 | and | (19-21) cyprosulfamide |
| 4-42 | I-4 | and | (19-22) mandipropamid |
| 4-43 | I-4 | and | (20-1) pencycuron |
| 4-44 | I-4 | and | (22-4) 5-chloro-6-(2,4,6-trifluorophenyl)-7-(4-methylpiperidin-1-yl)[1,2,4]triazolo[1,5-a]pyrimidine |
| 4-45 | I-4 | and | (24-1) N-(3',4'-dichloro-5-fluoro-1,1'-biphenyl-2-yl)-3-(difluoromethyl)-1-methyl-1H-pyrazole-4-carboxamide |
| 4-46 | I-4 | and | (24-9) bixafen |
| 4-47 | I-4 | and | (25-1) amisulbrom |

Furthermore, the combinations listed in Table 5 are obtained, where each combination per se is a preferred embodiment of the invention.

Active compound combination comprising

| No. of the active compound combination | Compound of the formula I | | Active compound of groups 2 to 27 |
|---|---|---|---|
| 5-1 | I-5 | and | (2-1) azoxystrobin |
| 5-2 | I-5 | and | (2-2) fluoxastrobin |
| 5-3 | I-5 | and | (2-3) (2E)-2-(2-{[6-(3-chloro-2-methylphenoxy)-5-fluoro-4-pyrimidinyl]oxy}phenyl)-2-(methoxyimino)-N-methylethanamide |
| 5-4 | I-5 | and | (2-4) trifloxystrobin |
| 5-5 | I-5 | and | (3-15) prothioconazole |
| 5-6 | I-5 | and | (3-17) tebuconazole |
| 5-7 | I-5 | and | (3-18) ipconazole |
| 5-8 | I-5 | and | (3-20) triticonazole |
| 5-9 | I-5 | and | (3-21) bitertanol |
| 5-10 | I-5 | and | (3-22) triadimenol |
| 5-11 | I-5 | and | (3-24) fluquinconazole |
| 5-12 | I-5 | and | (4-1) dichlofluanid |
| 5-13 | I-5 | and | (4-2) tolylfluanid |
| 5-14 | I-5 | and | (5-1) iprovalicarb |
| 5-15 | I-5 | and | (6-6) fenhexamid |
| 5-16 | I-5 | and | (6-7) carpropamid |
| 5-17 | I-5 | and | (6-9) fluopicolid |
| 5-18 | I-5 | and | (6-11) isotianil |
| 5-19 | I-5 | and | (6-14) penthiopyrad |
| 5-20 | I-5 | and | (6-17) flutolanil |
| 5-21 | I-5 | | (6-18) N-[2-(1,3-dimethylbutyl)phenyl]-5-fluoro-1,3-dimethyl-1H-pyrazole-4-carboxamide |
| 5-22 | I-5 | | (6-25) fluopyram |
| 5-23 | I-5 | | (7-4) propineb |
| 5-24 | I-5 | and | (7-5) thiram |
| 5-25 | I-5 | and | (8-3) metalaxyl |
| 5-26 | I-5 | and | (8-4) metalaxyl-M |
| 5-27 | I-5 | and | (8-5) benalaxyl-M |
| 5-28 | I-5 | and | (9-3) pyrimethanil |
| 5-29 | I-5 | and | (10-3) carbendazim |
| 5-30 | I-5 | and | (11-2) propamocarb |
| 5-31 | I-5 | and | (11-4) propamocarb fosetyl |
| 5-32 | I-5 | and | (11-5) pyribencarb |
| 5-33 | I-5 | and | (12-4) iprodione |
| 5-34 | I-5 | and | (14-2) prochloraz |
| 5-35 | I-5 | and | (14-3) triazoxide |
| 5-36 | I-5 | and | (14-5) fenamidone |
| 5-37 | I-5 | and | (16-2) fludioxonil |

-continued

| No. of the active compound combination | Compound of the formula I | | Active compound of groups 2 to 27 |
|---|---|---|---|
| 5-38 | I-5 | and | (17-1) fosetyl-Al |
| 5-39 | I-5 | and | (17-3) tolclofos-methyl |
| 5-40 | I-5 | and | (19-10) spiroxamine |
| 5-41 | I-5 | and | (19-21) cyprosulfamide |
| 5-42 | I-5 | and | (19-22) mandipropamid |
| 5-43 | I-5 | and | (20-1) pencycuron |
| 5-44 | I-5 | and | (22-4) 5-chloro-6-(2,4,6-trifluorophenyl)-7-(4-methylpiperidin-1-yl)[1,2,4]triazolo[1,5-a]pyrimidine |
| 5-45 | I-5 | and | (24-1) N-(3',4'-dichloro-5-fluoro-1,1'-biphenyl-2-yl)-3-(difluoromethyl)-1-methyl-1H-pyrazole-4-carboxamide |
| 5-46 | I-5 | and | (24-9) bixafen |
| 5-47 | I-5 | and | (25-1) amisulbrom |

Furthermore, the combinations listed in Table 6 are obtained, where each combination per se is a preferred embodiment of the invention.

| No. of the active compound combination | Compound of the formula I | | Active compound of groups 2 to 27 |
|---|---|---|---|
| 6-1 | I-6 | and | (2-1) azoxystrobin |
| 6-2 | I-6 | and | (2-2) fluoxastrobin |
| 6-3 | I-6 | and | (2-3) (2E)-2-(2-{[6-(3-chloro-2-methylphenoxy)-5-fluoro-4-pyrimidinyl]oxy}phenyl)-2-(methoxyimino)-N-methylethanamide |
| 6-4 | I-6 | and | (2-4) trifloxystrobin |
| 6-5 | I-6 | and | (3-15) prothioconazole |
| 6-6 | I-6 | and | (3-17) tebuconazole |
| 6-7 | I-6 | and | (3-18) ipconazole |
| 6-8 | I-6 | and | (3-20) triticonazole |
| 6-9 | I-6 | and | (3-21) bitertanol |
| 6-10 | I-6 | | (3-22) triadimenol |
| 6-11 | I-6 | | (3-24) fluquinconazole |
| 6-12 | I-6 | | (4-1) dichlofluanid |
| 6-13 | I-6 | and | (4-2) tolylfluanid |
| 6-14 | I-6 | and | (5-1) iprovalicarb |
| 6-15 | I-6 | and | (6-6) fenhexamid |
| 6-16 | I-6 | and | (6-7) carpropamid |
| 6-17 | I-6 | and | (6-9) fluopicolid |
| 6-18 | I-6 | and | (6-11) isotianil |
| 6-19 | I-6 | and | (6-14) penthiopyrad |
| 6-20 | I-6 | and | (6-17) flutolanil |
| 6-21 | I-6 | and | (6-18) N-[2-(1,3-dimethylbutyl)phenyl]-5-fluoro-1,3-dimethyl-1H-pyrazole-4-carboxamide |
| 6-22 | I-6 | and | (6-25) fluopyram |
| 6-23 | I-6 | and | (7-4) propineb |
| 6-24 | I-6 | and | (7-5) thiram |
| 6-25 | I-6 | and | (8-3) metalaxyl |
| 6-26 | I-6 | and | (8-4) metalaxyl-M |
| 6-27 | I-6 | and | (8-5) benalaxyl-M |
| 6-28 | I-6 | and | (9-3) pyrimethanil |
| 6-29 | I-6 | and | (10-3) carbendazim |
| 6-30 | I-6 | and | (11-2) propamocarb |
| 6-31 | I-6 | and | (11-4) propamocarb fosetyl |
| 6-32 | I-6 | and | (11-5) pyribencarb |
| 6-33 | I-6 | and | (12-4) iprodione |
| 6-34 | I-6 | and | (14-2) prochloraz |
| 6-35 | I-6 | and | (14-3) triazoxide |
| 6-36 | I-6 | and | (14-5) fenamidone |
| 6-37 | I-6 | and | (16-2) fludioxonil |
| 6-38 | I-6 | and | (17-1) fosetyl-Al |
| 6-39 | I-6 | and | (17-3) tolclofos-methyl |
| 6-40 | I-6 | and | (19-10) spiroxamine |
| 6-41 | I-6 | and | (19-21) cyprosulfamide |
| 6-42 | I-6 | and | (19-22) mandipropamid |
| 6-43 | I-6 | and | (20-1) pencycuron |
| 6-44 | I-6 | and | (22-4) 5-chloro-6-(2,4,6-trifluorophenyl)-7-(4-methylpiperidin-1-yl)[1,2,4]triazolo[1,5-a]pyrimidine |
| 6-45 | I-6 | and | (24-1) N-(3',4'-dichloro-5-fluoro-1,1'-biphenyl-2-yl)-3-(difluoromethyl)-1-methyl-1H-pyrazole-4-carboxamide |
| 6-46 | I-6 | and | (24-9) bixafen |
| 6-47 | I-6 | and | (25-1) amisulbrom |

Furthermore, the combinations listed in Table 7 are obtained, where each combination per se is a preferred embodiment of the invention.

| No. of the active compound combination | Compound of the formula I | | Active compound of groups 2 to 27 |
|---|---|---|---|
| 7-1 | I-7 | and | (2-1) azoxystrobin |
| 7-2 | I-7 | and | (2-2) fluoxastrobin |
| 7-3 | I-7 | and | (2-3) (2E)-2-(2-{[6-(3-chloro-2-methylphenoxy)-5-fluoro-4-pyrimidinyl]oxy}phenyl)-2-(methoxyimino)-N-methylethanamide |
| 7-4 | I-7 | and | (2-4) trifloxystrobin |
| 7-5 | I-7 | and | (3-15) prothioconazole |
| 7-6 | I-7 | and | (3-17) tebuconazole |
| 7-7 | I-7 | and | (3-18) ipconazole |
| 7-8 | I-7 | and | (3-20) triticonazole |
| 7-9 | I-7 | and | (3-21) bitertanol |
| 7-10 | I-7 | and | (3-22) triadimenol |
| 7-11 | I-7 | and | (3-24) fluquinconazole |
| 7-12 | I-7 | and | (4-1) dichlofluanid |
| 7-13 | I-7 | and | (4-2) tolylfluanid |
| 7-14 | I-7 | and | (5-1) iprovalicarb |
| 7-15 | I-7 | and | (6-6) fenhexamid |
| 7-16 | I-7 | and | (6-7) carpropamid |
| 7-17 | I-7 | and | (6-9) fluopicolid |
| 7-18 | I-7 | and | (6-11) isotianil |
| 7-19 | I-7 | and | (6-14) penthiopyrad |
| 7-20 | I-7 | and | (6-17) flutolanil |
| 7-21 | I-7 | and | (6-18) N-[2-(1,3-dimethylbutyl)phenyl]-5-fluoro-1,3-dimethyl-1H-pyrazole-4-carboxamide |
| 7-22 | I-7 | and | (6-25) fluopyram |
| 7-23 | I-7 | and | (7-4) propineb |
| 7-24 | I-7 | and | (7-5) thiram |
| 7-25 | I-7 | and | (8-3) metalaxyl |
| 7-26 | I-7 | and | (8-4) metalaxyl-M |
| 7-27 | I-7 | and | (8-5) benalaxyl-M |
| 7-28 | I-7 | and | (9-3) pyrimethanil |
| 7-29 | I-7 | and | (10-3) carbendazim |
| 7-30 | I-7 | and | (11-2) propamocarb |
| 7-31 | I-7 | and | (11-4) propamocarb fosetyl |

-continued

Active compound combination comprising

| No. of the active compound combination | Compound of the formula I | | Active compound of groups 2 to 27 |
|---|---|---|---|
| 7-32 | I-7 | and | (11-5) pyribencarb |
| 7-33 | I-7 | and | (12-4) iprodione |
| 7-34 | I-7 | and | (14-2) prochloraz |
| 7-35 | I-7 | and | (14-3) triazoxide |
| 7-36 | I-7 | and | (14-5) fenamidone |
| 7-37 | I-7 | and | (16-2) fludioxonil |
| 7-38 | I-7 | and | (17-1) fosetyl-Al |
| 7-39 | I-7 | and | (17-3) tolclofos-methyl |
| 7-40 | I-7 | and | (19-10) spiroxamine |
| 7-41 | I-7 | and | (19-21) cyprosulfamide |
| 7-42 | I-7 | and | (19-22) mandipropamid |
| 7-43 | I-7 | and | (20-1) pencycuron |
| 7-44 | I-7 | and | (22-4) 5-chloro-6-(2,4,6-trifluorophenyl)-7-(4-methylpiperidin-1-yl)[1,2,4]triazolo[1,5-a]pyrimidine |
| 7-45 | I-7 | and | (24-1) N-(3',4'-dichloro-5-fluoro-1,1'-biphenyl-2-yl)-3-(difluoromethyl)-1-methyl-1H-pyrazole-4-carboxamide |
| 7-46 | I-7 | and | (24-9) bixafen |
| 7-47 | I-7 | and | (25-1) amisulbrom |

Furthermore, the combinations listed in Table 8 are obtained, where each combination per se is a preferred embodiment of the invention.

Active compound combination comprising

| No. of the active compound combination | Compound of the formula I | | Active compound of groups 2 to 27 |
|---|---|---|---|
| 8-1 | I-8 | and | (2-1) azoxystrobin |
| 8-2 | I-8 | and | (2-2) fluoxastrobin |
| 8-3 | I-8 | and | (2-3) (2E)-2-(2-{[6-(3-chloro-2-methylphenoxy)-5-fluoro-4-pyrimidinyl]oxy}phenyl)-2-(methoxyimino)-N-methylethanamide |
| 8-4 | I-8 | and | (2-4) trifloxystrobin |
| 8-5 | I-8 | and | (3-15) prothioconazole |
| 8-6 | I-8 | and | (3-17) tebuconazole |
| 8-7 | I-8 | and | (3-18) ipconazole |
| 8-8 | I-8 | and | (3-20) triticonazole |
| 8-9 | I-8 | and | (3-21) bitertanol |
| 8-10 | I-8 | and | (3-22) triadimenol |
| 8-11 | I-8 | and | (3-24) fluquinconazole |
| 8-12 | I-8 | and | (4-1) dichlofluanid |
| 8-13 | I-8 | and | (4-2) tolylfluanid |
| 8-14 | I-8 | and | (5-1) iprovalicarb |
| 8-15 | I-8 | and | (6-6) fenhexamid |
| 8-16 | I-8 | and | (6-7) carpropamid |
| 8-17 | I-8 | and | (6-9) fluopicolid |
| 8-18 | I-8 | and | (6-11) isotianil |
| 8-19 | I-8 | and | (6-14) penthiopyrad |
| 8-20 | I-8 | and | (6-17) flutolanil |
| 8-21 | I-8 | and | (6-18) N-[2-(1,3-dimethylbutyl)phenyl]-5-fluoro-1,3-dimethyl-1H-pyrazole-4-carboxamide |
| 8-22 | I-8 | and | (6-25) fluopyram |
| 8-23 | I-8 | and | (7-4) propineb |
| 8-24 | I-8 | and | (7-5) thiram |
| 8-25 | I-8 | and | (8-3) metalaxyl |
| 8-26 | I-8 | and | (8-4) metalaxyl-M |
| 8-27 | I-8 | and | (8-5) benalaxyl-M |
| 8-28 | I-8 | and | (9-3) pyrimethanil |
| 8-29 | I-8 | and | (10-3) carbendazim |
| 8-30 | I-8 | and | (11-2) propamocarb |
| 8-31 | I-8 | and | (11-4) propamocarb fosetyl |
| 8-32 | I-8 | and | (11-5) pyribencarb |
| 8-33 | I-8 | and | (12-4) iprodione |
| 8-34 | I-8 | and | (14-2) prochloraz |
| 8-35 | I-8 | and | (14-3) triazoxide |
| 8-36 | I-8 | and | (14-5) fenamidone |
| 8-37 | I-8 | and | (16-2) fludioxonil |
| 8-38 | I-8 | and | (17-1) fosetyl-Al |
| 8-39 | I-8 | and | (17-3) tolclofos-methyl |
| 8-40 | I-8 | and | (19-10) spiroxamine |
| 8-41 | I-8 | and | (19-21) cyprosulfamide |
| 8-42 | I-8 | and | (19-22) mandipropamid |
| 8-43 | I-8 | and | (20-1) pencycuron |
| 8-44 | I-8 | and | (22-4) 5-chloro-6-(2,4,6-trifluorophenyl)-7-(4-methylpiperidin-1-yl)[1,2,4]triazolo[1,5-a]pyrimidine |
| 8-45 | I-8 | and | (24-1) N-(3',4'-dichloro-5-fluoro-1,1'-biphenyl-2-yl)-3-(difluoromethyl)-1-methyl-1H-pyrazole-4-carboxamide |
| 8-46 | I-8 | and | (24-9) bixafen |
| 8-47 | I-8 | and | (25-1) amisulbrom |

Embodiments of the invention which are emphasized for the treatment of seed are active compound combinations comprising the compound of the formula (I-1) and fluoxastrobin (2-2) and/or trifloxystrobin (2-4) and/or prothioconazole (3-15) and/or tebuconazole (3-17) and/or ipconazole (3-18) and/or triticonazole (3-20) and/or triadimenol (3-22) and/or carpropamid (6-7) and/or N-[2-(1,3-dimethylbutyl)phenyl]-5-fluoro-1,3-dimethyl-1H-pyrazole-4-carboxamide (6-18) and/or thiram (7-5) and/or metalaxyl (8-3) and/or metalaxyl-M (8-4) and/or N-({4-[(cyclopropylamino)carbonyl]phenyl}sulphonyl)-2-methoxybenzamide (19-21) and/or pencycuron (20-1) and/or N-(3',4'-dichloro-5-fluoro-1,1'-biphenyl-2-yl)-3-(difluoromethyl)-1-methyl-1H-pyrazole-4-carboxamide (24-1).

Embodiments of the invention which are emphasized for the treatment of seed are active compound combinations comprising the compound of the formula (I-2) and fluoxastrobin (2-2) and/or trifloxystrobin (2-4) and/or prothioconazole (3-15) and/or tebuconazole (3-17) and/or ipconazole (3-18) and/or triticonazole (3-20) and/or triadimenol (3-22) and/or carpropamid (6-7) and/or N-[2-(1,3-dimethylbutyl)phenyl]-5-fluoro-1,3-dimethyl-1H-pyrazole-4-carboxamide (6-18) and/or thiram (7-5) and/or metalaxyl (8-3) and/or metalaxyl-M (8-4) and/or N-({4-[(cyclopropylamino)carbonyl]phenyl}sulphonyl)-2-methoxybenzamide (19-21) and/or pencycuron (20-1) and/or N-(3',4'-dichloro-5-fluoro-1,1'-biphenyl-2-yl)-3-(difluoromethyl)-1-methyl-1H-pyrazole-4-carboxamide (24-1).

Embodiments of the invention which are emphasized for the treatment of seed are active compound combinations comprising the compound of the formula (I-3) and fluoxastrobin (2-2) and/or trifloxystrobin (2-4) and/or prothioconazole (3-15) and/or tebuconazole (3-17) and/or ipconazole (3-18) and/or triticonazole (3-20) and/or triadimenol (3-22) and/or carpropamid (6-7) and/or N-[2-(1,3-dimethylbutyl)phenyl]-5-fluoro-1,3-dimethyl-1H-pyrazole-4-carboxamide (6-18) and/or thiram (7-5) and/or metalaxyl (8-3) and/or metalaxyl-M (8-4) and/or N-({4-[(cyclopropylamino)carbonyl]phenyl}sulphonyl)-2-methoxybenzamide (19-21) and/or pencycuron (20-1) and/or N-(3',4'-dichloro-5-fluoro-1,1'-biphenyl-2-yl)-3-(difluoromethyl)-1-methyl-1H-pyrazole-4-carboxamide (24-1).

Embodiments of the invention which are emphasized for the treatment of seed are active compound combinations comprising the compound of the formula (I-4) and fluoxastrobin (2-2) and/or trifloxystrobin (2-4) and/or prothioconazole (3-15) and/or tebuconazole (3-17) and/or ipconazole (3-18) and/or triticonazole (3-20) and/or triadimenol (3-22) and/or carpropamid (6-7) and/or N-[2-(1,3-dimethylbutyl)phenyl]-5-fluoro-1,3-dimethyl-1H-pyrazole-4-carboxamide (6-18) and/or thiram (7-5) and/or metalaxyl (8-3) and/or metalaxyl-M (8-4) and/or N-({4-[(cyclopropylamino)carbonyl]phenyl}sulphonyl)-2-methoxybenzamide (19-21) and/or pencycuron (20-1) and/or N-(3',4'-dichloro-5-fluoro-1,1'-biphenyl-2-yl)-3-(difluoromethyl)-1-methyl-1H-pyrazole-4-carboxamide (24-1).

Embodiments of the invention which are emphasized for the treatment of seed are active compound combinations comprising the compound of the formula (I-5) and fluoxastrobin (2-2) and/or trifloxystrobin (2-4) and/or prothioconazole (3-15) and/or tebuconazole (3-17) and/or ipconazole (3-18) and/or triticonazole (3-20) and/or triadimenol (3-22) and/or carpropamid (6-7) and/or N-[2-(1,3-dimethylbutyl)phenyl]-5-fluoro-1,3-dimethyl-1H-pyrazole-4-carboxamide (6-18) and/or thiram (7-5) and/or metalaxyl (8-3) and/or metalaxyl-M (8-4) and/or N-({4-[(cyclopropylamino)carbonyl]phenyl}sulphonyl)-2-methoxybenzamide (19-21) and/or pencycuron (20-1) and/or N-(3',4'-dichloro-5-fluoro-1,1'-biphenyl-2-yl)-3-(difluoromethyl)-1-methyl-1H-pyrazole-4-carboxamide (24-1).

Embodiments of the invention which are emphasized for the treatment of seed are active compound combinations comprising the compound of the formula (I-6) and fluoxastrobin (2-2) and/or trifloxystrobin (2-4) and/or prothioconazole (3-15) and/or tebuconazole (3-17) and/or ipconazole (3-18) and/or triticonazole (3-20) and/or triadimenol (3-22) and/or carpropamid (6-7) and/or N-[2-(1,3-dimethylbutyl)phenyl]-5-fluoro-1,3-dimethyl-1H-pyrazole-4-carboxamide (6-18) and/or thiram (7-5) and/or metalaxyl (8-3) and/or metalaxyl-M (8-4) and/or N-({4-[(cyclopropylamino)carbonyl]phenyl}sulphonyl)-2-methoxybenzamide (19-21) and/or pencycuron (20-1) and/or N-(3',4'-dichloro-5-fluoro-1,1'-biphenyl-2-yl)-3-(difluoromethyl)-1-methyl-1H-pyrazole-4-carboxamide (24-1).

Embodiments of the invention which are emphasized for the treatment of seed are active compound combinations comprising the compound of the formula (I-7) and fluoxastrobin (2-2) and/or trifloxystrobin (2-4) and/or prothioconazole (3-15) and/or tebuconazole (3-17) and/or ipconazole (3-18) and/or triticonazole (3-20) and/or triadimenol (3-22) and/or carpropamid (6-7) and/or N-[2-(1,3-dimethylbutyl)phenyl]-5-fluoro-1,3-dimethyl-1H-pyrazole-4-carboxamide (6-18) and/or thiram (7-5) and/or metalaxyl (8-3) and/or metalaxyl-M (8-4) and/or N-({4-[(cyclopropylamino)carbonyl]phenyl}sulphonyl)-2-methoxybenzamide (19-21) and/or pencycuron (20-1) and/or N-(3',4'-dichloro-5-fluoro-1,1'-biphenyl-2-yl)-3-(difluoromethyl)-1-methyl-1H-pyrazole-4-carboxamide (24-1).

Embodiments of the invention which are emphasized for the treatment of seed are active compound combinations comprising the compound of the formula (I-8) and fluoxastrobin (2-2) and/or trifloxystrobin (2-4) and/or prothioconazole (3-15) and/or tebuconazole (3-17) and/or ipconazole (3-18) and/or triticonazole (3-20) and/or triadimenol (3-22) and/or carpropamid (6-7) and/or N-[2-(1,3-dimethylbutyl)phenyl]-5-fluoro-1,3-dimethyl-1H-pyrazole-4-carboxamide (6-18) and/or thiram (7-5) and/or metalaxyl (8-3) and/or metalaxyl-M (8-4) and/or N-({4-[(cyclopropylamino)carbonyl]phenyl}sulphonyl)-2-methoxybenzamide (19-21) and/or pencycuron (20-1) and/or N-(3',4'-dichloro-5-fluoro-1,1'-biphenyl-2-yl)-3-(difluoromethyl)-1-methyl-1H-pyrazole-4-carboxamide (24-1).

The active compound combinations according to the invention comprise, in addition to a compound of the formula (I), at least one active compound of groups (2) to (27). Moreover, they can additionally contain other fungicidally active components for admixture.

If the active compounds are present in the active compound combinations according to the invention in certain weight ratios, the synergistic effect is particularly pronounced. However, the weight ratios of the active compounds in the active compound combinations can be varied within a relatively wide range. In general, the combinations according to the invention comprise compounds of the formula (I) and a combination partner of one of the groups (2) to (27) in the mixing ratios given in an exemplary manner in the table below.

The mixing ratios are based on weight ratios. The ratio is to be understood as meaning compound of the formula (I): combination partner

| Combination partner | Preferred mixing ratio | Particularly preferred mixing ratio |
| --- | --- | --- |
| Group (2): strobilurins | 125:1 to 1:2000 | 50:1 to 1:1000 |
| Group (3): triazoles | 125:1 to 1:2000 | 50:1 to 1:1000 |
| Group (4): sulphonamides | 500:1 to 1:100 | 250:1 to 1:50 |
| Group (5): valinamides | 125:1 to 1:2000 | 50:1 to 1:1000 |
| Group (6): carboxamides excluding (6-6) | 125:1 to 1:2000 | 50:1 to 1:1000 |
| (6-6): | 500:1 to 1:100 | 250:1 to 1:25 |
| Group (7): dithiocarbamates | 500:1 to 1:100 | 250:1 to 1:25 |
| Group (8): acylalanines | 125:1 to 1:2000 | 50:1 to 1:1000 |
| Group (9): anilinopyrimidines | 500:1 to 1:100 | 250:1 to 1:25 |
| Group (10): benzimidazoles | 125:1 to 1:2000 | 50:1 to 1:1000 |
| Group (11): carbamates | 500:1 to 1:100 | 250:1 to 1:25 |
| Group (12): dicarboximides | 500:1 to 1:100 | 250:1 to 1:25 |
| Group (13): guanidines | 125:1 to 1:2000 | 50:1 to 1:1000 |
| Group (14): imidazoles | 125:1 to 1:2000 | 50:1 to 1:1000 |
| Group (15): morpholines | 125:1 to 1:2000 | 50:1 to 1:1000 |
| Group (16): pyrroles | 125:1 to 1:2000 | 50:1 to 1:1000 |
| Group (17): (thio)phosphonates | 500:1 to 1:100 | 250:1 to 1:25 |
| Group (18): phenylethanamides | 125:1 to 1:2000 | 50:1 to 1:1000 |
| (19-1): acibenzolar-S-methyl | 125:1 to 1:2000 | 50:1 to 1:1000 |
| (19-2): chlorothalonil | 500:1 to 1:100 | 250:1 to 1:25 |
| (19-3): cymoxanil | 125:1 to 1:2000 | 50:1 to 1:1000 |
| (19-4): edifenphos | 125:1 to 1:2000 | 50:1 to 1:1000 |
| (19-5): famoxadone | 125:1 to 1:2000 | 50:1 to 1:1000 |
| (19-6): fluazinam | 125:1 to 1:2000 | 50:1 to 1:1000 |
| (19-7): copper oxychloride | 500:1 to 1:100 | 250:1 to 1:25 |
| (19-8): copper hydroxide | 500:1 to 1:100 | 250:1 to 1:25 |
| (19-9): oxadixyl | 125:1 to 1:2000 | 50:1 to 1:1000 |
| (19-10): spiroxamine | 125:1 to 1:2000 | 50:1 to 1:1000 |
| (19-11) dithianon | 500:1 to 1:100 | 250:1 to 1:25 |
| (19-12) metrafenone | 125:1 to 1:2000 | 50:1 to 1:1000 |
| (19-14): 2,3-dibutyl-6-chlorothieno[2,3-d]pyrimidin-4(3H)one | 125:1 to 1:2000 | 50:1 to 1:1000 |
| (19-15): probenazole | 125:1 to 1:2000 | 50:1 to 1:1000 |
| (19-16): isoprothiolane | 125:1 to 1:2000 | 50:1 to 1:1000 |
| (19-17): kasugamycin | 125:1 to 1:2000 | 50:1 to 1:1000 |
| (19-18): phthalide | 125:1 to 1:2000 | 50:1 to 1:1000 |
| (19-19): ferimzone | 125:1 to 1:2000 | 50:1 to 1:1000 |
| (19-20): tricyclazole | 125:1 to 1:2000 | 50:1 to 1:1000 |
| (19-21): cyprosulfamide | 125:1 to 1:2000 | 50:1 to 1:1000 |
| (19-22) 2-(4-chlorophenyl)-N-{2-[3-methoxy-4-(prop-2-yn-1-yloxy)phenyl]ethyl}-2-(prop-2-yn-1-yloxy)acetamide | 125:1 to 1:2000 | 50:1 to 1:1000 |
| Group (20): (thio)urea derivatives | 125:1 to 1:2000 | 50:1 to 1:1000 |
| Group (21): amides | 125:1 to 1:2000 | 50:1 to 1:1000 |

| Combination partner | Preferred mixing ratio | Particularly preferred mixing ratio |
|---|---|---|
| Group (22): triazolopyrimidines | 125:1 to 1:2000 | 50:1 to 1:1000 |
| Group (23): iodochromones | 125:1 to 1:2000 | 50:1 to 1:1000 |
| Group (24): biphenylcarboxamides | 125:1 to 1:2000 | 50:1 to 1:1000 |

The compounds of the formula (I) or the active compounds from groups (2) to (27) listed above with at least one basic centre are capable of forming, for example, acid addition salts, for example with strong inorganic acids such as mineral acids, for example perchloric acid, sulphuric acid, nitric acid, nitrous acid, a phosphorus acid or a hydrohalic acid, with strong organic carboxylic acids such as unsubstituted or substituted, for example halogen-substituted, $C_1$-$C_4$-alkanecarboxylic acids, for example acetic acid, saturated or unsaturated dicarboxylic acids, for example oxalic acid, malonic acid, succinic acid, maleic acid, fumaric acid and phthalic acid, hydroxycarboxylic acids, for example ascorbic acid, lactic acid, malic acid, tartaric acid and citric acid, or benzoic acid, or with organic sulphonic acids such as unsubstituted or substituted, for example halogen-substituted, $C_1$-$C_4$-alkane or arylsulphonic acids, for example methane or p-toluenesulphonic acid. The compounds of the formula (I) or the active compounds from groups (2) to (27) listed above with at least one acidic group are capable of forming, for example, salts with bases, for example metal salts, such as alkali or alkaline-earth metal salts, for example sodium, potassium or magnesium salts, or salts with ammonia or an organic amine such as morpholine, piperidine, pyrrolidine, a lower mono, di or trialkylamine, for example, ethyl, diethyl, triethyl or dimethylpropylamine, or a lower mono, di or trihydroxyalkylamine, for example mono, di or triethanolamine. Moreover, if appropriate, it may also be possible for corresponding internal salts to be formed. In the context of the invention, agrochemically advantageous salts are preferred. With a view to the close relationship between the compounds of the formula (I) or the active compounds from groups (2) to (27) listed above in free form and in the form of their salts, each reference above and below to the free compounds of the formula (I) or to free active compounds from groups (2) to (27) listed above or to their salts is meant to be understood such that this also includes the corresponding salts and the free compounds of the formula (I) or the free active compounds from groups (2) to (27) listed above, respectively, if this is applicable and expedient. This also applies in a corresponding manner to tautomers of the compounds of the formula (I) and the active compounds from groups (2) to (27) listed above and to their salts.

In the context of the present invention, the term "active compound combination" refers to various combinations of compounds of the formula (I) and active compounds from groups (2) to (27) listed above, for example in the form of a single ready-mix, in a combined spray mixture composed of separate formulations of the individual active compounds, for example a tank-mix or in a combined use of the individual active compounds in the case of their sequential application, for example in succession within an appropriate short period of time of, for example, a few hours or days. According to a preferred embodiment, the order of the application of the compounds of the formula (I) and the active compounds from groups (2) to (27) listed above is not critical for the practice of the present invention.

When using the active compound combinations according to the invention as fungicides, insecticides or acaricides, the application rates can be varied within a relatively wide range, depending on the kind of application. The application rate of the active compound combinations according to the invention is when treating plant parts, e.g. leaves: from 0.1 to 10,000 g/ha, preferably from 10 to 1,000 g/ha, particularly preferably from 50 to 300 g/ha (when the application is carried out by watering or dripping, it may even be possible to reduce the application rate, in particular when inert substrates such as rock wool or perlite are used); when treating seed: from 2 to 200 g per 100 kg of seed, preferably from 3 to 150 g per 100 kg of seed, particularly preferably from 2.5 to 25 g per 100 kg of seed, very particularly preferably from 2.5 to 12.5 g per 100 kg of seed; when treating the soil: from 0.1 to 10,000 g/ha, preferably from 1 to 5,000 g/ha.

These application rates are mentioned only by way of example and are not limiting in the sense of the invention.

The active compound combinations according to the invention can be employed for protecting plants for a certain period of time after treatment against attack by phytopathogenic fungi and/or animal pests. The period for which protection is provided extends generally for 1 to 28 days, preferably for 1 to 14 days, particularly preferably for 1 to 10 days, very particularly preferably for 1 to 7 days after the treatment of the plants with the active compounds, or for up to 200 days after a seed treatment.

The active compound combinations according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling phytopathogenic fungi such as Plasmodiophoromycetes, Oomycetes, Chytridiomycetes, Zygomycetes, Ascomycetes, Basidiomycetes, Deuteromycetes etc. and animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection compositions. They are active against normally sensitive and resistant species and against all or some stages of development.

The active compound combinations according to the invention have a very good fungicidal activity and can be employed for controlling phytopathogenic fungi such as Plasmodiophoromycetes, Oomycetes, Chytridiomycetes, Zygomycetes, Ascomycetes, Basidiomycetes, Deuteromycetes and the like.

The active compound combinations according to the invention are particularly suitable for controlling *Phytophthora infestans, Plasmopara viticola* and *Botrytis cinerea*.

Some pathogens causing fungal and bacterial diseases which come under the generic names listed above may be mentioned as examples, but not by way of limitation:

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

diseases caused by powdery mildew pathogens, such as, for example,

Blumeria species, such as, for example, Blumeria graminis;

Podosphaera species, for example Podosphaera leucotricha;

Sphaerotheca species, for example Sphaerotheca fuliginea;

Uncinula species, such as, for example, Uncinula necator;

diseases caused by rust disease pathogens, such as, for example,

Gymnosporangium species, such as, for example, Gymnosporangium sabinae

Hemileia species, such as, for example, Hemileia vastatrix;

Phakopsora species, such as, for example, Phakopsora pachyrhizi and Phakopsora meibomiae;

Puccinia species, such as, for example, Puccinia recondita;

Uromyces species, such as, for example, Uromyces appendiculatus;

diseases caused by pathogens from the group of the Oomycetes, such as, for example, Bremia species, such as, for example, Bremia lactucae;

Peronospora species, such as, for example, Peronospora pisi or P. brassicae;

Phytophthora species, such as, for example, Phytophthora infestans;

Plasmopara species, such as, for example, Plasmopara viticola;

Pseudoperonospora species, such as, for example, Pseudoperonospora humuli or

Pseudoperonospora cubensis;

Pythium species, such as, for example, Pythium ultimum;

leaf blotch diseases and leaf wilt diseases caused, for example, by

Alternaria species, such as, for example, Alternaria solani;

Cercospora species, such as, for example, Cercospora beticola;

Cladiosporum species, such as, for example, Cladiosporium cucumerinum;

Cochliobolus species, such as, for example, Cochliobolus sativus (conidia form: Drechslera, syn: Helminthosporium);

Colletotrichum species, such as, for example, Colletotrichum lindemuthanium;

Cycloconium species, such as, for example, Cycloconium oleaginum;

Diaporthe species, such as, for example, Diaporthe citri;

Elsinoe species, such as, for example, Elsinoe fawcettii;

Gloeosporium species, such as, for example, Gloeosporium laeticolor;

Glomerella species, such as, for example, Glomerella cingulata;

Guignardia species, such as, for example, Guignardia bidwelli;

Leptosphaeria species, such as, for example, Leptosphaeria maculans;

Magnaporthe species, such as, for example, Magnaporthe grisea;

Mycosphaerella species, such as, for example, Mycosphaerelle graminicola;

Phaeosphaeria species, such as, for example, Phaeosphaeria nodorum;

Pyrenophora species, such as, for example, Pyrenophora teres;

Ramularia species, such as, for example, Ramularia collocygni;

Rhynchosporium species, such as, for example, Rhynchosporium secalis;

Septoria species, such as, for example, Septoria apii;

Typhula species, such as, for example, Typhula incarnata;

Venturia species, such as, for example, Venturia inaequalis;

root and stem diseases caused, for example, by

Corticium species, such as, for example, Corticium graminearum;

Fusarium species, such as, for example, Fusarium oxysporum;

Gaeumannomyces species, such as, for example, Gaeumannomyces graminis;

Rhizoctonia species, such as, for example, Rhizoctonia solani;

Tapesia species, such as, for example, Tapesia acuformis;

Thielaviopsis species, such as, for example, Thielaviopsis basicola;

ear and panicle diseases (including corn cobs) caused, for example, by

Alternaria species, such as, for example, Alternaria spp.;

Aspergillus species, such as, for example, Aspergillus flavus;

Cladosporium species, such as, for example, Cladosporium spp.;

Claviceps species, such as, for example, Claviceps purpurea;

Fusarium species, such as, for example, Fusarium culmorum;

Gibberella species, such as, for example, Gibberella zeae;

Monographella species, such as, for example, Monographella nivalis;

diseases caused by smut fungi, such as, for example,

Sphacelotheca species, such as, for example, Sphacelotheca reiliana;

Tilletia species, such as, for example, Tilletia caries;

Urocystis species, such as, for example, Urocystis occulta;

Ustilago species, such as, for example, Ustilago nuda;

fruit rot caused, for example, by

Aspergillus species, such as, for example, Aspergillus flavus;

Botrytis species, such as, for example, Botrytis cinerea;

Penicillium species, such as, for example, Penicillium expansum;

Sclerotinia species, such as, for example, Sclerotinia sclerotiorum;

Verticilium species, such as, for example, Verticilium alboatrum;

seed- and soil-borne rot and wilt diseases, and also diseases of seedlings, caused, for example, by Fusarium species, such as, for example, Fusarium culmorum;

Phytophthora species, such as, for example, Phytophthora cactorum;

Pythium species, such as, for example, Pythium ultimum;

Rhizoctonia species, such as, for example, Rhizoctonia solani;

Sclerotium species, such as, for example, Sclerotium rolfsii;

cancerous diseases, galls and witches' broom caused, for example, by

Nectria species, such as, for example, Nectria galligena;

wilt diseases caused, for example, by

Monilinia species, such as, for example, Monilinia laxa;

deformations of leaves, flowers and fruits caused, for example, by

*Taphrina* species, such as, for example, *Taphrina deformans*;

degenerative diseases of woody plants caused, for example, by

Esca species, such as, for example, *Phaemoniella clamydospora*;

diseases of flowers and seeds caused, for example, by

*Botrytis* species, such as, for example, *Botrytis cinerea*;

diseases of plant tubers caused, for example, by

*Rhizoctonia* species, such as, for example, *Rhizoctonia solani*;

diseases caused by bacterial pathogens, such as, for example,

*Xanthomonas* species, such as, for example, *Xanthomonas campestris* pv. *oryzae*;

*Pseudomonas* species, such as, for example, *Pseudomonas syringae* pv. *lachrymans*;

*Erwinia* species, such as, for example, *Erwinia amylovora*;

Preference is given to controlling the following diseases of soya beans:

fungal diseases on leaves, stems, pods and seeds caused, for example, by alternaria leaf spot (*Alternaria* spec. atrans tenuissima), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (Dactuliophora glycines), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (Phyllosticta sojaecola), powdery mildew (Microsphaera diffusa), pyrenochaeta leaf spot (Pyrenochaeta glycines), *rhizoctonia* aerial, foliage, and web blight (*Rhizoctonia solani*), rust (Phakopsora pachyrhizi), scab (Sphaceloma glycines), *stemphylium* leaf blight (*Stemphylium botryosum*), target spot (Corynespora cassiicola).

Fungal diseases on roots and the stem base caused, for example, by black root rot (Calonectria crotalariae), charcoal rot (Macrophomina phaseolina), *fusarium* blight or wilt, root rot, and pod and collar rot (*Fusarium oxysporum, Fusarium orthoceras, Fusarium semitectum, Fusarium equiseti*), mycoleptodiscus root rot (Mycoleptodiscus terrestris), neocosmospora (Neocosmospora vasinfecta), pod and stem blight (*Diaporthe phaseolorum*), stem canker (*Diaporthe phaseolorum* var. *caulivora*), phytophthora rot (*Phytophthora megasperma*), brown stem rot (Phialophora gregata), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (Thielaviopsis basicola).

The active compound combinations according to the invention can be employed particularly successfully for controlling cereal diseases such as, for example, against *Puccinia* species and diseases in viticulture and fruit and vegetable growing such as, for example, against *Botrytis, Venturia* or *Alternaria* species.

In addition, the active compound combinations according to the invention also have very good antimycotic activity. They have a very broad antimycotic activity spectrum, in particular against dermatophytes and yeasts, moulds and diphasic fungi, (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and audouinii. The list of these fungi by no means constitutes a restriction of the mycotic spectrum covered, and is merely of illustrative character.

In addition, the active compound combinations according to the invention also have very good insecticidal activity. They have a very broad spectrum of insecticidal activity, in particular against the following animal pests:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., Vasates lycopersici.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, Onychiurus armatus.

From the order of the Dermaptera, for example, Forficula auricularia.

From the order of the Diplopoda, for example, Blaniulus guttulatus.

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., Loa Loa, *Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is furthermore possible to control protozoa, such as Eimeria.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus,* Miridae, *Nezara* spp., *Oebalus* spp., Pentomidae, *Piesma quadrata,* Piezodorus spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma pini, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example, *Diprion* spp., *Hoplocampa* spp., *Lasius* spp., *Monomorium pharaonis* and *Vespa* spp.

From the order of the Isopoda, for example, Armadillidium vulgare, Oniscus asellus and Porcellio scaber.

From the order of the Isoptera, for example, *Reticulitermes* spp., *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia* kuehniella, *Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Leucoptera* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Rachiplusia ni, Spodoptera* spp., *Thermesia gemmatalis, Tinea pellionella, Tineola bisselliella, Tortrix viridana, Trichoplusia* spp., *Tuta* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp. and *Xenopsylla* cheopis.

From the order of the Symphyla, for example, Scutigerella immaculata.

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans* and *Xiphinema* spp.

In the protection of materials, the active compound combinations according to the invention can be employed for protecting industrial materials against infection with, and destruction by, unwanted microorganisms.

Industrial materials in the present context are understood as meaning non-living materials which have been prepared for use in industry. For example, industrial materials which are to be protected by inventive active compounds from microbial alteration or destruction may be adhesives, sizes, paper and board, textiles, leather, wood, paints and plastic articles, cooling lubricants and other materials which can be infected with or destroyed by microorganisms. The range of materials to be protected also includes parts of production plants, for example cooling water circuits, which may be impaired by the proliferation of microorganisms. Industrial materials within the scope of the present invention preferably include adhesives, sizes, paper and card, leather, wood, paints, cooling lubricants and heat transfer fluids, more preferably wood.

Microorganisms capable of degrading or altering the industrial materials include, for example, bacteria, fungi, yeasts, algae and slime organisms. The active compound combinations according to the invention preferably act against fungi, in particular moulds, wood-discolouring and wood-destroying fungi (Basidiomycetes), and against slime organisms and algae.

Examples include microorganisms of the following genera:

Alternaria such as *Alternaria tenuis*,
Aspergillus such as *Aspergillus niger*,
Chaetomium such as Chaetomium globosum,
Coniophora such as Coniophora puetana,
Lentinus such as *Lentinus tigrinus*,
Penicillium such as *Penicillium glaucum*,
Polyporus such as *Polyporus versicolor*,
Aureobasidium such as *Aureobasidium pullulans*,
Sclerophoma such as Sclerophoma pityophila,
Trichoderma such as *Trichoderma viride*,
Escherichia such as *Escherichia coli*,
Pseudomonas such as *Pseudomonas aeruginosa*, and
Staphylococcus such as *Staphylococcus aureus*.

Moreover, it has been found that the active compound combinations according to the invention show a potent insecticidal action against insects which destroy industrial materials.

Preferred but nonlimiting examples include the following insects:

beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. Dinoderus minutus.

Dermapterans, such as Sirex juvencus, Urocerus gigas, Urocerus gigas taignus, Urocerus augur.

Termites, such as *Kalotermes flavicollis, Cryptotermes brevis, Heterotermes indicola, Reticulitermes flavipes, Reticulitermes santonensis, Reticulitermes lucifugus, Mastotermes* darwiniensis, *Zootermopsis nevadensis, Coptotermes formosanus*.

bristletails, such as Lepisma saccarina.

Industrial materials in the present connection are understood to mean inanimate materials, such as preferably plastics, adhesives, sizes, papers and cards, leather, wood, processed wood products and coating compositions.

Most preferably, the material to be protected from insect infestation comprises wood and processed wood products.

Wood and timber products which can be protected by the active compound combinations according to the invention are to be understood as meaning, for example: building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compound combinations can be used as such, in the form of concentrates or generally customary formulations such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal active compound combinations or concentrates used for the preservation of wood and wood-derived timber products comprise the active compound according to the invention in a concentration of 0.0001 to 95% by weight, in particular 0.001 to 60% by weight.

The amount of the active compound combinations or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

The active compound combinations are also suitable for controlling animal pests, in particular insects, arachnids and mites, which are encountered in enclosed spaces, for example dwellings, factory halls, offices, vehicle cabins and the like. They can be used in domestic insecticide products for controlling these pests. They are effective against sensitive and resistant species, and against all developmental stages. These pests include:

From the order of the Scorpionidea, for example, Buthus occitanus.

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, Aviculariidae, Araneidae.

From the order of the Opiliones, for example, Pseudoscorpiones chelifer, Pseudoscorpiones cheiridium, Opiliones phalangium.

From the order of the Isopoda, for example, Oniscus asellus, Porcellio scaber. From the order of the Diplopoda, for example, Blaniulus guttulatus, *Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, Forficula auricularia.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex* quinquefasciatus, *Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

The active compound combinations according to the invention are not only active against plant pests, hygiene pests and stored-product pests, but also, in the veterinary medicine sector, against animal parasites (ectoparasites) such as hard ticks, soft ticks, mange mites, harvest mites, flies (stinging and licking), parasitizing fly larvae, lice, hair lice, bird lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattela germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compound combinations according to the invention are also suitable for controlling arthropods which attack agricultural livestock such as, for example, cattle, sheep, goats, horses, pigs, donkeys, camels, buffaloes, rabbits, chickens, turkeys, ducks, geese, honey-bees, other domestic animals such as, for example, dogs, cats, caged birds, aquarium fish and so-called experimental animals such as, for example, hamsters, guinea pigs, rats and mice. The control of these arthropods is intended to reduce cases of death and reduced productivity (of meat, milk, wool, hides, eggs, honey etc.), and so more economic and easier animal husbandry is possible by use of the active compound combinations according to the invention.

The active compound combinations according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, domestic animals and the like, the active compound combinations can be applied as formulations (for example powders, emulsions, flowables) comprising the active compounds in an amount of 1 to 80% by weight, either directly or after 100- to 10 000-fold dilution, or they may be used as a chemical dip.

If appropriate, the active compound combinations according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms).

The active compounds can be converted into the customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active compound, synthetic substances impregnated with active compound, fertilizers and also microencapsulations in polymeric substances.

These formulations are produced in a known manner, for example by mixing the active compounds with extenders, i.e. liquid solvents, and/or solid carriers, optionally with the use of surfactants, i.e. emulsifiers and/or dispersants, and/or foam formers. The formulations are produced either in suitable plants or else before or during application.

Suitable for use as auxiliaries are substances which are suitable for imparting to the composition itself and/or to preparations derived therefrom (for example spray liquors, seed dressings) particular properties such as certain technical properties and/or also particular biological properties. Typical auxiliaries include: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

According to the invention, a carrier is a natural or synthetic, organic or inorganic substance which may be solid or liquid and with which the active compounds are mixed or bonded for better applicability, in particular for application to plants or plant parts or seed. The solid or liquid carrier is generally inert and should be suitable for use in agriculture.

Suitable solid or liquid carriers are:

for example ammonium salts and natural rock flours, such as kaolins, clays, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, maize cobs and tobacco stalks; useful emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Furthermore, suitable oligomers or polymers, for example those derived from vinylic monomers, from acrylic acid, from EO and/or PO alone or in combination with, for example, (poly)alcohols or (poly)amines. It is also possible to use lignin and its sulphonic acid derivatives, unmodified and modified celluloses, aromatic and/or aliphatic sulphonic acids and also their adducts with formaldehyde.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

Other possible additives are perfumes, mineral or vegetable oils which are optionally modified, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability, may also be present.

The active compound content of the use forms prepared from the commercially available formulations may vary within wide limits. The active compound concentration of the use forms is in the range of from 0.00000001 to 97% by weight of active compound, preferably in the range of from 0.0000001 to 97% by weight, particularly preferably in the range of from 0.000001 to 83% by weight or 0.000001 to 5% by weight, and very particularly preferably in the range of from 0.0001 to 1% by weight.

The active compound combinations according to the invention can be present in their commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

A mixture with other known active compounds, such as herbicides, fertilizers, growth regulators, safeners, semiochemicals, or else with agents for improving the plant properties, is also possible.

When used as fungicides and/or insecticides, the active compound combinations according to the invention can furthermore be present in their commercially available formulations and in the use forms, prepared from these formulations, as a mixture with synergists. Synergists are compounds which increase the action of the active compounds, without it being necessary for the synergist added to be active itself.

When used as fungicides and/or insecticides, the active compound combinations according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The compounds are employed in a customary manner appropriate for the use forms.

All plants and plant parts can be treated in accordance with the invention. Plants are understood here to mean all plants and plant populations, such as desired and undesired wild plants or crop plants (including naturally occurring crop plants). Crop plants can thus be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and also vegetative and generative propagation material, for example fruits, seeds, cuttings, tubers, rhizomes, slips, seed, bulbils, layers and runners.

Treatment according to the invention of the plants and plant parts with the active compound combinations is carried out directly or by allowing the compounds to act on the surroundings, environment or storage space by the customary treatment methods, for example by immersion, spraying, evaporation, fogging, scattering, painting on, injection and, in the case of propagation material, in particular in the case of seeds, also by applying one or more coats. Here, the active compound combinations can be prepared prior to the treatment by mixing the individual active compounds. Alternatively, the treatment is carried out successively by initially using a compound of the formula (I), followed by treatment with an active compound of groups (2) to (27). However, it is also possible to treat the plants or plant parts first with an active compound of groups (2) to (27), followed by treatment with a compound of the formula I.

The following plants may be mentioned as plants which can be treated according to the invention: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for example banana plants and banana plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leeks, onions), *Papilionaceae* sp. (for example peas); major crop plants such as *Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak Choi, kohlrabi, small radishes, and also oilseed rape, mustard, horseradish and cress), *Fabacae* sp. (for example beans, peanuts), *Papilionaceae* sp. (for example soya bean), *Solanaceae* sp. (for example potatoes), *Chenopodiaceae* sp. (for example sugar beet, fodder beet, Swiss chard, beetroot); useful plants and ornamental plants in gardens and forests; and in each case genetically modified types of these plants.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNAi technology [RNA interference]). A heterologous gene that is located in the genome is also called a transgene. A transgene that is defined by its particular location in the plant genome is called a transformation or transgenic event.

Depending on the plant species or plant varieties, their location and growth conditions (soils, climate, vegetation period, diet), the treatment according to the invention may also result in superadditive ("synergistic") effects. For example, the following effects exceeding the effects actually to be expected are possible: reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processibility of the harvested products.

At certain application rates, the active compound combinations according to the invention may also have a strengthening effect in plants. Accordingly, they are suitable for mobilizing the defence system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, also those substances or combinations of substances which are capable of stimulating the defence system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are understood as meaning phytopathogenic fungi, bacteria and viruses. Thus, the substances according to the invention can be employed for protecting plants against attack by the abovementioned pathogens within a certain period of time after the treatment. The period within which protection is brought about generally extends from 1 to 10 days, preferably 1 to 7 days, after the treatment of the plants with the active compounds.

Plants and plant varieties which are preferably treated according to the invention include all plants which have genetic material which imparts particularly advantageous, useful traits to these plants (whether obtained by breeding and/or biotechnological means).

Plants and plant varieties which are also preferably treated according to the invention are resistant against one or more biotic stress factors, i.e. said plants have a better defence against animal and microbial pests, such as against nematodes, insects, mites, phytopathogenic fungi, bacteria, viruses and/or viroids.

Plants and plant varieties which may also be treated according to the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant varieties which may also be treated according to the invention are those plants characterized by enhanced yield characteristics Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis, or hybrid vigour, which results in generally higher yield, increased vigour, better health and better resistance towards biotic and abiotic stress factors. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (e.g. in maize) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described in *Brassica* species (WO 1992/005251, WO 1995/009910, WO 1998/27806, WO 2005/002324, WO 2006/021972 and U.S. Pat. No. 6,229,072). However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar (e.g. WO 1991/002069).

Plants or plant varieties (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a petunia EPSPS (Shah et al., Science (1986), 233, 478-481), a tomato EPSPS (Gasser et al., J. Biol. Chem. (1988), 263, 4280-4289) or an *Eleusine* EPSPS (WO 2001/66704). It can also be a mutated EPSPS, as described, for example, in EP-A 0837944, WO 2000/066746, WO 2000/066747 or WO 2002/026995. Glyphosate-tolerant plants can also be obtained by expressing a gene that encodes a glyphosate oxidoreductase enzyme as described in U.S. Pat. No. 5,776,760 and U.S. Pat. No. 5,463,175. Glyphosate-tolerant plants can also be obtained by expressing a gene that encodes a glyphosate acetyltransferase enzyme as described, for example, in WO 2002/036782, WO 2003/092360, WO 2005/012515 and WO 2007/024782. Glyphosate-tolerant plants can also be obtained by selecting plants containing naturally occurring mutations of the abovementioned genes as described, for example, in WO 2001/024615 or WO 2003/013226.

Other herbicide-resistant plants are for example plants which have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species for example). Plants expressing an exogenous phosphinothricin acetyltransferase have been described, for example, in U.S. Pat. No. 5,561,236; U.S. Pat. No. 5,648,477; U.S. Pat. No. 5,646,024; U.S. Pat. No. 5,273,894; U.S. Pat. No. 5,637,489; U.S. Pat. No. 5,276,268; U.S. Pat. No. 5,739,082; U.S. Pat. No. 5,908,810 and U.S. Pat. No. 7,112,665.

Further herbicide-tolerant plants are also plants that have been made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme according to WO 1996/038567, WO 1999/024585 and WO 1999/024586. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 1999/034008 and WO 2002/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928.

Further herbicide-resistant plants are plants that have been made tolerant to acetolactate synthase (ALS) inhibitors. Known ALS inhibitors include, for example, sulphonylurea, imidazolinone, triazolopyrimidines, pyrimidinyl oxy(thio) benzoates, and/or sulphonylaminocarbonyltriazolinone herbicides. Different mutations in the ALS enzyme (also known as acetohydroxy acid synthase, AHAS) are known to confer tolerance to different herbicides and groups of herbicides, as described, for example, in Tranel and Wright, Weed Science (2002), 50, 700-712, and also in U.S. Pat. No. 5,605,011, U.S. Pat. No. 5,378,824, U.S. Pat. No. 5,141,870 and U.S. Pat. No. 5,013,659. The production of sulphonylurea-tolerant plants and imidazolinone-tolerant plants has been described in U.S. Pat. No. 5,605,011; U.S. Pat. No. 5,013,659; U.S. Pat. No. 5,141,870; U.S. Pat. No. 5,767,361; U.S. Pat. No. 5,731,180; U.S. Pat. No. 5,304,732; U.S. Pat. No. 4,761,373; U.S. Pat. No. 5,331,107; U.S. Pat. No. 5,928,937; and U.S. Pat. No. 5,378,824; and also in the international publication WO 1996/033270. Further imidazolinone-tolerant plants have also been described, for example in WO 2004/040012, WO 2004/

106529, WO 2005/020673, WO 2005/093093, WO 2006/007373, WO 2006/015376, WO 2006/024351 and WO 2006/060634. Further sulphonylurea- and imidazolinone-tolerant plants have also been described, for example in WO 2007/024782.

Other plants tolerant to imidazolinone and/or sulphonylurea can be obtained by induced mutagenesis, by selection in cell cultures in the presence of the herbicide or by mutation breeding, as described, for example, for soya beans in U.S. Pat. No. 5,084,082, for rice in WO 1997/41218, for sugar beet in U.S. Pat. No. 5,773,702 and WO 1999/057965, for lettuce in U.S. Pat. No. 5,198,599 or for sunflower in WO 2001/065922.

Plants or plant varieties (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:
1) an insecticidal crystal protein from *Bacillus thuringiensis* or an insecticidal portion thereof, such as the insecticidal crystal proteins compiled by Crickmore et al., Microbiology and Molecular Biology Reviews (1998), 62, 807-813, updated by Crickmore et al. (2005) in the *Bacillus thuringiensis* toxin nomenclature, (online at: http://www.lifesci.sussex.ac.uk/Home/Neil_Crickmore/Bt/), or insecticidal portions thereof, for example proteins of the Cry protein classes Cry1Ab, Cry1Ac, Cry1F, Cry2Ab, Cry3Ae or Cry3Bb or insecticidal portions thereof; or
2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins (Moellenbeck et al., Nat. Biotechnol. (2001), 19, 668-72; Schnepf et al., Applied Environm. Microb. (2006), 71, 1765-1774); or
3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by maize event MON98034 (WO 2007/027777); or
4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR604; or
5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/home/Neil_Crickmore/Bt/vip.html, for example proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 1994/21795); or
7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant varieties (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:
a. plants which contain a transgene capable of reducing the expression and/or the activity of the poly(ADP-ribose)polymerase (PARP) gene in the plant cells or plants, as described in WO 2000/004173 or EP 04077984.5 or EP 06009836.5.
b. plants which contain a stress tolerance-enhancing transgene capable of reducing the expression and/or the activity of the PARG encoding genes of the plants or plant cells, as described, for example, in WO 2004/090140;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase, as described, for example, in EP 04077624.7 or WO 2006/133827 or PCT/EP07/002, 433.

Plants or plant varieties (obtained by plant biotechnology methods such as genetic engineering) which may also be treated according to the invention show altered quantity, quality and/or storage stability of the harvested product and/or altered properties of specific ingredients of the harvested product such as, for example:
1) Transgenic plants which synthesize a modified starch which is altered with respect to its chemophysical traits, in particular the amylose content or the amylose/amylopectin ratio, the degree of branching, the average chain length, the distribution of the side chains, the viscosity behaviour, the gel resistance, the grain size and/or grain morphology of the starch in comparison to the synthesized starch in wild-type plant cells or plants, such that this modified starch is better suited for certain applications. These transgenic plants synthesizing a modified starch are described, for example, in EP 0571427, WO 1995/004826, EP 0719338, WO 1996/15248, WO 1996/19581, WO 1996/27674, WO 1997/11188, WO 1997/26362, WO 1997/32985, WO 1997/42328, WO 1997/44472, WO 1997/45545, WO 1998/27212, WO 1998/40503, WO 99/58688, WO 1999/58690, WO 1999/58654, WO 2000/008184, WO 2000/008185, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 1995/26407, WO 1996/34968, WO 1998/20145, WO 1999/12950, WO 1999/66050, WO 1999/53072, U.S. Pat. No. 6,734,341, WO 2000/11192, WO 1998/22604, WO 1998/32326, WO 2001/98509, WO 2001/98509, WO 2005/002359, U.S. Pat. No. 5,824,790, U.S. Pat. No. 6,013,861, WO 1994/004693, WO 1994/009144, WO 1994/11520, WO 1995/35026 and WO 1997/20936.

2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, as described in EP 0663956, WO 1996/001904, WO 1996/021023, WO 1998/039460 and WO 1999/024593, plants which produce alpha-1,4-glucans, as described in WO 1995/031553, US 2002/031826, U.S. Pat. No. 6,284,479, U.S. Pat. No. 5,712,107, WO 1997/047806, WO 1997/047807, WO 1997/047808 and WO 2000/14249, plants which produce alpha-1,6-branched alpha-1,4-glucans, as described in WO 2000/73422, and plants which produce alternan, as described in WO 2000/047727, EP 06077301.7, U.S. Pat. No. 5,908,975 and EP 0728213.

3) Transgenic plants which produce hyaluronan, as described, for example, in WO 2006/032538, WO 2007/039314, WO 2007/039315, WO 2007/039316, JP 2006/304779 and WO 2005/012529.

Plants or plant varieties (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:
a) plants, such as cotton plants, which contain an altered form of cellulose synthase genes, as described in WO 1998/000549;
b) plants, such as cotton plants, which contain an altered form of rsw2 or rsw3 homologous nucleic acids, as described in WO 2004/053219;
c) plants, such as cotton plants, with increased expression of sucrose phosphate synthase as described in WO 2001/017333;
d) plants, such as cotton plants, with an increased expression of sucrose synthase, as described in WO 02/45485;
e) plants, such as cotton plants, wherein the timing of the plasmodesmatal gating at the basis of the fibre cell is altered, for example through downregulation of fibre-selective β-1,3-glucanase as described in WO 2005/017157;
f) plants, such as cotton plants, which have fibres with altered reactivity, for example through the expression of the N-acetylglucosaminetransferase gene including nodC and chitin synthase genes, as described in WO 2006/136351.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:
a) plants, such as oilseed rape plants, which produce oil having a high oleic acid content, as described, for example, in U.S. Pat. No. 5,969,169, U.S. Pat. No. 5,840,946 or U.S. Pat. No. 6,323,392 or U.S. Pat. No. 6,063,947;
b) plants, such as oilseed rape plants, which produce oil having a low linolenic acid content, as described in U.S. Pat. No. 6,270,828, U.S. Pat. No. 6,169,190 or U.S. Pat. No. 5,965,755;
c) plants, such as oilseed rape plants, which produce oil having a low level of saturated fatty acids, as described, for example, in U.S. Pat. No. 5,434,283.

Particularly useful transgenic plants which may be treated according to the invention are plants which comprise one or more genes which encode one or more toxins and are the transgenic plants available under the following trade names: YIELD GARD® (for example corn, cotton, soybeans), KnockOut® (for example corn), BiteGard® (for example corn), BT-Xtra® (for example corn), StarLink® (for example corn), Bollgard® (cotton), Nucotn® (cotton), Nucotn 33B® (cotton), NatureGard® (for example corn), Protecta® and NewLeaf® (potato). Examples of herbicide-tolerant plants which may be mentioned are maize varieties, cotton varieties and soya bean varieties which are available under the following trade names: Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, and that are listed for example in the databases for various national or regional regulatory agencies (see for example http://gmoinfo.jrc.it/gmp_browse.aspx and http://www.agbios.com/dbase.php).

The active compound combinations according to the invention are particularly suitable for the treatment of seed. Here, particular mention may be made of the combinations according to the invention mentioned above as preferred or particularly preferred. Thus, most of the damage to crop plants which is caused by phytopathogenic fungi and/or animal pests occurs as early as when the seed is infested during storage and after the seed is introduced into the soil, and during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of phytopathogenic fungi and/or animal pests by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection products after sowing or after emergence of the plants. It is furthermore desirable to optimize the amount of active compound employed in such a way as to provide optimum protection for the seed and the germinating plant from attack by phytopathogenic fungi and/or animal pests, but without damaging the plant itself by the active compound employed. In particular, methods for the treatment of seed should also take into consideration the intrinsic fungicidal and/or insecticidal properties of transgenic plants in order to achieve optimum protection of the seed and the germinating plant with a minimum of crop protection products being employed.

Accordingly, the present invention also relates in particular to a method for protecting seed and germinating plants against attack by phytopathogenic fungi and/or animal pests by treating the seed with an active compound combination according to the invention. The method according to the invention for protecting seed and germinating plants against attack by phytopathogenic fungi and/or animal pests comprises a method where the seed is treated simultaneously with a compound of the formula (I) and an active compound from groups (2) to (27) listed above. It also comprises a method where the seed is treated at different times with a compound of the formula (I) and an active compound from groups (2) to (27) listed above.

The invention also relates to the use of the active compound combinations according to the invention for treating seed for protecting the seed and the germinating plant against phytopathogenic fungi and/or animal pests.

Furthermore, the invention relates to seed treated with an active compound combination according to the invention for protection against phytopathogenic fungi and/or animal pests. The invention also relates to seed treated simultaneously with a compound of the formula (I) and an active compound from groups (2) to (27) listed above. The invention furthermore relates to seed treated at different times with a compound of the formula (I) and an active compound from groups (2) to (27) listed above. In the case of seed treated at different times with a compound of the formula (I) and an active compound from groups (2) to (27) listed above, the individual active compounds of the active compound combination according to the invention may be present in different layers on the seed. The layers comprising a compound of the formula (I) and an active compound from groups (2) to (27) listed above may optionally be separated by an intermediate layer. The invention also relates to seed where a compound of the formula (I) and an active compound from groups (2) to (27) listed above are applied as component of a coating or as a further layer or further layers in addition to a coating.

One of the advantages of the present invention is that, because of the particular systemic properties of the active compound combinations according to the invention, treatment of the seed with these compositions not only protects the seed itself, but also the resulting plants after emergence, from phytopathogenic fungi and/or animal pests. In this manner, the immediate treatment of the crop at the time of sowing or shortly thereafter can be dispensed with.

A further advantage is the synergistically increased insecticidal activity of the active compound combinations according to the invention in comparison with the individual insecticidally active compound, which exceeds the expected activity of the two active compounds when applied individually. Also advantageous is the synergictic enhancement of the fungicidal activity of the active compound combinations according to the invention compared with the individual fungicidally active compound, which exceeds the expected activity of the active compound applied individually. This makes possible an optimization of the amount of active compounds employed.

It is likewise to be considered advantageous that the active compound combinations according to the invention can be used in particular also for transgenic seed.

The active compound combinations according to the invention are suitable for protecting seed of any plant variety as already mentioned above which is employed in agriculture, in the greenhouse, in forests or in horticulture. In particular, this takes the form of seed of maize, peanut, canola, oilseed rape, poppy, soya beans, cotton, beet (for example sugar beet and fodder beet), rice, millet, wheat, barley, oats, rye, sunflower, tobacco, potatoes or vegetables (for example tomatoes, cabbage species). The active compound combinations according to the invention are likewise suitable for treating the seed of fruit plants and vegetables as already mentioned above. The treatment of the seed of maize, soya beans, cotton, wheat and canola or oilseed rape is of particular importance.

Within the context of the present invention, the active compound combination according to the invention is applied to the seed either alone or in a suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the active compound combination according to the invention applied to the seed and/or the amount of further additives is chosen in such a way that the germination of the seed is not adversely affected, or that the resulting plant is not damaged. This must be borne in mind in particular in the case of active compounds which can have phytotoxic effects at certain application rates.

The compositions according to the invention can be applied directly, i.e. without containing any other components and undiluted. In general, it is preferred to apply the compositions to the seed in the form of a suitable formulation. Suitable formulations and methods for treating seed are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compounds which can be used in accordance with the invention can be converted into the customary seed-dressing formulations, such as solutions, emulsions, suspensions, powders, foams, slurries or other coating compositions for seed, and also ULV formulations.

These formulations are prepared in a known manner, by mixing the active compounds with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations which can be used in accordance with the invention are all colorants which are customary for such purposes. In this context, not only pigments, which are sparingly soluble in water, but also dyes, which are soluble in water, may be used. Examples include the dyes known by the names Rhodamine B, C.I. Pigment Red 112 and C.I. Solvent Red 1.

Suitable wetting agents which may be present in the seed-dressing formulations which can be used in accordance with the invention are all substances which promote wetting and which are conventionally used for the formulation of agrochemical active compounds. Preference is given to using alkylnaphthalenesulphonates, such as diisopropyl or diisobutylnaphthalenesulphonates.

Suitable dispersants and/or emulsifiers which may be present in the seed-dressing formulations which can be used in accordance with the invention are all nonionic, anionic and cationic dispersants conventionally used for the formulation of agrochemical active compounds. Preference is given to using nonionic or anionic dispersants or mixtures of nonionic or anionic dispersants. Suitable nonionic dispersants which may be mentioned are, in particular, ethylene oxide/propylene oxide block polymers, alkylphenol polyglycol ethers and tristryrylphenol polyglycol ether, and their phosphated or sulphated derivatives. Suitable anionic dispersants are, in particular, lignosulphonates, polyacrylic acid salts and arylsulphonate/formaldehyde condensates.

Antifoams which may be present in the seed-dressing formulations which can be used in accordance with the invention are all foam-inhibiting substances conventionally used for the formulation of agrochemical active compounds. Silicone antifoams and magnesium stearate can preferably be used.

Preservatives which may be present in the seed-dressing formulations which can be used in accordance with the invention are all substances which can be employed for such purposes in agrochemical compositions. Dichlorophene and benzyl alcohol hemiformal may be mentioned by way of example.

Secondary thickeners which may be present in the seed-dressing formulations which can be used in accordance with the invention are all substances which can be employed for such purposes in agrochemical compositions. Cellulose derivatives, acrylic acid derivatives, xanthan, modified clays and finely divided silica are preferred.

Adhesives which may be present in the seed-dressing formulations which can be used in accordance with the invention are all customary binders which can be employed in seed-dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- and Schädlingsbekampfungsmittel" [Chemistry of the Crop Protection Compositions and Pesticides], vol. 2, Springer Verlag, 1970, pp. 401-412).

The seed-dressing formulations which can be used in accordance with the invention can be employed for the treatment of a wide range of seed, including the seed of transgenic plants, either directly or after previously having been diluted with water. In this context, additional synergistic effects may also occur in cooperation with the substances formed by expression.

All mixers which can conventionally be employed for the seed-dressing operation are suitable for treating seed with the seed-dressing formulations which can be used in accordance with the invention or with the preparations prepared therefrom by addition of water. Specifically, a procedure is followed during the seed-dressing operation in which the seed is placed into a mixer, the specific desired amount of seed-dressing formulations, either as such or after previously having been diluted with water, is added, and everything is mixed until the formulation is distributed uniformly on the seed. If appropriate, this is followed by a drying process.

The active compound combinations according to the invention are also suitable for increasing the yield of crops. In addition, they have reduced toxicity and are well tolerated by plants.

The active compound combinations according to the invention also exhibit a potent strengthening effect in plants. They can therefore be used to mobilize the plant's own defences against attack by unwanted microorganisms.

Plant-strengthening (resistance-inducing) substances are to be understood as meaning, in the present context, those substances which are capable of stimulating the defence system of plants in such a way that the treated plants, when subsequently inoculated with unwanted microorganisms, develop a high degree of resistance to these microorganisms.

In the present case, unwanted microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The plants listed can be treated according to the invention in a particularly advantageous manner with the active compound mixtures according to the invention. The preferred ranges stated above for the active compound combinations also apply to the treatment of these plants. Particular emphasis is given to the treatment of plants with the active compound combinations specifically mentioned in the present text.

The good insecticidal and fungicidal action of the active compound combinations according to the invention can be seen from the examples which follow. While the individual active compounds show weaknesses in their action, the combinations show an action which exceeds a simple sum of actions.

A synergistic effect in insecticides and fungicides is always present when the insecticidal or fungicidal action of the active compound combinations exceeds the total of the actions of the active compounds when applied individually.

The expected insecticidal or fungicidal action for a given combination of two active compounds can be calculated according to S. R. Colby ("Calculating Synergistic and Antagonistic Responses of Herbicide Combinations", Weeds 1967, 15, 20-22), as follows:

If

X is the kill rate or efficacy, expressed in % of the untreated control, when the active compound A is used at an application rate of m ppm or g/ha, Y is the kill rate or efficacy, expressed in % of the untreated control, when the active compound B is used at an application rate of n ppm or g/ha, E is the kill rate or efficacy, expressed in % of the untreated control, when the active compounds A and B are used at application rates of m ppm and n ppm or g/ha, respectively, $$E = X + Y - \frac{X \times Y}{100}$$

then

Here, the kill rate or efficacy is determined in %. 0% means a kill rate or an efficacy that corresponds to that of the control, whereas a kill rate of 100% means that all animals are dead and an efficacy of 100% means that no infection is observed.

If the actual fungicidal or insecticidal activity exceeds the calculated value, the activity of the combination is superadditive, i.e. a synergistic effect is present. In this case, the actually observed efficacy must exceed the value calculated using the above formula for the expected efficacy (E).

EXAMPLES

Example A

Myzus persicae Test

Solvents: 78 parts by weight of acetone 1.5 parts by weight of dimethylformamide
Emulsifier: 0.5 part by weight of alkylaryl polyglycol ether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by spraying with the active compound preparation of the desired concentration.

After the desired period of time, the kill in % is determined 100% means that all of the aphids have been killed; 0% means that none of the aphids have been killed. The kill rates determined are entered into Colby's formula (see above).

In this test, for example, the following active compound combinations in accordance with the present application show a synergistically enhanced activity compared to the active compounds applied individually:

TABLE A-1

| Myzus persicae test | | |
|---|---|---|
| Active compound | Concentration in g/ha | Kill in % after 1$^d$ |
| compound (I-4) | 0.8 | 50 |
| compound (I-5) | 0.8 | 50 |
| fluopyram | 200 | 0 |
| N-[2-(1,3-dimethylbutyl)phenyl]-5-fluoro-1,3-dimethyl-1H-pyrazole-4-carboxamide | 200 | 0 |
| fenamidone | 200 | 0 |
| fludioxonil | 200 | 0 |
| iprodione | 200 | 0 |
| isotianil | 200 | 0 |
| metalaxyl | 200 | 0 |
| propamocarb | 200 | 0 |
| prothioconazole | 200 | 0 |
| tebuconazole | 200 | 0 |
| tolylfluanid | 200 | 0 |
| triadimenol | 200 | 0 |
| | found* | calc.** |
| compound (I-5) + fluopyram (1:250) according to the invention | 0.8 + 200 | 70  50 |
| compound (I-4) + N-[2-(1,3-dimethylbutyl)phenyl]-5-fluoro-1,3-dimethyl-1H-pyrazole-4-carboxamide (1:250) according to the invention | 0.8 + 200 | 70  50 |
| compound (I-5) + N-[2-(1,3-dimethylbutyl)phenyl]-5-fluoro-1,3-dimethyl-1H-pyrazole-4-carboxamide (1:250) according to the invention | 0.8 + 200 | 90  50 |

TABLE A-1-continued

| Myzus persicae test | | |
|---|---|---|
| Active compound | Concentration in g/ha | Kill in % after 1$^d$ |
| compound (I-5) + fenamidone (1:250) according to the invention | 0.8 + 200 | 90  50 |
| compound (I-5) + fludioxonil (1:250) according to the invention | 0.8 + 200 | 80  50 |
| compound (I-4) + iprodione (1:250) according to the invention | 0.8 + 200 | 80  50 |
| compound (I-5) + iprodione (1:250) according to the invention | 0.8 + 200 | 70  50 |
| compound (I-4) + isotianil (1:250) according to the invention | 0.8 + 200 | 70  50 |
| compound (I-4) + metalaxyl (1:250) according to the invention | 0.8 + 200 | 80  50 |
| compound (I-5) + metalaxyl (1:250) according to the invention | 0.8 + 200 | 80  50 |
| compound (I-4) + propamocarb (1:250) according to the invention | 0.8 + 200 | 70  50 |
| compound (I-5) + propamocarb (1:250) according to the invention | 0.8 + 200 | 70  50 |
| compound (I-4) + prothioconazole (1:250) according to the invention | 0.8 + 200 | 80  50 |
| compound (I-5) + prothioconazole (1:250) according to the invention | 0.8 + 200 | 80  50 |
| compound (I-4) + tebuconazole (1:250) according to the invention | 0.8 + 200 | 90  50 |
| compound (I-5) + tebuconazole (1:250) according to the invention | 0.8 + 200 | 90  50 |
| compound (I-4) + tolyfluanid (1:250) according to the invention | 0.8 + 200 | 70  50 |
| compound (I-5) + tolyfluanid (1:250) according to the invention | 0.8 + 200 | 80  50 |
| compound (I-4) + triadimenol (1:250) according to the invention | 0.8 + 200 | 80  50 |

*found = activity found
**calc. = activity calculated using Colby's formula

Example B

Phaedon Cochleariae Larvae Test

Solvents: 78 parts by weight of acetone 1.5 parts by weight of dimethylformamide
Emulsifier: 0.5 part by weight of alkylaryl polyglycol ether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by spraying with the active ingredient formulation of the desired concentration and populated with larvae of the mustard beetle (*Phaedon cochleariae*) while the leaves are still moist.

After the desired period of time, the kill in % is determined 100% means that all beetle larvae have been killed; 0% means that none of the beetle larvae have been killed. The kill rates determined are entered into Colby's formula (see above).

In this test, the following active compound combination in accordance with the present application showed a synergistically enhanced activity compared to the active compounds applied individually:

TABLE B-1

Phaedon cochleariae larvae test

| Active compound | Concentration in g/ha | Kill in % after $2^d$ | |
|---|---|---|---|
| compound (I-6) | 100 | 33 | |
| compound (I-4) | 20 | 0 | |
| compound (I-5) | 20 | 0 | |
| fenamidone | 200 | 0 | |
| prothioconazole | 200 | 0 | |
| trifloxystrobin | 200 | 0 | |
| | | found* | calc.** |
| compound (I-6) + fenamidone (1:2) according to the invention | 100 + 200 | 50 | 33 |
| compound (I-5) + fenamidone (1:10) according to the invention | 20 + 200 | 33 | 0 |
| compound (I-5) + prothioconazole (1:10) according to the invention | 20 + 200 | 33 | 0 |
| compound (I-4) + trifloxystrobin (1:10) according to the invention | 20 + 200 | 17 | 0 |

*found = activity found
**calc. = activity calculated using Colby's formula

TABLE B-2

Phaedon cochleariae larvae test

| Active compound | Concentration in g/ha | Kill in % after $6^d$ | |
|---|---|---|---|
| compound (I-6) | 100 | 67 | |
| | 20 | 0 | |
| compound (I-4) | 100 | 17 | |
| | 20 | 0 | |
| compound (I-5) | 100 | 50 | |
| | 20 | 0 | |
| fluopyram | 200 | 0 | |
| azoxystrobin | 500 | 0 | |
| N-[2-(1,3-dimethylbutyl)phenyl]-5-fluoro-1,3-dimethyl-1H-pyrazole-4-carboxamide | 200 | 0 | |
| fludioxonil | 200 | 17 | |
| fluopicolide | 500 | 0 | |
| fosetyl-Al | 200 | 0 | |
| iprodione | 200 | 0 | |
| iprovalicarb | 200 | 0 | |
| isotianil | 200 | 0 | |
| metalaxyl | 200 | 0 | |
| tebuconazole | 200 | 0 | |
| tolylfluanid | 200 | 17 | |
| triadimenol | 200 | 0 | |
| trifloxystrobin | 200 | 33 | |
| | | found* | calc.** |
| compound (I-6) + fluopyram (1:2) according to the invention | 100 + 200 | 83 | 67 |
| compound (I-6) + azoxystrobin (1:25) according to the invention | 20 + 500 | 17 | 0 |
| compound (I-4) + azoxystrobin (1:5) according to the invention | 100 + 500 | 50 | 17 |
| compound (I-5) + fluopyram (1:10) according to the invention | 20 + 200 | 33 | 0 |
| compound (I-6) + N-[2-(1,3-dimethylbutyl)phenyl]-5-fluoro-1,3-dimethyl-1H-pyrazole-4-carboxamide (1:10) according to the invention | 20 + 200 | 67 | 0 |
| compound (I-5) + N-[2-(1,3-dimethylbutyl)phenyl]-5-fluoro-1,3-dimethyl-1H-pyrazole-4-carboxamide (1:10) according to the invention | 20 + 200 | 50 | 0 |
| compound (I-6) + fludioxonil (1:10) according to the invention | 20 + 200 | 33 | 17 |
| compound (I-4) + fluopicolide (1:5) according to the invention | 100 + 500 | 33 | 17 |
| compound (I-5) + fluopicolide (1:5) according to the invention | 100 + 500 | 100 | 50 |
| compound (I-6) + fosetyl-Al (1:10) according to the invention | 20 + 200 | 17 | 0 |
| compound (I-5) + fosetyl-Al (1:10) according to the invention | 20 + 200 | 33 | 0 |
| compound (I-6) + iprodione (1:10) according to the invention | 20 + 200 | 33 | 0 |
| compound (I-5) + iprodione (1:10) according to the invention | 20 + 200 | 50 | 0 |
| compound (I-5) + iprovalicarb (1:2) according to the invention | 100 + 200 | 83 | 50 |
| compound (I-5) + isotianil (1:10) according to the invention | 20 + 200 | 50 | 0 |
| compound (I-5) + metalaxyl (1:10) according to the invention | 20 + 200 | 33 | 0 |
| compound (I-4) + tebuconazole (1:10) according to the invention | 20 + 200 | 17 | 0 |
| compound (I-5) + tebuconazole (1:10) according to the invention | 20 + 200 | 50 | 0 |
| compound (I-5) + tolyfluanid (1:10) according to the invention | 20 + 200 | 33 | 17 |
| compound (I-6) + triadimenol (1:10) according to the invention | 20 + 200 | 83 | 0 |
| compound (I-4) + triadimenol (1:10) according to the invention | 20 + 200 | 83 | 0 |
| compound (I-5) + triadimenol (1:10) according to the invention | 20 + 200 | 100 | 0 |
| compound (I-6) + trifloxystrobin (1:2) according to the invention | 100 + 200 | 100 | 77.89 |
| compound (I-5) + trifloxystrobin (1:10) according to the invention | 20 + 200 | 67 | 33 |

*found = activity found
**calc. = activity calculated using Colby's formula

Example C

*Spodoptera Frugiperda* Test

Solvents: 78 parts by weight of acetone 1.5 parts by weight of dimethylformamide
Emulsifier: 0.5 part by weight of alkylaryl polyglycol ether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being sprayed with the preparation of active compound of the desired concentration and are populated with larvae of the armyworm (*Spodoptera frugiperda*) while the leaves are still moist.

After the desired period of time, the kill in % is determined 100% means that all caterpillars have been killed; 0% means that none of the caterpillars have been killed. The kill rates determined are entered into Colby's formula (see above).

In this test, the following active compound combinations in accordance with the present application show a synergistically enhanced activity compared to the active compounds applied individually:

TABLE C-1

*Spodoptera frugiperda* test

| Active compound | Concentration in g/ha | Kill in % after $6^d$ | |
|---|---|---|---|
| compound (I-6) | 100 | 0 | |
| fosetyl-Al | 200 | 0 | |
| tolylfluanid | 200 | 0 | |
| | | found* | calc.** |
| compound (I-6) + fosetyl-Al (1:2) according to the invention | 100 + 200 | 33 | 0 |
| compound (I-6) + tolylfluanid (1:2) according to the invention | 100 + 200 | 33 | 0 |

*found = activity found
**calc. = activity calculated using Colby's formula

Example D

*Tetranychus Urticae* Test

Op-Resistant/Spray Treatment

Solvents: 78 parts by weight of acetone 1.5 parts by weight of dimethylformamide Emulsifier: 0.5 part by weight of alkylaryl polyglycol ether To produce a suitable preparation of active compound, 1 part by weight of active compound is mixed with the stated amount of solvent and emulsifier, and the concentrate is diluted with emulsifier-containing water to the desired concentration.

Discs of bean leaves (*Phaseolus vulgaris*) which are infested by all stages of the greenhouse red spider mite (*Tetranychus urticae*) are sprayed with an active compound preparation of the desired concentration.

After the desired period of time, the effect in % is determined. 100% means that all of the spider mites have been killed; 0% means that none of the spider mites have been killed.

In this test, the following active compound combination in accordance with the present application showed a synergistically enhanced activity compared to the active compounds applied individually:

TABLE D-1

*Tetranychus urticae* test

| Active compound | Concentration in g/ha | Kill in % after $2^d$ | |
|---|---|---|---|
| compound (I-6) | 100 | 0 | |
| compound (I-5) | 100 | 20 | |
| propamocarb | 200 | 0 | |
| triadimenol | 200 | 0 | |
| | | found* | calc.** |
| compound (I-6) + propamocarb (1:2) according to the invention | 100 + 200 | 50 | 0 |
| compound (I-5) + triadimenol (1:2) according to the invention | 100 + 200 | 40 | 20 |

*found = activity found
**calc. = activity calculated using Colby's formula

TABLE D-2

*Tetranychus urticae* test

| Active compound | Concentration in g/ha | Kill in % after $6^d$ | |
|---|---|---|---|
| compound (I-6) | 100 | 0 | |
| compound (I-4) | 100 | 80 | |
| | 4 | 50 | |
| compound (I-5) | 100 | 0 | |
| fluopyram | 200 | 0 | |
| fludioxonil | 200 | 0 | |
| fluopicolide | 500 | 0 | |
| iprodione | 200 | 50 | |
| iprovalicarb | 200 | 0 | |
| isotianil | 200 | 0 | |
| metalaxyl | 200 | 0 | |
| propamocarb | 200 | 0 | |
| prothioconazole | 200 | 0 | |
| tebuconazole | 200 | 70 | |
| triadimenol | 200 | 0 | |
| | | found* | calc.** |
| compound (I-4) + fluopyram (1:50) according to the invention | 4 + 200 | 80 | 50 |
| compound (I-5) + fluopyram (1:2) according to the invention | 100 + 200 | 70 | 0 |
| compound (I-5) + fludioxonil (1:2) according to the invention | 100 + 200 | 70 | 0 |
| compound (I-6) + fluopicolide (1:5) according to the invention | 100 + 500 | 50 | 0 |
| compound (I-5) + fluopicolide (1:5) according to the invention | 100 + 500 | 50 | 0 |
| compound (I-5) + iprodione (1:2) according to the invention | 100 + 200 | 70 | 0 |
| compound (I-5) + iprovalicarb (1:2) according to the invention | 100 + 200 | 50 | 0 |
| compound (I-4) + isotianil (1:2) according to the invention | 100 + 200 | 99 | 80 |
| compound (I-5) + isotianil (1:2) according to the invention | 100 + 200 | 80 | 0 |
| compound (I-4) + propamocarb (1:5) according to the invention | 4 + 200 | 70 | 50 |
| compound (I-5) + propamocarb (1:2) according to the invention | 100 + 200 | 50 | 0 |

TABLE D-2-continued

Tetranychus urticae test

| Active compound | Concentration in g/ha | Kill in % after 6$^d$ | |
|---|---|---|---|
| compound (I-4) + prothioconazole (1:2) according to the invention | 100 + 200 | 99 | 80 |
| compound (I-6) + metalaxyl (1:2) according to the invention | 100 + 200 | 70 | 0 |
| compound (I-5) + metalaxyl (1:2) according to the invention | 100 + 200 | 70 | 0 |
| compound (I-5) + triadimenol (1:2) according to the invention | 100 + 200 | 80 | 0 |

*found = activity found
**calc. = activity calculated using Colby's formula

The invention claimed is:

1. A composition comprising at least one compound of the formula (I)

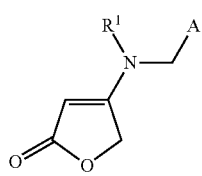

selected from the group consisting of
compound (I-4), 4-{[(6-Chlorpyrid-3-yl)methyl](2-fluorethyl)amino}furan-2(5H)-one

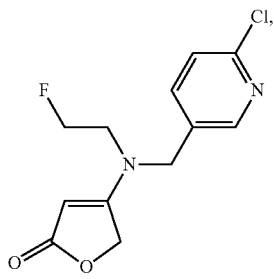 [SMILES: O=C1C=C(N(CCF)Cc2ccc(Cl)nc2)CO1]

compound (I-5), 4-{[(6-Chlorpyrid-3-yl)methyl](2,2-difluorethyl)amino}furan-2(5H)-one

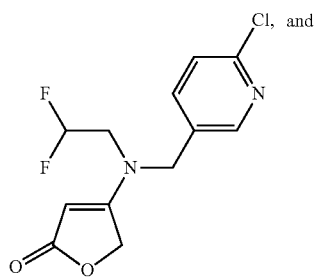 [SMILES: O=C1C=C(N(Cc2ccc(Cl)nc2)CC(F)F)CO1]

compound (I-6), 4-{[(6-Chlor-5-fluorpyrid-3-yl)methyl](methyl)amino}furan-2(5H)-one

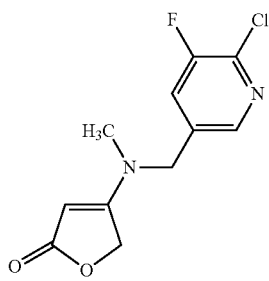 [SMILES: CN(Cc1cnc(Cl)c(F)c1)C1=CC(=O)OC1]

and at least one active compound selected from the group consisting of
(2-4) trifloxystrobin with a mixing ratio of 50:1 to 1:1000,
(3-15) prothioconazole with a mixing ratio of 50:1 to 1:1000,
(6-9) fluopicolid with a mixing ratio of 50:1 to 1:1000,
(6-25) fluopyram with a mixing ratio of 50:1 to 1:1000,
(8-3) metalaxyl with a mixing ratio of 50:1 to 1:1000,
(11-2) propamocarb with a mixing ratio of 250:1 to 1:25,
(16-2) fludioxonil with a mixing ratio of 50:1 to 1:1000, and
(17-1) fosetyl-Al with a mixing ratio of 250:1 to 1:25,
wherein at least one compound of formula (I) and said at least one active compound are present in synergistic amounts.

2. Seed treated with the composition according to claim 1.

3. The composition of claim 1 comprising the compound of formula (I) and fluopyram.

4. The composition of claim 1 comprising compound (I-5) and fluopyram with a mixing ratio of 1:2 to 1:500.

5. The composition of claim 1 comprising the compound of formula (I) and metalaxyl.

6. A method of treating seed comprising contacting seed with the composition according to claim 1.

7. A method of treating transgenic plants comprising contacting the transgenic plants with the composition according to claim 1.

8. A method of treating the seed of transgenic plants comprising contacting the seed of the transgenic plants with the composition of claim 1.

9. A method for controlling insect pests and/or phytopathogenic fungi, characterized in that an active compound combination comprising at least one compound of the formula (I)

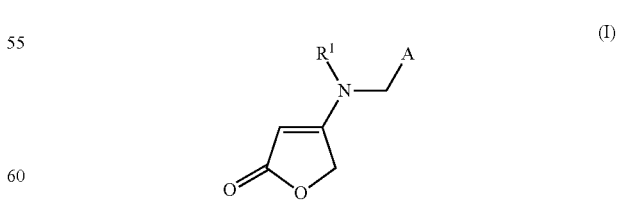

selected from the group consisting of
compound (I-4), 4-{[(6-Chlorpyrid-3-yl)methyl](2-fluorethyl)amino}furan-2(5H)-one

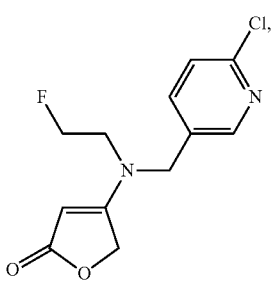

compound (I-5), 4-{[(6-Chlorpyrid-3-yl)methyl](2,2-difluorethyl)amino}furan-2(5H)-one

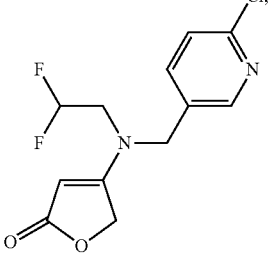

compound (I-6), 4-{[(6-Chlor-5-fluorpyrid-3-yl)methyl](methyl)amino}furan-2(5H)-one

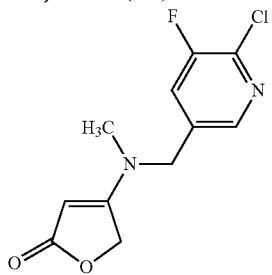

and at least one active compound selected from the group consisting of (2-4) trifloxystrobin with a mixing ratio of 50:1 to 1:1000,
(3-15) prothioconazole with a mixing ratio of 50:1 to 1:1000,
(6-9) fluopicolid with a mixing ratio of 50:1 to 1:1000,
(6-25) fluopyram with a mixing ratio of 50:1 to 1:1000,
(8-3) metalaxyl with a mixing ratio of 50:1 to 1:1000,
(11-2) propamocarb with a mixing ratio of 250:1 to 1:25,
(16-2) fludioxonil with a mixing ratio of 50:1 to 1:1000, and
(17-1) fosetyl-Al with a mixing ratio of 250:1 to 1:25, is allowed to act on the insect pests and/or phytopathogenic fungi and/or their habitat and/or seed, wherein at least one compound of formula (I) and said at least one active compound are present in synergistic amounts.

10. The method of claim 9, characterized in that the compound of formula (I) and said at least one active compound act on seed simultaneously.

11. The method of claim 9, characterized in that the compound of formula (I) and said at least one active compound act on seed at different times.

12. The method of claim 9, wherein the active compound combination comprises compound (I-5) and fluopyram with a mixing ratio of 1:2 to 1:500.

* * * * *